United States Patent
Prince

(10) Patent No.: US 7,072,503 B2
(45) Date of Patent: *Jul. 4, 2006

(54) SYSTEMS AND METHODS FOR DETECTING DEFECTS IN PRINTED SOLDER PASTE

(75) Inventor: David P. Prince, Wakefield, RI (US)

(73) Assignee: Speedline Technologies, Inc., Franklin, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/784,118

(22) Filed: Feb. 20, 2004

(65) Prior Publication Data

US 2004/0218808 A1    Nov. 4, 2004

Related U.S. Application Data

(63) Continuation-in-part of application No. 10/734,395, filed on Dec. 12, 2003, now Pat. No. 6,891,967, which is a continuation-in-part of application No. 09/304,699, filed on May 4, 1999, now Pat. No. 6,738,505.

(51) Int. Cl.
*G06K 9/00* (2006.01)

(52) U.S. Cl. .................... 382/150; 382/151; 356/237.5

(58) Field of Classification Search ................ 382/141, 382/143–151; 348/86, 87, 125, 126; 118/213; 356/257.1, 237.4, 237.5

See application file for complete search history.

(56) References Cited

U.S. PATENT DOCUMENTS 5,060,063 A    10/1991    Freeman
5,172,420 A    12/1992    Ray et al.
RE34,615 E     5/1994     Freeman (Continued)

FOREIGN PATENT DOCUMENTS

GB    2 286 670 A    8/1995

(Continued)

OTHER PUBLICATIONS

*Ritter et al., "Handbook of Computer Vision Algorithms in Image Algebra," CRC Press, Inc., Boca Raton, FL (1996), Ch. 2, 3, 4 and 5 (pp. 51-172).

(Continued)

*Primary Examiner*—Vikkram Bali
(74) *Attorney, Agent, or Firm*—Lowrie, Lando & Anastasi. LLP

(57) ABSTRACT

A method of inspecting a stencil having apertures through which a substance is deposited onto an electronic substrate includes depositing the substance through the stencil and onto the substrate, capturing a first image of the stencil after the deposit of the substance and detecting variations in texture of the substance in the first image, capturing a second image of the electronic substrate having the substance on its surface and detecting variations in texture of the substance in the second image, defining a region of interest in the first image and in the second image to determine whether at least one feature exists in the region of interest, measuring a first span of the at least one feature in the region of interest in the first image and a second span of the at least one feature in the region of interest in the second image, and correlating the first span of the at least one feature and the second span of the at least one feature to determine whether a threshold span of the at least one feature has been reached.

19 Claims, 36 Drawing Sheets

U.S. PATENT DOCUMENTS

| | | | |
|---|---|---|---|
| 5,455,870 A | 10/1995 | Sepai et al. | |
| 5,801,965 A | 9/1998 | Takagi et al. | |
| 5,807,606 A | 9/1998 | Mould et al. | |
| 5,873,939 A | 2/1999 | Doyle et al. | |
| 6,066,206 A | 5/2000 | Doyle et al. | |
| 6,324,973 B1 | 12/2001 | Rossmeisl et al. | |
| 6,362,877 B1 | 3/2002 | Kobayashi et al. | |
| 6,366,690 B1 | 4/2002 | Smilansky et al. | |
| 6,549,648 B1 | 4/2003 | Rinn | |
| 6,738,505 B1 | 5/2004 | Prince | |
| 6,891,967 B1* | 5/2005 | Prince | 382/150 |
| 2002/0019729 A1* | 2/2002 | Chang et al. | 703/6 |
| 2004/0218808 A1 | 11/2004 | Prince | |

FOREIGN PATENT DOCUMENTS

| | | |
|---|---|---|
| WO | WO 95/16247 | 6/1995 |
| WO | WO 98/37741 | 8/1998 |
| WO | WO 00/67005 | 11/2000 |

OTHER PUBLICATIONS

*Russ, John C., "The Image Processing Handbook," 2nd Edition, CRC Press, Inc., Boca Raton, FL (1995), pp. 155-160, 211-237, 259-262, 361-371, 416-431, 481-545.

*Cognex Press Release, "Cognex Introduces New Machine Vision System for Detecting Screen Printing Defects on Printed Circuit Boards," (2 pgs.); http://www.cognex.com/press/release/products/paseteinspect.htm.

*International Search Report for PCT/US00/12121 mailed Sep. 1, 2000.

Brochure, DEK Printing Machines Ltd., "DEK 265GSx Engineering Specifications," Issue 01, Jan. 10, 1996, pp. 2-39.

DEK, "2D Inspection Manual," Issue 2, Jun. 1996, pp. 3-38.

International Search Report for PCT/US2005/004823 mailed May 20, 2005.

International Search Report for PCT/US04/41462 mailed Oct. 4, 2005.

* cited by examiner

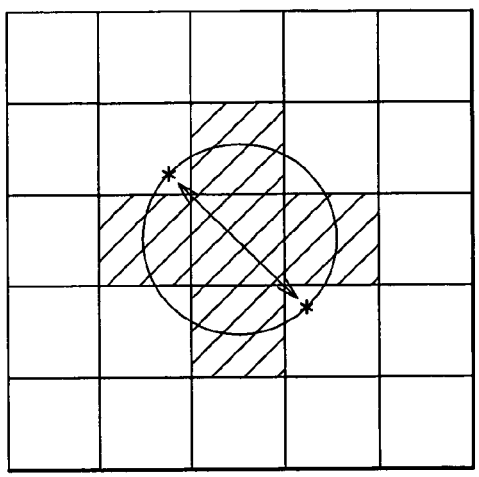
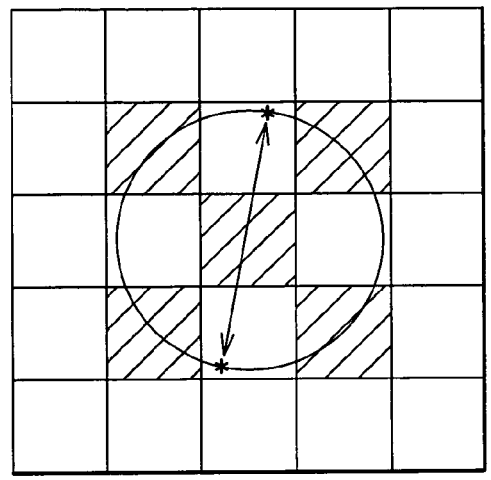
FIG. 8A   FIG. 8B
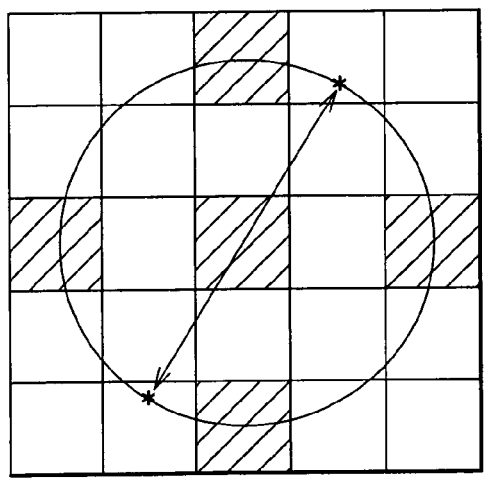
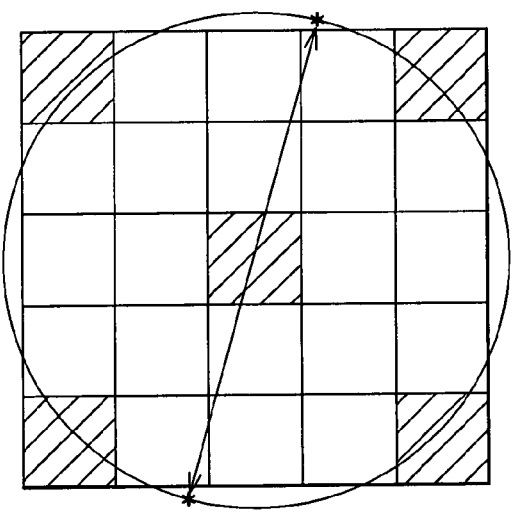
FIG. 8C   FIG. 8D

⌀0.9594

⌀1.3568

⌀1.9188

⌀2.7136

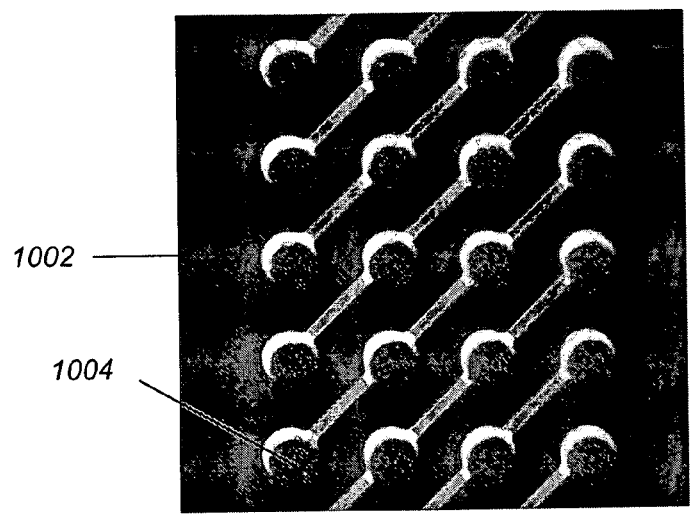
FIG. 10A
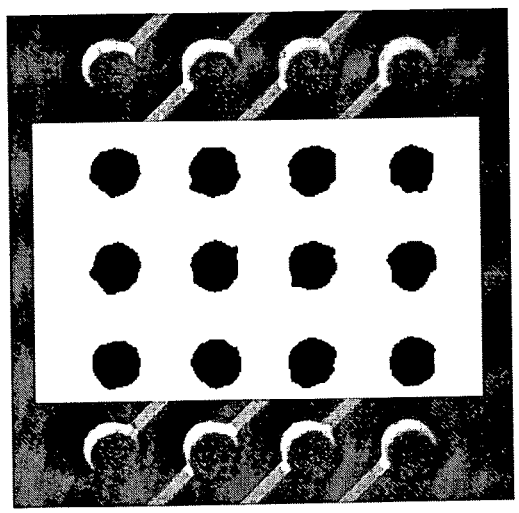 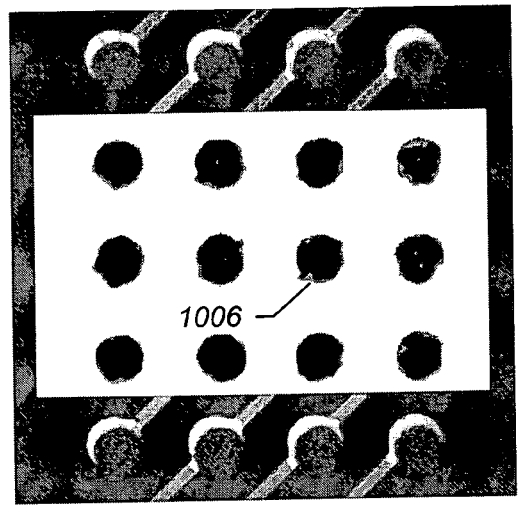
FIG. 10B  FIG. 10C

Grayscale image of paste
using "white" light source.

Weighted paste—only image
via unique texture—based method.

RGB image of UV enhanced
Fluorescent paste.

Binary paste-only image from blue channel
Via single threshold method.

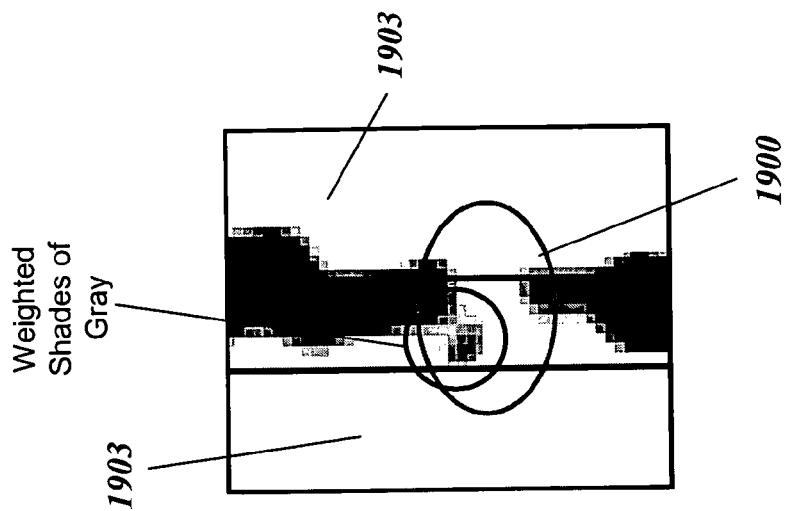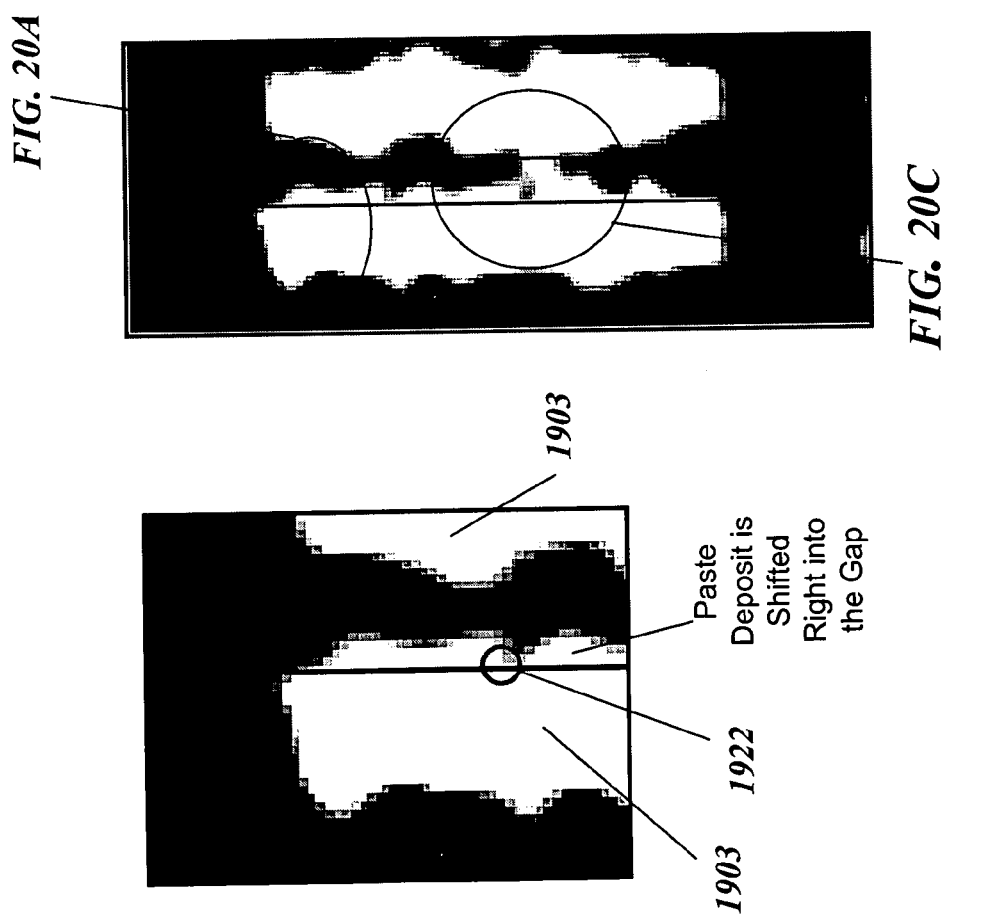
FIG. 20A
FIG. 20B
FIG. 20C

36% Weighted Paste Coverage in Gap

SYSTEMS AND METHODS FOR DETECTING DEFECTS IN PRINTED SOLDER PASTE

CLAIM OF PRIORITY

This application is a continuation-in-part of U.S. patent application Ser. No. 10/734,395, filed Dec. 12, 2003 now U.S. Pat. No. 6,891,967, which is a continuation-in-part of U.S. patent application Ser. No. 09/304,699, entitled "A Method and Apparatus for Inspecting Solder Paste Deposits on Substrates", filed May 4, 1999 now U.S. Pat. No. 6,738,505, the contents of each of which are incorporated herein by reference in their entirety.

FIELD OF THE INVENTION

Embodiments of the invention generally relate to devices, systems, and methods used in machine vision systems. More particularly, the invention relates to systems and methods for detecting defects in the solder paste print process.

BACKGROUND OF THE INVENTION

In typical surface-mount circuit board manufacturing operations, a stencil printer is used to print solder paste onto a circuit board. Typically, a circuit board having a pattern of pads or some other, usually conductive, surface onto which solder paste will be deposited is automatically fed into the stencil printer and one or more small holes or marks on the circuit board, called fiducials, is used to properly align the circuit board with the stencil or screen of the stencil printer prior to the printing of solder paste onto the circuit board. In some prior art systems, an optical alignment system is used to align the circuit board with the stencil. Examples of optical alignment systems for stencil printers are described in U.S. Pat. No. 5,060,063, issued Oct. 21, 1991 to Freeman, and in U.S. Pat. Re. 34,615 issued Jan. 31, 1992, also to Freeman, each of which is incorporated herein by reference.

The solder paste print operation can be a primary source of defects in surface mount assembly. Thus, processes have been developed to inspect a substrate after solder paste has been deposited thereon to determine whether the solder paste has been properly applied to conductive pads located on the substrate, usually, but not limited to, conduction pads on a printed circuit board. For example, in some prior art systems, the optical alignment system mentioned above also includes a vision inspection system to inspect the substrate.

Automated machine-based techniques for assessing print defects, however, are only able to isolate and quantify tangible characteristics. Reliable methods are still needed to classify and weigh the significance of print defects as they relate to the process, to provide meaningful output and to define realistic and useful process limits. Although subsequent processes certainly play a part in determining the quality of the final printed circuit board (PCB assembly), detection and accurate assessment of bridge and other defects, as printed, can provide the most direct feedback for process control of appropriate print functions.

SUMMARY OF THE INVENTION

The existence of solder paste spanning a gap between adjacent pads, by itself, does not guarantee that a bridge-related defect will occur later in the assembly process. Not all bridges or bridge-like defects have the necessary mass or geometry to adversely affect a given process. Conversely, gap defects that actually are significant to a process may not always connect adjacent pads to form a well-defined bridge. It has been found that the significance of paste-in-gap defects is affected by factors such as the total amount of paste forming a bridge or "bridge-like" feature, the geometry of a paste feature (e.g., length, width, proportions), and the total amount of paste in a gap, regardless of its geometry.

In at least one embodiment, the invention provides systems and methods that can provide improved detection of solder paste defects such as bridges, to improve print process control. In this embodiment, the systems and methods of the invention operate on a premise that not all bridge or "bridge-like" defects have the necessary mass or geometry to adversely affect a given process, and gap defects that are significant don't always connect adjacent pads to form a bridge. Although subsequent processes also play a part in determining the quality of the final assembly, detection and accurate assessment of bridge and other defects, as printed, can, in at least one embodiment, provide direct feedback for process control of appropriate print functions.

In one embodiment, the invention provides a method for analyzing gap defects that provides reliable measurements of paste-in-gap area (length times width) and detects significant geometry and span of bridge-like paste features as they relate to the SMT (surface mount technology) assembly process. The total amount of paste in a gap and the effective span of bridge-like features across the gap are used together to determine the probability that a specific paste feature will cause a bridge-related defect.

In one embodiment the invention is directed to a method of analyzing an image of a substance deposited onto a substrate, the image comprising a plurality of pixels. The method includes defining a region of interest in the image, associating the region of interest with first and second perpendicular axis, wherein a set of pixels in the image lie along the first axis, converting the pixels in the region of interest to a single dimensional array aligned with the first axis and projecting along the second axis, and applying at least one threshold to the single dimensional array, the threshold based at least in part on a predetermined limit.

Embodiments of the invention can include one or more of the following features. The method can include smoothing the single dimensional array. The method can further include the steps of computing, for each pixel along the first axis, a sum of all the pixels in the region of interest that are in perpendicular alignment with the respective pixel along the axis, and representing the sums of each pixel along the axis as a single dimensional array perpendicular to the second axis.

Embodiments of the invention can further include the steps of locating an axis substantially near one edge of the region of interest, wherein a set of pixels in the image lie along the axis and evaluating the single dimensional array to determine whether any features exist in the region of interest. The features can include defects, short circuits, bridge-like features, bridges, excess quantities of the substance, stray areas of the substance, and poorly defined areas of the substance.

Other embodiments of the method of the invention include receiving at least one detection parameter, the detection parameter relating to determining the likelihood that the at least one feature in the image could later result in a functional defect. The step of evaluating can be accomplished in accordance with the at least one detection parameter. A further embodiment of the invention can include computing, for each feature in the region of interest, the area and geometry of the feature, the computation accomplished at least in part using the detection parameter and the single dimensional array. Still further embodiments can include the step of determining, based on the area and geometry, the likelihood that the at least one feature in the image could later result in a functional defect.

Embodiments of the invention can include stencils as the substrates and an electrical material as the substance. Other embodiments of the invention can include a substance that comprises solder paste. The image can be comprised of a digitized image.

Implementations of the invention can include a method of inspecting a stencil through which a substance is deposited onto an electronic substrate. The method includes depositing the substance through the stencil onto the substrate, capturing an image of the stencil and of the substrate, detecting variations in texture in the image to determine a location of the substance on the stencil and on the substrate, defining a region of interest in the image, the defined region of interest having a first axis, wherein a set of pixels in the image lie along the axis, computing, for each pixel along the axis, a sum of all the pixels in the region of interest that are in perpendicular alignment with the respective pixel along the axis, representing the sums of each pixel along the axis as a single dimensional array perpendicular to the axis, and evaluating the single dimensional array to determine whether any features exist in the region of interest.

Other implementations of the invention include a system for dispensing solder paste at predetermined locations on a substrate. The method comprises a dispenser that dispenses material on the substrate, a controller for maintaining the operations of the dispenser, and a processor in electrical communication with the controller of the processor. The processor is programmed to perform texture-based recognition of a solder paste deposit located on the substrate, define a region of interest within the image of solder paste, the defined region of interest having a first axis, wherein a set of pixels in the image lie along the axis, compute, for each pixel along the axis, a sum of all the pixels in the region of interest that are in perpendicular alignment with the respective pixel along the axis, represent the sums of each pixel along the axis as a single dimensional array perpendicular to the axis, and evaluate the single dimensional array to determine whether any defects exist in the region of interest.

Still further implementations of the invention are directed to a method of detecting a defect in a substance deposited on a substrate. The method includes capturing an image of the substrate, detecting variations in texture in the image to determine a location of the substance on the substrate, defining a region of interest in the image, the defined region of interest having a first axis, wherein a set of pixels in the image lie along the axis, computing, for each pixel along the axis, a sum of all the pixels in the region of interest that are in perpendicular alignment with the respective pixel along the axis, representing the sums of each pixel along the axis as a single dimensional array perpendicular to the axis, and evaluating the single dimensional array to determine whether any defects exist in the region of interest.

Embodiments of the invention can include one or more of the following features. The substance can be solder paste. The defect can comprise at least one of a solder bridge, bridge-like feature, or excess paste feature. The substrate can include first and second pads onto which the solder is deposited and the defect can comprise the existence of solder paste spanning at least a portion of the distance between the first and second pads. The method can further comprise applying a rule to determine whether the defect should be classified as a solder bridge.

Details relating to this and other embodiments of the invention are described more fully herein.

BRIEF DESCRIPTION OF THE FIGURES

The advantages and aspects of the present invention will be more fully understood in conjunction with the following detailed description and accompanying drawings, wherein:

FIGS. 5A–5C is a representation of various filters typically used in the method of the invention;

FIGS. 8A–8H is a schematic of various kernel configuration options for paste texture spacing versus magnification;

FIGS. 10A–10C is a comparison of raw images from a system that utilizes an embodiment of the invention without saturation;

FIGS. 20A–20C are details of a paste-only image of the respective images in FIGS. 19A–19C;

FIGS. 23A–23C are first illustrative run-time, paste-only, and projected paste only images of solder paste in a gap, processed in accordance with an embodiment of the invention;

The drawings are not necessarily to scale, emphasis instead generally being placed upon illustrating the principles of the invention.

DETAILED DESCRIPTION

Figure 1A:
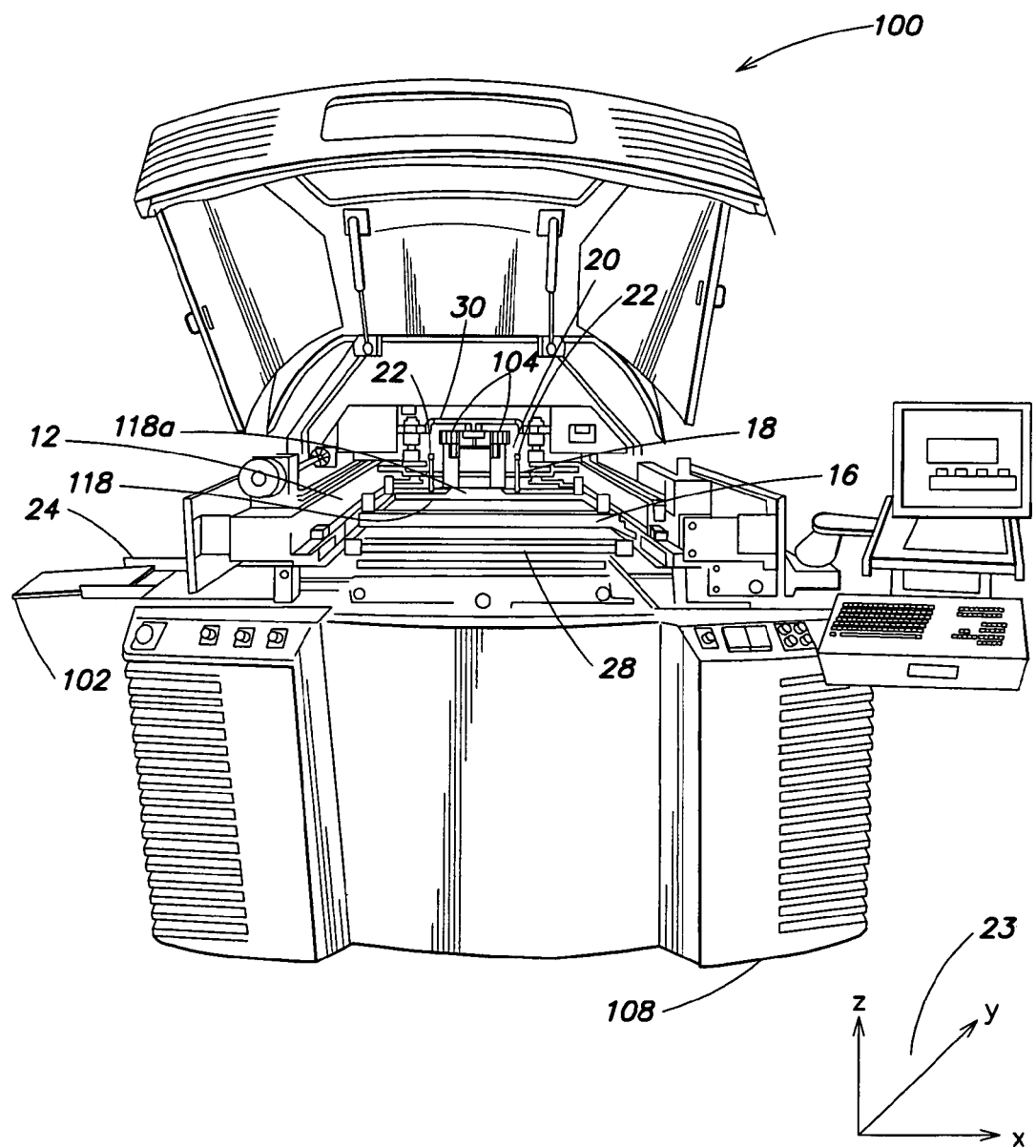
FIG. 1A provides a front view of a stencil printer in accordance with one embodiment of the present invention.

One embodiment of the present invention generally relates to a stencil printer utilizing a method for conducting solder paste texture recognition. This technique is used to acquire paste-only images of printed substrates, such as stencils and circuit boards, for use in analyzing and thereafter preventing defects. For example, print defects often occur in the process of printing solder paste on a circuit board using a stencil printer. FIG. 1A shows a front view of a stencil printer 100 in accordance with one embodiment of the present invention. The stencil printer 100 includes a frame 12 that supports components of the stencil printer including a controller 108, a stencil 16, and a dispensing head 118 having a dispensing slot 118a from which solder paste may be dispensed.

The dispensing head 118 is coupled to a first plate 18 using two thumbscrews 22. The first plate 18 is coupled to a second plate 20 which is coupled to the frame 12 of the stencil printer 10. The first plate 18 is coupled to the second plate 20 in such a manner that the first plate can be moved with respect to the second plate along a z-axis, the z-axis being defined by the coordinate axis system 23 shown in FIG. 1A. The first plate is moved by motors under the control of the controller 108.

The second plate 20 is movably coupled to the frame 12 such that the second plate 20 can move with respect to the frame 12 along an x-axis, the x-axis also being defined by the coordinate axis system 23. As described below, the movements of the first and second plates allow the dispensing head 118 to be placed over the stencil 16 and moved across the stencil to allow printing of solder paste onto a circuit board.

Stencil printer 100 also includes a conveyor system having rails 24 for transporting a circuit board 102 to a printing position in the stencil printer. The stencil printer has a number of pins 28, positioned beneath the circuit board when the circuit board is in the dispensing position. The pins are used to raise the circuit board 102 off of the rails 24 to place the circuit board in contact with, or in close proximity to, the stencil 16 when printing is to occur.

The dispensing head 118 is configured to receive two standard SEMCO three ounce or six ounce solder paste cartridges 104 that provide solder paste to the dispensing head 118 during a printing operation. Each of the solder paste cartridges 104 is coupled to one end of a pneumatic air hose 30. As readily understood by those skilled in the art, the dispensing head could be adapted to receive other standard, or non-standard, cartridges. The other end of each of the pneumatic air hoses is attached to a compressor that under the control of the controller 108 provides pressurized air to the cartridges to force solder paste to flow from the cartridges into the dispense head 118 and onto the screen 16. Mechanical devices, such as a piston, may be used in addition to, or in place of, air pressure to force the solder paste from the SEMCO cartridges into the dispensing head.

In one embodiment of the present invention, the controller 108 is implemented using a personal computer using the Microsoft DOS or Windows® NT operating system with application specific software to control the operation of the stencil printer as described herein.

The stencil printer 100 operates as follows. A circuit board 102 is loaded into the stencil printer using the conveyor rails 24. A machine vision process for automatically aligning the printed circuit board 102 to stencil 16 is implemented. The printed circuit board 102 and stencil 16 are brought into contact, or nearly so, prior to application of the solder paste. The dispensing head 118 is then lowered in the z-direction until it is in contact with the stencil 16. Pressurized air is provided to the cartridges 104 while the dispensing head is moved in the x direction across the stencil 16. The pressurized air forces solder paste out the cartridges and creates pressure on the solder paste in the dispensing head forcing solder paste from the dispensing slot 118a of the dispensing head 118 through apertures in the stencil 16 and onto the circuit board 102. Once the dispensing head 118 has fully traversed the stencil 16, the circuit board 102 is lowered back onto the conveyor rails 24 and transported from the printer so that a second circuit board may be loaded into the printer. To print on the second circuit board 102, the dispensing head 118 is moved across the stencil in the direction opposite to that used for the first circuit board. Alternatively, a squeegee arm could swing in to contain the solder paste in the dispenser, and the dispenser can then be lifted in the z-direction and moved back to its original position to prepare to print on the second circuit board using a similar direction stroke.

As described further in U.S. Pat. No. 6,324,973 entitled "Method and Apparatus for Dispensing Material in a Printer" filed on Jan. 21, 1999, assigned to Speedline Technologies, Inc., the assignee of the present invention and incorporated herein by reference, the dispensing head 118 is lowered into a printing position so that it is in contact with the stencil. The stencil printer 100 operates by forcing solder paste from the dispensing head 118 onto the stencil using air pressure applied to each of the SEMCO cartridges as the dispensing head moves across the stencil. In the printing position, two blades (not shown) come into contact with the top surface of the stencil. For each direction that the dispensing head moves across the stencil, one of the blades will be a trailing blade and will scrape any excess solder paste off the stencil.

At the conclusion of printing, when it is desired to lift the dispensing head 118 off of the stencil, the controller 108 turns off the pressurized air source, prior to lifting the dispensing head 118. This causes the solder paste to remain in a chamber (not shown) when the dispensing head 118 is lifted and effectively reduces the amount of solder paste that is left on the stencil when printing is complete.

After the solder paste has been deposited onto the printed circuit board, a machine vision process for automatically inspecting the printed circuit board is implemented. In one embodiment of the present invention, the inspection process uses a texture recognition method to determine whether solder paste has been properly deposited onto predetermined contact regions located on the printed circuit board. The solder paste texture recognition system used in embodiments of the present invention will now be described.

Figure 1B:
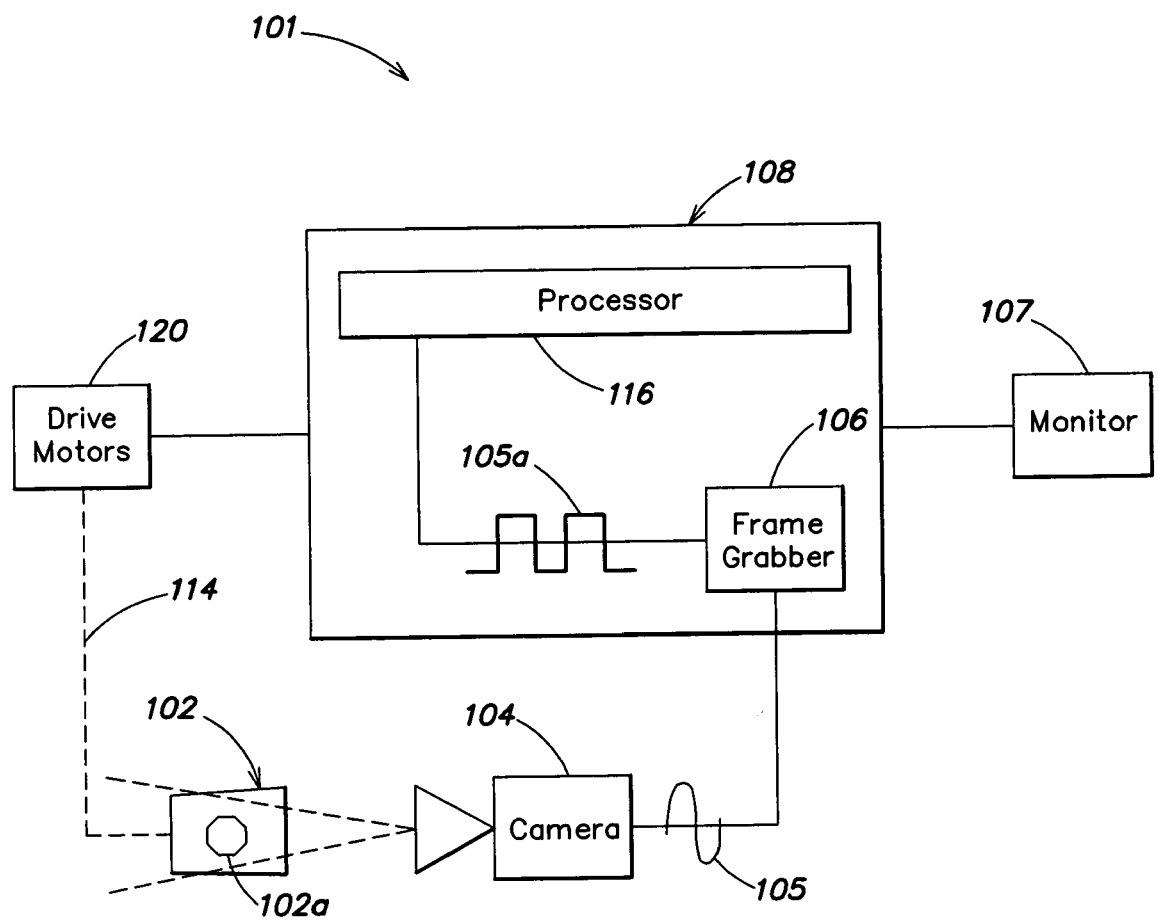
FIG. 1B is a schematic of another embodiment of the present invention.

Referring to FIG. 1B, a functional block diagram 101 of the screen printer 100 is shown. In FIG. 1B, the screen printer 100 is shown inspecting a substrate 102 having a substance 102a deposited thereon. In one embodiment, the substrate 102 includes a printed circuit board, stencil, wafer, or any flat surface, and the substance 102a includes solder paste.

Figure 2A:
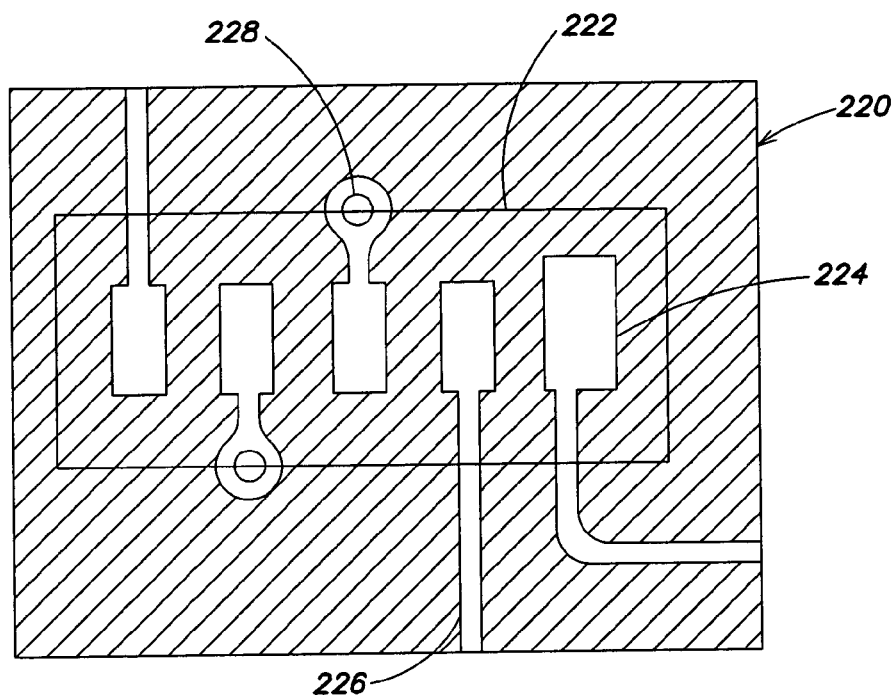
FIGS. 2A–2B is a schematic of a printed circuit board.
Figure 2B:
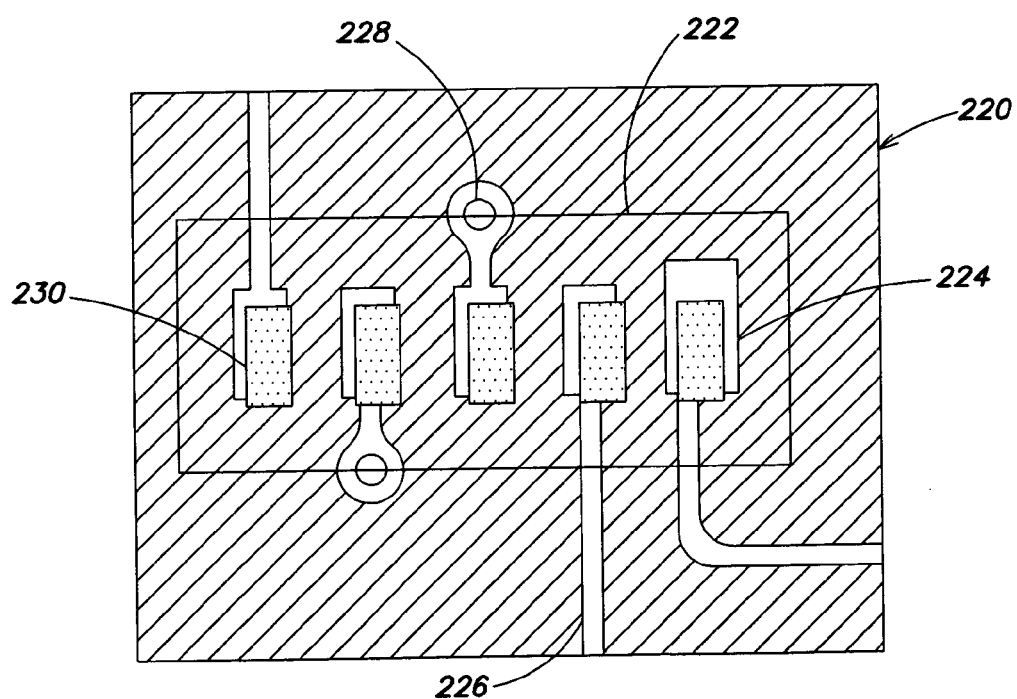

FIG. 2A and FIG. 2B, show a top plan view of a printed circuit board 220 which may be used in place of the substrate 102 in FIG. 1B. The printed circuit board 220 has a region of interest 222 and contact regions 224. It also has traces 226 and vias 228. FIG. 2A shows the printed circuit board 220 without solder paste deposits on any of the contact regions 224. FIG. 2B shows solder paste deposits 230 distributed on the predetermined contact regions 224 of the printed circuit board 220. In the printed circuit board 220, the predetermined areas 224 are distributed across a designated region of interest 222 of the printed circuit board 220.

FIG. 2B shows a misalignment of the solder paste deposits 230 with contact pads 224. Each of the solder paste deposits 230 is partially touching one of the contact regions. However, to insure good electrical contact and prevent bridging between pad regions (i.e. short circuits), solder paste deposits 230 should be aligned to contact pad regions 224 within specific tolerances. An embodiment of the invention described herein discloses a method using texture recognition to detect misaligned solder paste deposit on contact pads, and as a result, generally improves the manufacturing yield of printed circuit boards.

Figure 2C:
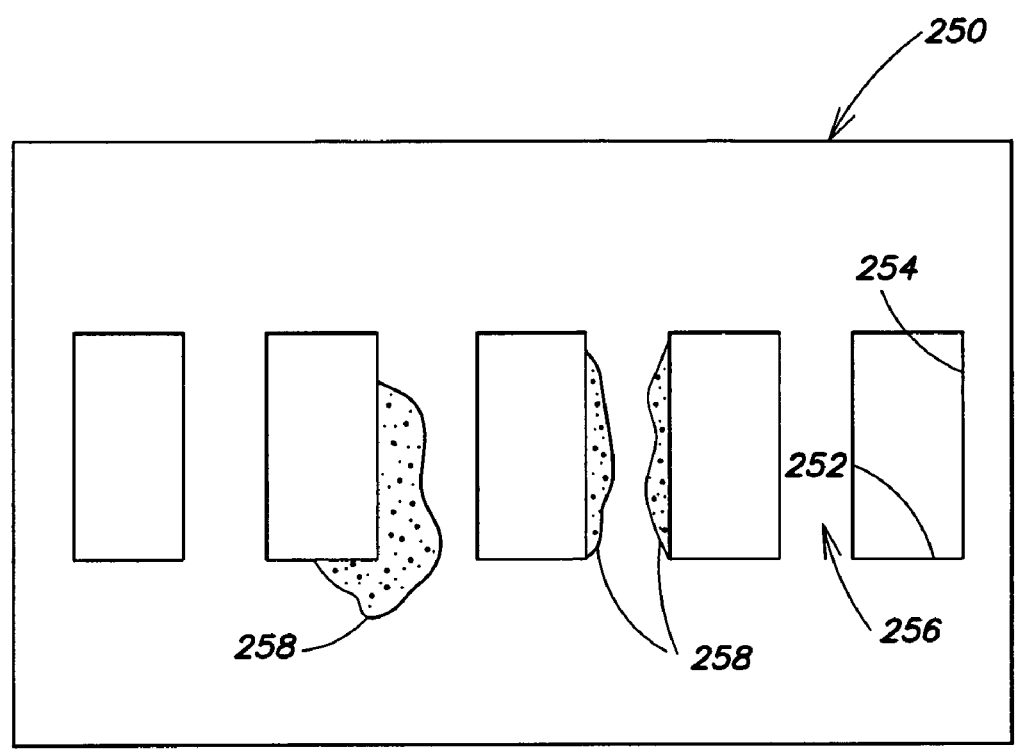
FIG. 2C is a schematic of a stencil used in printing circuit boards.

Referring to FIG. 2C, a top plan view of a stencil is shown. The stencil 250 may also represent the substrate 102 which requires inspection, as depicted in FIG. 1B. The stencil 250 includes apertures 252 through which solder paste is deposited onto the printed circuit board. Apertures 252 can be substantially small in size depending on the circuit board requiring printing. Solder paste 258 deposited through the apertures often becomes lodged on the sides 254 or surrounding area 256 of the apertures 252 during a single printing cycle or repetitive printing cycles. Thus, both the position of the stencil and the size of the apertures in the stencil may contribute to solder paste getting lodged in the apertures. It may be necessary, therefore, to inspect the solder paste deposits on both the stencil and on the printed circuit board to reliably detect defects associated with the printing operation.

Again referring to FIG. 1B, in one embodiment of the present invention, a method for solder paste texture recognition includes a step of using a camera 104 to capture an image of the substrate 102 having a substance 102a deposited thereon. In one embodiment, the camera 104 is a charge-coupled device that transmits a real-time analog signal 105 to a frame grabber 106. The real-time analog signal corresponds to an image of the substrate 102 having the substance 102a deposited thereon. The camera 104 may obtain an image of the substance 102a using a raster type scan, or an area scan of the substrate 102. In one embodiment, the camera 104 is also able to image the bottom side of the substrate 102 or stencil 16 by using a combination of mirrors, beam splitters, or another camera.

The camera 104 transmits an analog signal 105 to a frame grabber 106. The analog signal 105 contains information regarding the image of the substrate 102 and the substance 102a deposited thereon. The frame grabber 106 digitizes the analog signal 105 and creates a digitized image 105a which may be displayed on a monitor 107. The digitized image 105a is divided into a predetermined number of pixels, each having a brightness value from 0 to 255 gray levels (in an 8-bit range). In one embodiment of the invention, the analog signal 105 represents a real-time image signal of the substrate 102 and substance 102a deposited thereon. However, in an alternative embodiment, a stored image is transmitted from a memory device coupled to a controller 108. Furthermore, depending upon the camera 104, and other devices used to acquire the image of the substrate 102 and the substance 102a, the brightness values used could range from 0 to 65,535 gray levels (in a 16-bit range).

The frame grabber 106 is electrically connected to the processor 116. The controller 108 includes a processor 116 and the frame grabber 106. The processor 116 calculates statistical variations in texture in the image 105a of the substance 102a. The texture variations in the image 105a of the substance 102a are calculated independent of relative brightness of non-substance background features on the substrate 102, so that the processor 116 can determine the location of the substance 102a on the substrate 102, and to compare the location of the substance 102a with a desired location. In one embodiment of the present invention, if the comparison between the desired location and the actual location of the substance 102a reveals misalignment exceeding a predefined threshold, the processor 116 responds with adaptive measures to reduce or eliminate the error, and may reject the substrate or trigger an alarm via the controller 108. The controller 108 is electrically connected to the drive motors 120 of the stencil printer 100 to facilitate alignment of the stencil and substrate as well as other motion related to the printing process.

The controller 108 is part of a control loop 114 that includes the drive motors 120 of the stencil printer 100, the camera 104, the frame grabber 106, and the processor 116. The controller 108 sends a signal to adjust the alignment of a stencil printer frame 12, and thus the mechanically coupled stencil 16, should the substance 102a on the substrate 102 be misaligned.

Figure 3:
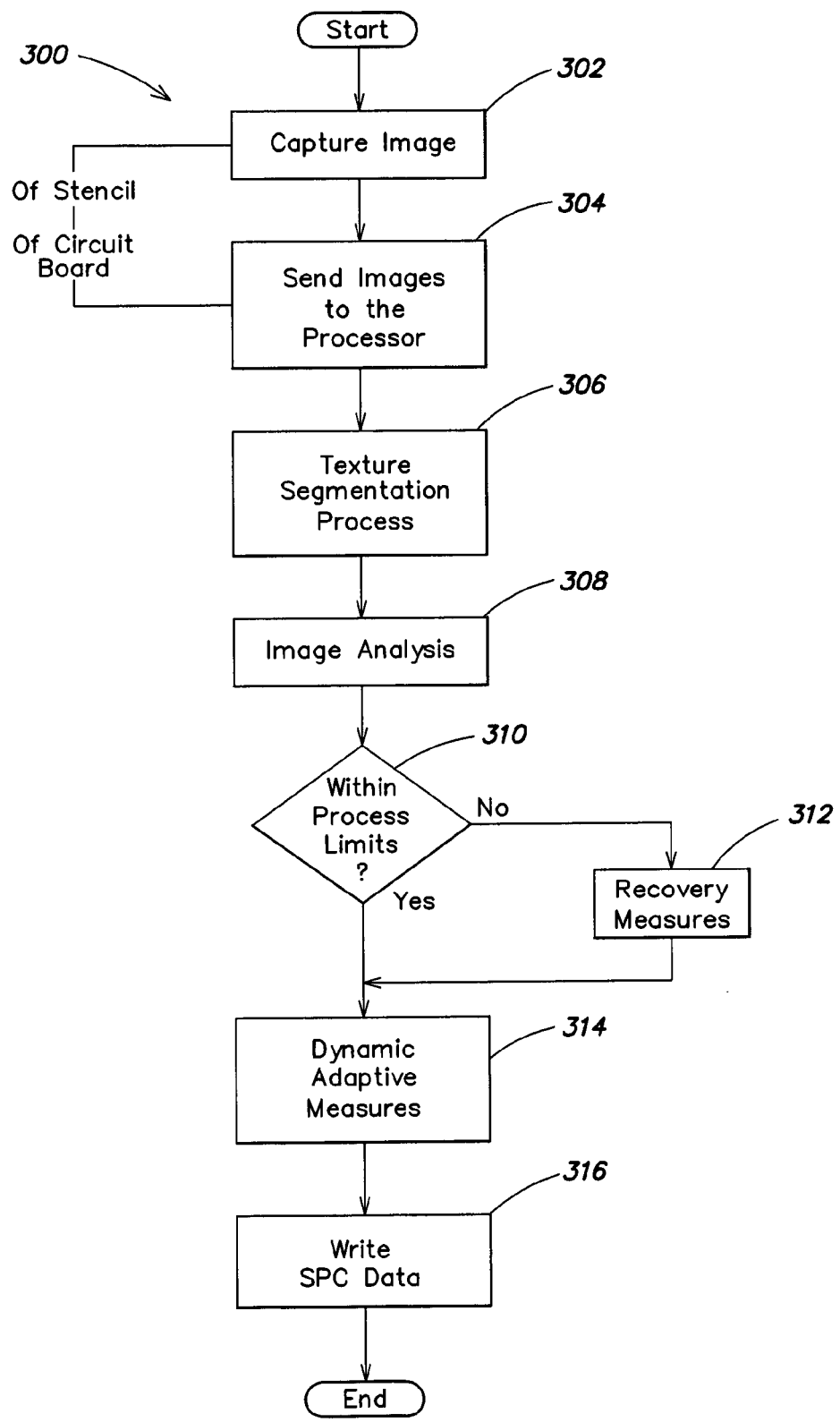
FIG. 3 is a flowchart of the method for inspecting solder paste deposits on a substrate.

The method of capturing an image is substantially the same for inspecting both the circuit board and the stencil. FIG. 3 shows a flowchart 300 of the method for inspecting solder paste deposits on a substrate. Step 302 includes capturing an image 105 of a substance deposited onto a substrate 102. In one embodiment, the substance 102a is solder paste and the substrate 102 is a printed circuit board. The image 105a of the substrate 102 with a substance 102a deposited thereon may be captured in real-time or retrieved from a computer memory. Step 304 includes sending the image 105a to a processor 116. The remaining steps in the inspection method are performed by the processor 116. Step 306 detects texture variations in the image 105a utilizing various texture sensitive operators described below. The texture variations are used to determine the location of the substance 102a on the substrate 102. In Step 308, the processor 116 is programmed to compare the texture variations at a particular location with texture features at predetermined locations of the substrate. In Step 310, if the variations are within predetermined limits, the processor 116 may respond with dynamic adaptive measures (Step 314) to refine the main process. If the variations lie outside predetermined limits, then Step 314 triggers appropriate recovery measures through Step 312 to reject the substrate, terminate the process, or trigger an alarm via controller 108. Related statistical process control (SPC) data are recorded in step 316 along with other process data and is available for review and analysis both locally and via network access.

Figure 2D:
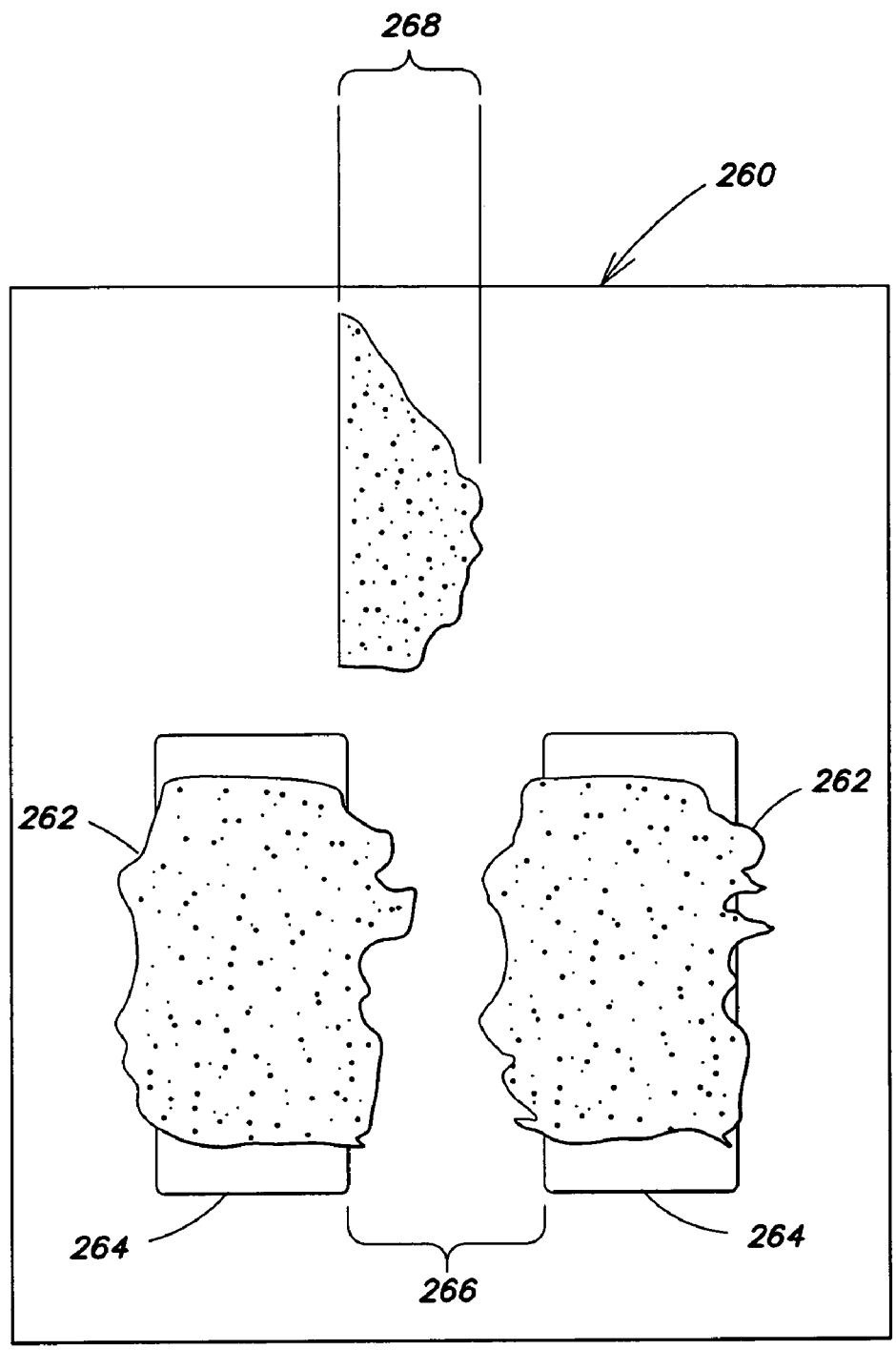
FIG. 2D is a schematic of a printed circuit board.

For example, as mentioned, the substrate 102 can be a circuit board on which texture recognition is performed. With detection of the solder paste on a circuit board portion 260, a measurement of the bridge that occurs in a gap between two pads is made. Referring to FIG. 2D, the solder paste 262 is deposited on a pad 264, the gap between adjacent pads 264 being identified by reference number 266. The solder paste 262 on both sides of a gap 268 is summed along a single axis to determine the maximum span of each bridge. With continued reference to FIG. 2D, and referring to FIG. 2F, the texture based solder paste recognition method is also used to detect paste on a stencil portion 270 so that a correlation can be made between the first measurement of the span 268 of the bridges on the circuit board and a second measurement of the gap on the stencil. Solder paste 262 is detected both in stencil apertures 272 and in the space between two adjacent apertures, referred to herein as the stencil gap 274. The maximum amount of solder paste 262 detected in the stencil gap 274 is correlated to the maximum bridge span 268 on the circuit board, allowing a prevention mechanism to be implemented based on detection of solder paste on the stencil.

Figure 2E:
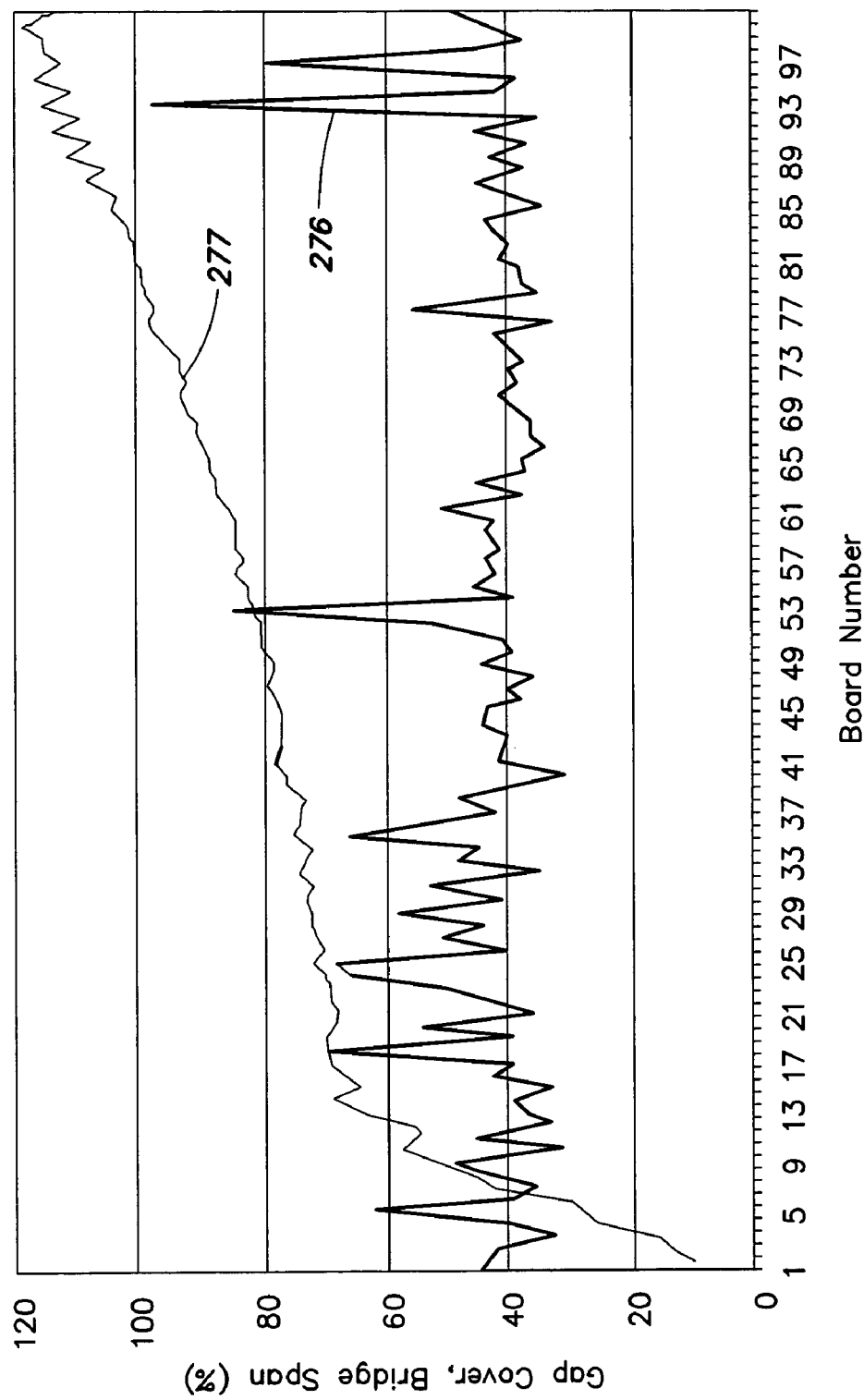
FIG. 2E is a representation of experimental results from a system without a bridge prevention technique of one embodiment of the invention.
Figure 2F:
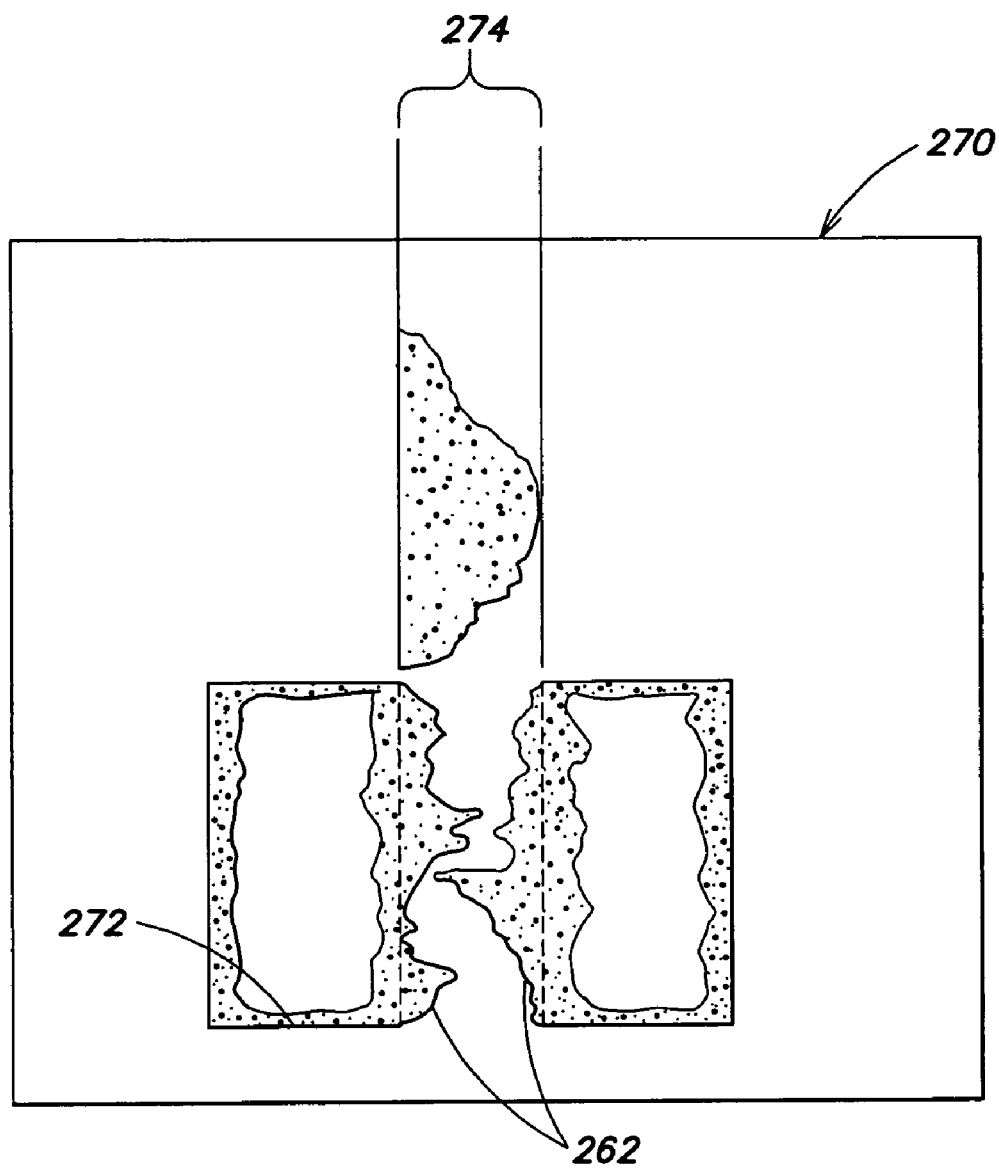
FIG. 2F is a schematic of a stencil having solder paste deposits.
Figure 2G:
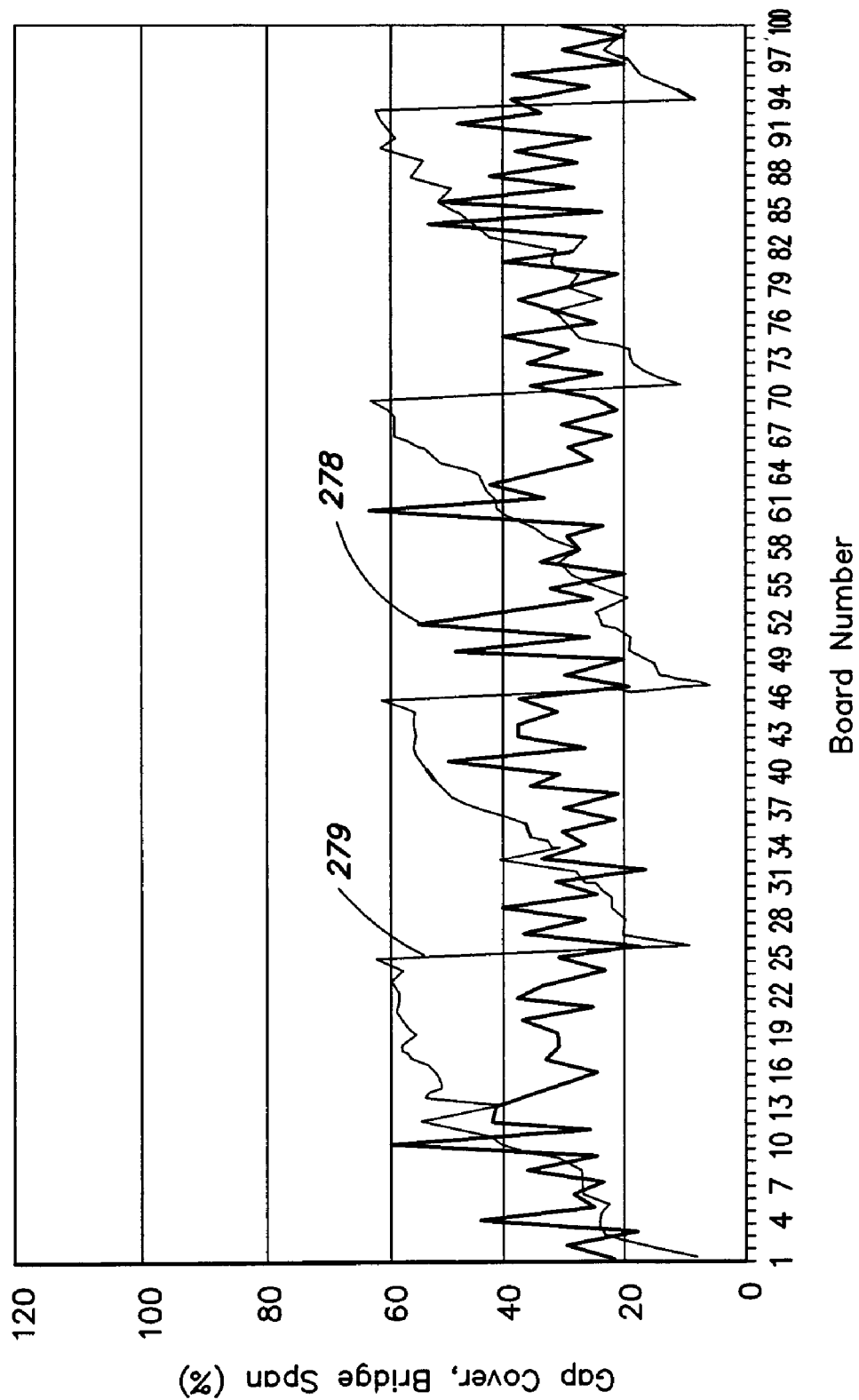
FIG. 2G is a representation of experimental results from a system utilizing the bridge prevention technique of one embodiment of the invention.

Referring to FIG. 2E, when the paste contamination on the stencil exceeds the maximum gap cover on the stencil, bridge-like features appear on the circuit board. This is represented by line 276 having sharp peaks crossing the 80% limit in FIG. 2E. The maximum gap cover of the stencil is represented by line 277 in FIG. 2E. Based on this occurrence, a threshold level of contamination is set, such that when contamination of the stencil reaches the threshold level, a wipe or other cleaning process of the stencil is triggered, preventing the formation of large bridges on the surface of the circuit board. As shown in FIG. 2G, bridges are avoided when the stencil is cleaned, resulting in no peaks of line 278 reaching at or near 80%. The maximum gap cover of the stencil is represented by line 279. Thus, texture based solder paste recognition techniques are used to detect solder paste on the circuit board 220 and on the stencil 250, and by detecting deposits of solder paste on the circuit board and the stencil, general improvements are made to the manufacturing yield of printed circuit boards.

As mentioned above, detecting the variations of texture in the image 105a, and comparing the location and area of the substance 102a with a predetermined location and area (where area is a length by width measurement of the substance), utilizes a processor 116.

Processor Functions

The technique used by the processor 116 to recognize solder paste 228 on a printed circuit board 224 and on a stencil 250 will now be described. In one embodiment of the present invention, the processor 116 performs four functions. The four functions are image enhancement, texture segmentation, image location analysis, and process control.

As previously stated, existing solder paste inspection systems primarily use basic single or dual thresholding methods that only utilize differences in pixel brightness of the original image to identify solder paste. In embodiments of the invention, the processor 116 also utilizes single and dual thresholding techniques but on an image that is preprocessed using various texture sensitive operators such that single and dual thresholds may be used to separate specific regions based on relative texture, as in this case, to identify the location and area of solder paste deposits. The dual threshold technique is preferred since it provides a more accurate scalable transition at edge pixels or any region of uncertainty in the texture based image.

The texture sensitive operators utilized by the method of the invention include a sharpening operator, a Laplacian operator, and a smoothing operator that includes a boosting mechanism. Each of the operators will be described as part of the processor functions.

Texture is a variation of brightness. In particular, texture refers to the local variation in brightness from one pixel to another. Thus, if brightness is interpreted as the elevation in an image, then the texture is a measure of surface roughness.

In one embodiment of the present invention, a range operator may be used to detect texture in image 105a. The range operator represents the difference between maximum and minimum brightness values in a neighborhood. The range operator converts the original image 105a to one in which brightness represents the texture. Specifically, the original brightness features disappear and different structural regions are distinguished by the range brightness. The range operator may also be used to define edge boundaries of an image.

Another texture operator is represented by the variance in neighborhood regions. In one embodiment of the invention, the processor is programmed to calculate the variance. The variance is essentially the sum of squares of the difference between the brightness of a central pixel and its neighbors. If the sum of squares is first normalized by dividing by the number of pixels in the neighborhood, then this result represents the root mean square (RMS) difference of values and corresponds to the surface roughness. These texture sensitive operators and methods may be implemented using rudimentary tools provided by software suppliers to effectuate machine vision processes. These processes are generally discussed by John C. Russ in "The Image Processing Handbook, Second Edition", and in the "Handbook of Computer Vision Algorithms in Image Algebra", by Gerhard X. Ritter and Joseph N. Wilson which are incorporated herein by reference.

Figure 4A:
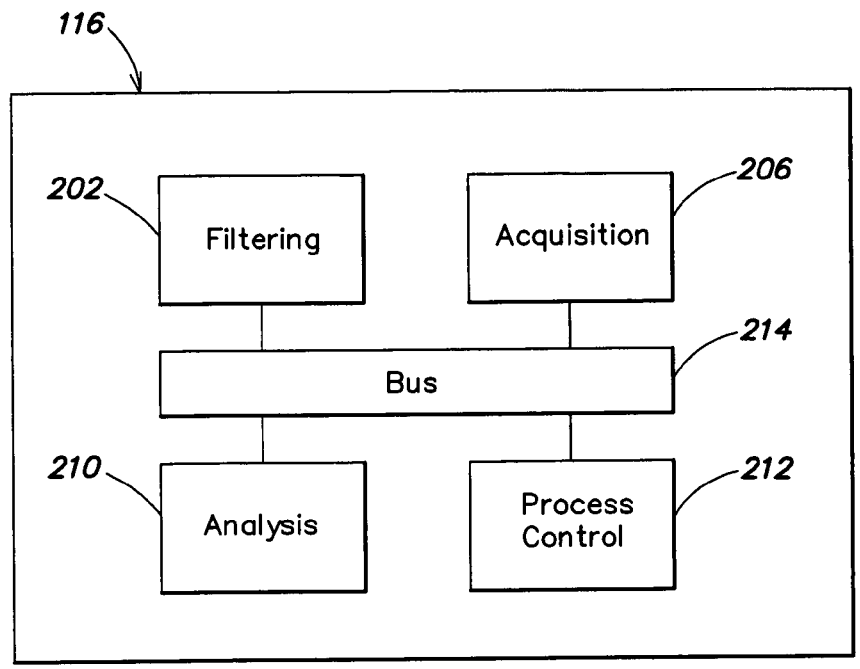
FIGS. 4A–4B is a schematic of various regions within a processor that utilizes the method of the invention.

In one embodiment of the invention, the processor 116 is programmed to perform separate functions using the aforementioned texture sensitive operators. The operations performed by the processor 116 are logically represented in a functional block diagram shown in FIG. 4A, wherein the separate operations are shown connected by an information bus 214 which facilitates sharing data between the functional blocks. The filtering section 202 of the processor 116 performs a texture segmentation process. The acquisition section 206 of the processor 116 calculates the gain and offset required to provide a specific contrast and brightness to enhance a run-time image 105a. The analysis section 210 of the processor 116 performs location and contour analysis of the solder paste region 102a on the substrate 102 and compares both to predetermined parameters. The process control section 212 of the processor 116 is used to minimize any aliasing in an image of the solder paste region 102a. The following is a discussion of the performance of each of the various functions of the processor 116.

The Filtering Section 202

Figure 4B:
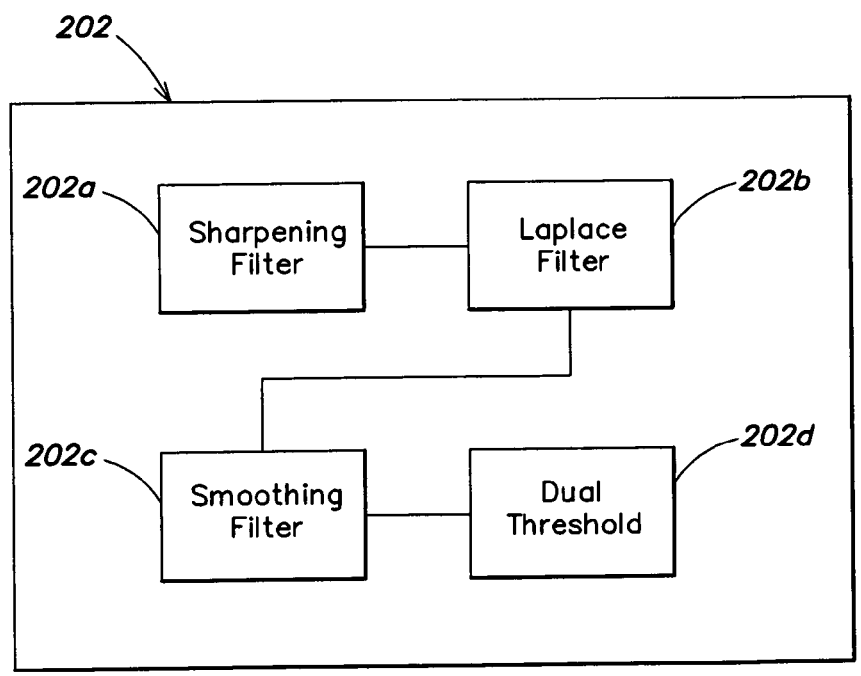

In one embodiment of the invention, the filtering section 202 of the processor 116 performs image filtering utilizing a Laplacian filter 202B shown in FIG. 4B. The Laplacian filter 202B includes Laplacian operators. The Laplacian operator is essentially an approximation to the linear second derivative of brightness. The operator highlights the points, lines and edges of an image and suppresses uniform and smoothly varying regions of the image. In one embodiment, the Laplacian operator is represented by the 3 by 3 matrix shown in FIG. 5A. The 3 by 3 matrix, referred to as a kernel, has a central pixel having a value equal to negative four which means that the brightness value of the central pixel in the image 105a is multiplied by negative four. In the Laplacian kernel, the values of the four neighbors touching the sides, above and below the central pixel is equal to one. Accordingly, the brightness levels of the four nearest neighbors to the central pixel in the image 105a are multiplied by one. Typically, the four neighbors are located using the directions north, east, south and west relative to the central pixel. However, other orientations are possible (as shown in FIGS. 8A–8H).

The specified pixels of the kernel are multiplied by the corresponding kernel coefficient and then added together. Note that, in this embodiment, the total sum of the Laplacian kernel coefficients equals zero. Consequently in a region of the image 105a that is uniform in brightness, or has a uniform gradient of brightness, the result of applying this kernel reduces the gray level to zero. However, when a discontinuity is present, e.g., a point, line or edge, the result of the Laplacian kernel may be non-zero depending upon where the central point lies on the discontinuity.

Because the image 105a can be divided into millions of pixels, and a method of the invention compares each pixel with its neighbors, processor speed may be effected. However, in an embodiment of the invention, an option is provided to increase the speed of operation of the inspection system by reducing the time to capture and process an image. Specifically, a fill-factor option may be selected to produce only a partially processed image of the substrate 102. The fill-factor is a multiplier that may be used with a subsequent blob-type operator to arrive at a calculated equivalent area of the image of the substrate 102.

The image filtering method performed by the filtering section 202 further includes a sharpening step. The sharpening step is implemented by a sharpening filter 202A shown in FIG. 4B. The sharpening filter 202A improves the image 105a by locally increasing the contrast at areas of discontinuity. The sharpening filter can be described as a specific type of Laplacian filter. As mentioned, the Laplacian operator is an approximation to the linear second derivative of the brightness (B) in directions x and y, and is represented by the equation:

$$\nabla^2 B = \partial^2 B/\partial x^2 + \partial^2 B/\partial y^2. \quad (1.0)$$

The above equation (1.0) is invariant to rotation, and hence insensitive to the direction in which the discontinuity runs. The effect of the Laplacian operator is to highlight the points, lines and edges in an image 105a and to suppress uniform and smoothly varying regions. By itself, this Laplacian image is not very easy to interpret. However, by combining the Laplacian enhancements with the original image 105a, the overall gray scale variation is restored. This technique also sharpens the image by increasing the contrast at the discontinuities.

Figures 5A, 5B, 5C:
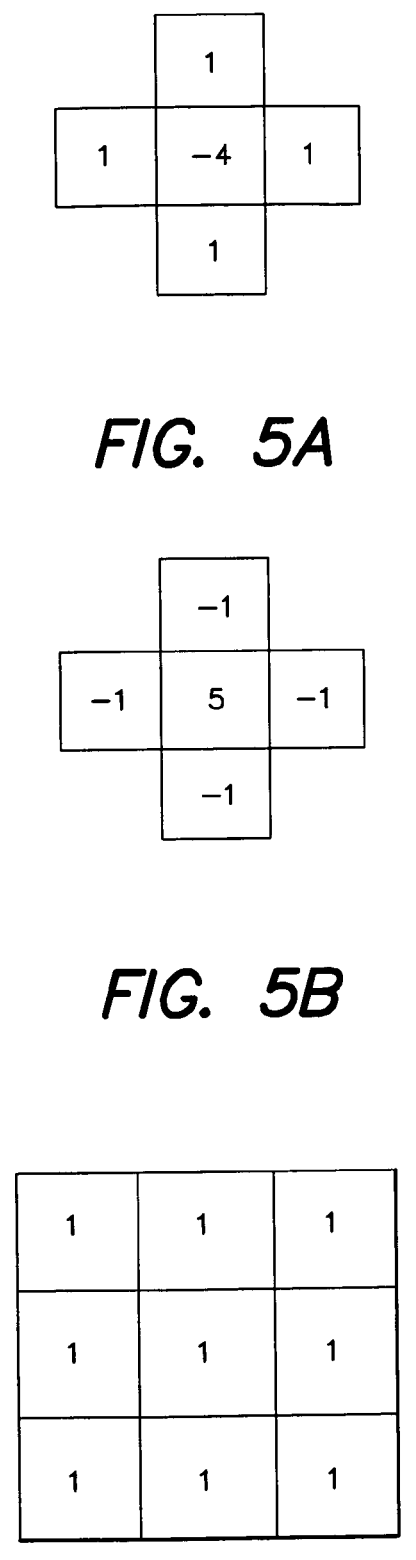

The sharpening kernel of the sharpening filter 202A used in one embodiment of the invention to locally increase the contrast is shown in FIG. 5B. Note that the central weight of the sharpening kernel has a value of five. In another embodiment of the invention, the central weight is negative five, and the north, east, south and west neighbors are multiplied by one.

The sharpening kernel, also referred to as a sharpening operator, improves the contrast produced at the edges of the image 105a. Justification for the procedure can be found in two different explanations. First, the blur in an image can be modeled as a diffusion process which obeys the partial differential equation:

$$\partial f/\partial t = \kappa \nabla^2 f, \quad (1.2)$$

where the blur function is f(x,y,t), t is time and κ is a constant. If equation (1.2) is approximated using a Taylor series expansion around time τ, then one can express the brightness of the unblurred image as $$B(x,y) = f(x,y,t) - \tau \partial f/\partial t + 0.5\tau^2 \partial^2 f/\partial t^2 - \ldots \quad (1.4)$$

If the higher order terms are ignored, then equation (1.4) becomes $$B = f - \kappa \nabla^2 f. \quad (1.6)$$

Accordingly, the brightness of the unblurred image B can be restored by subtracting the Laplacian (times a constant) from the blurred image f.

A second justification for the procedure can be found using Fourier analysis to describe the operation of the Laplacian operator as a high pass filter comprising high and low frequency components of the image brightness. In this approach, a smoothing kernel is described as a low pass filter. This low pass filter removes the high frequency variability associated with noise which can cause the nearby pixels to vary in brightness. Conversely, a high pass filter allows these high frequencies to remain (pass through the filter) while removing the low frequencies corresponding to the gradual overall variation in brightness.

Accordingly, the image filtering method performed by the filtering section 202 of the processor 116 includes a smoothing step. The smoothing step is implemented using a smoothing filter 202C shown in FIG. 4B. The smoothing filter 202C is used to reduce the signal to noise ratio associated with the image 105a. Essentially, the smoothing step performs spatial averaging. The spatial averaging adds together the pixel brightness values in each small region of the image 105a, and divides by the number of pixels in the neighborhood, and uses the resulting value to construct a new image.

In one embodiment of the invention, the smoothing operator utilized is shown in FIG. 5C. In this embodiment, the value of the central and neighboring pixels in the smoothing kernel are all equal to one. Smoothing is used here to average similarly textured regions to be separated via subsequent thresholding operations.

Smoothing operations tend to reduce the maximum values and increase minimum values in the image. Depending on the ratio of bright pixels versus dark pixels, the resulting image may brighten or darken as smoothing is applied. Performing an unlimited number of smoothing operations would ultimately result in an image with only one gray level. In this embodiment dark pixels (indicating low frequencies) are more prevalent, so instead of dividing by nine, the number of pixels used, the sum is divided by eight to effectively boost the smoothed image by a factor of 1.125 after each application or pass such that contrast and brightness is improved for subsequent thresholding operations. This also improves processing speed by allowing a relatively faster shift-by-3 (binary) operation rather than a numerically equivalent but slower division by eight. In this embodiment, the best results are typically observed after six smoothing applications, or passes, as described above.

In another embodiment of the invention, one may reduce the signal to noise ratio by performing a kernel operation. The kernel operation is spatial averaging that is performed by replacing each of the pixels with the average of itself and its neighbors. In one embodiment of the invention, a computer program performs the kernel operation and calculates the above described image morphologies using sharpening operators, Laplacian operators, and smoothing operators.

The Acquisition Section 206

In one embodiment of the invention, the processor 116 includes an acquisition section 206 that provides automatic gain and offsets (AGO) used to view or capture the image 105a. In general, any means to adjust or otherwise enhance brightness, contrast or overall quality of the real-time image 105 or stored image 105a, or portions of the image 105a may be applied. Such enhancements may include, but are not limited to, lighting configurations, utilizing optical filters, spatial filters, polarizers, or any method that includes a combination thereof. The enhancements may further include software manipulation of the pixels in the image 105a to provide optical corrections to aberrations, vignetting and lighting.

Figure 6:
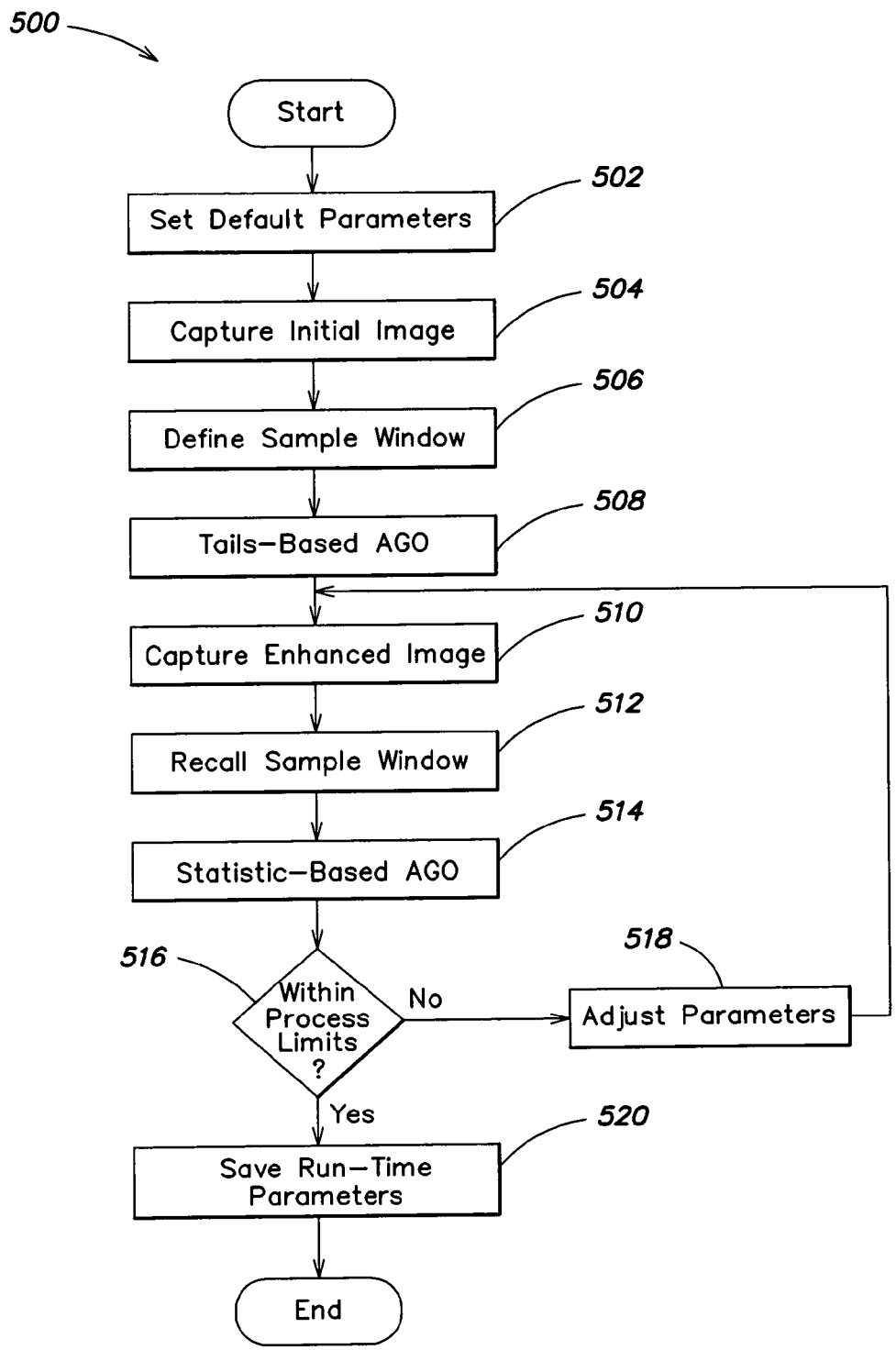
FIG. 6 is a flowchart of a method that implements an automatic gain offset feature of the invention.

FIG. 6 shows a flowchart 500 that describes the acquisition section 206 of the processor 116 in one embodiment of the invention. The steps described by the flowchart 500 may be implemented by software in the processor 116, hardware components, or a combination of hardware and software. Referring to FIG. 6, system parameters may be set manually or automatically in step 502, where the system default parameters may include the type of camera 104 being used, and the input voltages to various tail locations. Tail locations refer to the left (darkest) and right (brightest) ends, or tails, of a brightness histogram of the image 105a.

Step 504 captures the initial image 105, and a sampling window for analyzing the image is defined in Step 506. The sampling window may be manually or automatically defined and is the source of image data for the calculations performed in steps 508 and 514. Step 508 calculates the gain and offset required to move the left and right tails of the image 105a to predetermined locations. Step 510 performs a second acquisition based on information calculated in step 508 to adjust and enhance the histogram distribution of image data for subsequent operations. In one embodiment of the invention, Step 510 also performs a linear expansion and shift to further improve the image brightness and contrast of image 105a.

In one embodiment of the invention, experimental results indicate that initial limitations may be set as shown in Tables 1 and 2 below when using an 8-bit video unit a video frame grabber equipped with a typical programmable Analog to Digital Converter (ADC):

TABLE 1

Initial ADC command values for the Automatic Gain and Offset function.

| Parameter | Offset | Gain |
|---|---|---|
| Initial Command Values | 16 (for 7.5 IRE = 0) | 127 (for 100 IRE = 255) |

Table 1 shows the initial 8-bit ADC command values that typically allow the full range of standard video input levels, when digitized, to fully span the 8-bit ADC output range without clipping. Note that for a gray scale range from 0 (or 7.5 IRE) to 255 (or 100 IRE) where 100 IRE equals 0.714 volts, the initial command values for the offset and gain is 16 and 127 respectively.

Table 2 below shows the maximum and minimum range of command values used to control an input section of the ADC hardware. Also shown are adjustment limitations based on the typical signal-to-noise performance of the incoming video signal and the expected signal range.

TABLE 2

ADC command value range and limits for the Automatic Gain and Offset function.

| Parameter | Minimum | Maximum |
|---|---|---|
| Command Value Range | 0 | 255 |
| Gain Adjustment Limits | 40 (maximum gain) | 255 (minimum gain) |
| Offset Adjustment Limits | 0 (brightest offset) | 150 (darkest offset) |

Table 3 below shows typical target tail locations used by the Automatic Gain and Offset (AGO) function to determine ADC gain and offset command values that, when applied in subsequent acquisitions, tend to limit the tails of similar regions or features of interest to the target values.

TABLE 3

Initial Target Parameters for the Automatic Gain and Offset function.

| Parameter | Left Tail | Right Tail |
|---|---|---|
| Target Tail Locations for Paste Sample Window | 63 (darkest paste feature) | 191 (brightest paste feature) |
| Target Tail Locations for Full Field of View | 15 (darkest feature) | 240 (brightest feature) |

In general, the target values are selected that optimize regions or features of interest for a specific image processing task. In Step 508, tail locations 63 and 191 shown in Table 3 are used by the AGO function to enhance solder paste regions without regard to the validity of other non-paste image data. Alternatively, the tail locations 15 and 240 shown in Table 3 may be used to provide a full field of valid image data and to allow tails of subsequent acquisitions to drift slightly without loss due to clipping at each end of the 8-bit gray scale.

In one embodiment of the invention, Step 508 includes clip range detection, warning, and corrective methods for RS170/NTSC signal voltages that exceed approximately 120±3 IRE, or 0.835 to 0.878 volts. Processor 116 automatically adjusts acquisition parameters such that signal voltages remain within normal operating range.

Typical RS170/NTSC cameras have output signal clip levels set to 120±3 IRE, or approximately 0.835 to 0.878 volts, where 100 IRE equals 0.714 volts. If the voltages are over the clip range, a warning message is sent indicating that saturation has either occurred or is likely. If the voltages are below the clip range, then the method proceeds to Step 510. Step 510 administers the newly calculated parameters to acquire an enhanced image 105a for further processing. Step 512 recalls the sample window coordinates defined in Step 506 and applies them to the new image captured in Step 510. Step 514 performs a statistics-based AGO function on the new sample window to determine optimal run-time acquisition and processing parameters. This method of the invention insures that similar statistical characteristics are produced in paste regions of images that are acquired at run-time.

In Step 516, the method of the invention determines whether the preliminary run-time acquisition parameters are within predetermined hardware and software limits. Also determined in Step 516 is whether processing parameters, including kernel geometry and the effective sampling rate, are optimized to provide the maximum level of performance. If not, then the appropriate system parameters are adjusted in Step 518, and new parameters are inserted at Step 510. Steps 510 through 516 are then repeated. Once the run-time parameters are determined they are saved in memory at Step 520 and the method of the invention terminates.

Figure 7A:
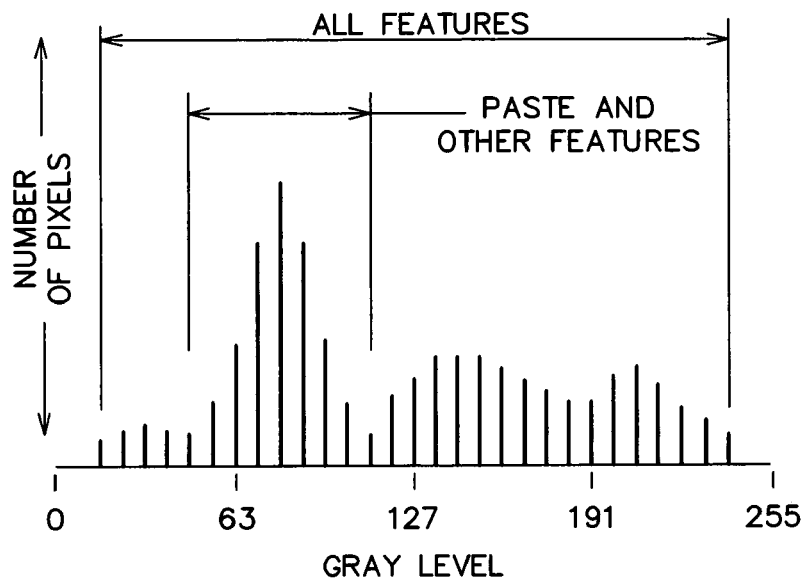
FIGS. 7A–7B is a schematic representation of solder paste distributions on a printed circuit board.
Figure 7B:
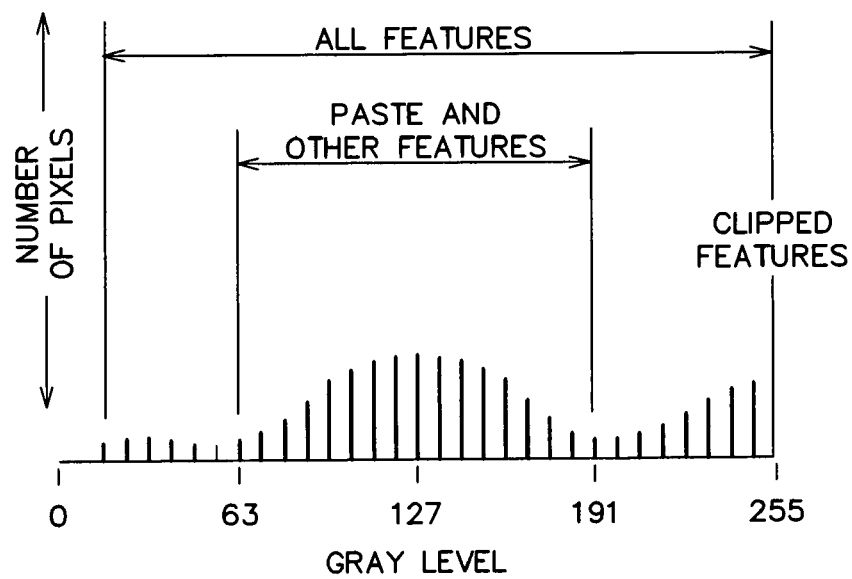
Figure 8E:
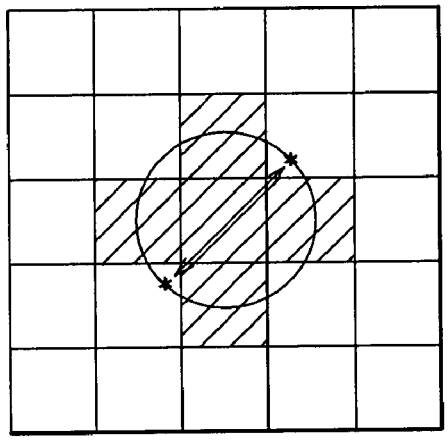
Figure 8F:
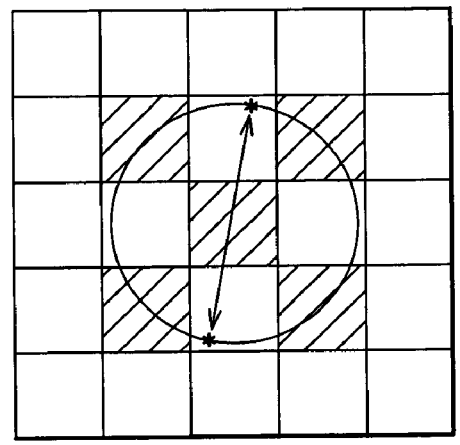
Figure 8G:
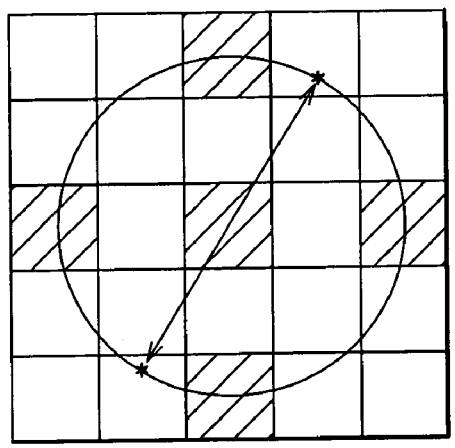
Figure 8H:
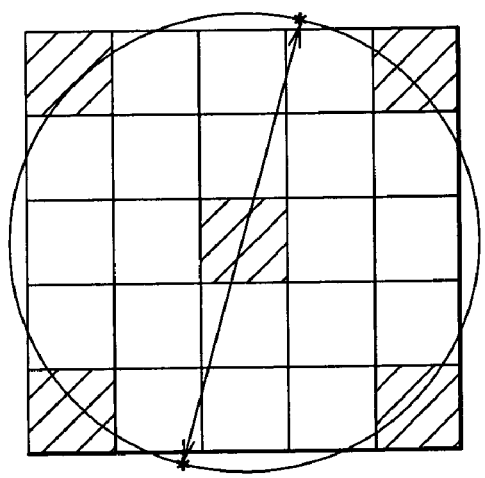

A histogram that shows the effects of the AGO in section 206 of the processor 116 is shown in FIGS. 7A–7B. Referring to FIG. 7A, a histogram of the original image of a printed circuit board 220 having solder paste 102 deposited thereon is shown. The x-axis of the histogram represents the gray levels from 0 to 255, and the y-axis represents the number of image pixels at each gray level. FIG. 7B shows a histogram of the same image with paste contrast enhanced. FIG. 7B also shows a considerable number of non-paste pixels clipped at 255. In one embodiment of the invention, the left tail of the original image equals fifteen, and the right tail equals 240 on a gray scale level that extends from 0 to 255 (implying an 8-bit gray scale). In another embodiment of the invention, Step 502 allows the processor 116 to automatically calculate and set initial acquisition parameters, or alternatively allows an operator to set the parameters. In another embodiment of the invention, the step of setting the AGO (step 502) allows an operator to manually set the acquisition parameters, or allows the processor 116 to automatically calculate and set the parameters.

As mentioned, Step 510 acquires a new image 105a to enhance the region of interest, in this case solder paste, based on parameters calculated in Step 508. In one embodiment of the invention and referring to FIG. 7B, the gray levels for the left tail and right tail of the enhanced image 105a occur at 15 and 255. In one embodiment of the invention and referring to FIG. 7B, the gray levels for the left tail and right tail of the adjusted image occur at 15 and 255 as a second pass is performed on the image 105a in step 510 to enhance the region of interest, in this case solder paste, based on parameters calculated in step 508. The calculation performed by the acquisition section 206 of the processor 116 produces a linear expansion and shift of the solder paste region such that the solder paste region of interest occurs between tails 63 and 191. FIG. 7B also shows an increased number of pixels at gray level 255 due to clipping of values that would otherwise exceed 255 when the parameters calculated in step 508 are applied.

Comparing FIG. 7A and FIG. 7B, a reduction in height of the y-axis in areas designated as paste reflects the redistribution of an equal number of paste pixels over more gray levels.

Analysis Section 210

The locator analysis section 210 of the processor 116 is used to determine the location of solder paste relative to the predetermined contact regions 224. Coordinates of each area may be determined using centroids, blob techniques, correlation, and a variety of other search tools. The process of utilizing blob techniques and centroids is well known and discussed by John C. Russ in "The Image Processing Handbook, Second Edition"; pages 416–431, 487-545, and in the "Handbook of Computer Vision Algorithms in Image Algebra", by Gerhard X. Ritter and Joseph N. Wilson; pages 161–172 which are incorporated herein by reference.

The results of the location analysis are used to detect the presence, absence, and alignment of the paste, and thus alignment of the stencil 16 with the desired contact regions 224. Results also provide the basis for other adaptive and corrective process control measures. In one embodiment of the invention, information provided by the locator section 210 is used to modify operational parameters of the dispenser head 118.

Anti-Aliasing of the Solder Paste Image (Process Control Section 212)

The process control section 212 of the processor 116 is used to minimize any aliasing in an image of the solder paste region 102a. In obtaining a digitized image 105a of the solder paste region 102a deposited on a substrate 102, several conditions unique to solder paste texture recognition are considered. Specifically, in one embodiment of the invention, the grain size of the paste and its effect on the quality of the image 105a at various magnifications. Ordinarily, as long as the sampling rate is above the Nyquist frequency aliasing may be averted. However, when imaging solder paste regions, aliasing can also occur without the proper relationships between grain size, focal length, magnification, and the CCD pixel spacing. In one embodiment, the texture recognition method of the invention considers four types of solder paste shown in Table 2 4 below.

TABLE 4

The types of solder paste used and the various grain sizes.

| Solder Paste | Nominal Grain Diameter | |
|---|---|---|
| Type 3 | 35.0 μm | 1.3780 mils |
| Type 4 | 29.0 μm | 1.1417 mils |
| Type 5 | 20.0 μm | 0.7874 mils |
| Type 6 | 10.0 μm | 0.3937 mils |

In general, different types of solder paste often vary in grain size. Table 2 4 lists the nominal grain sizes associated with the various types of solder paste. In one embodiment of the invention, the variation in grain size results in a minimum magnification with which the solder paste deposit 102a may be viewed sampled effectively by a CCD camera 104.

If a set of system magnifications (measured in microns or mils per pixel) is selected so that each of the solder paste types shown in Table 4 is sampled at the Nyquist limit, then a table of compatible magnifications can be created as shown below in Table 5.

TABLE 5

Compatible system magnifications for various types of solder paste where X indicates compatible magnification and the system magnification is shown in microns (μm) and mils per pixel (mpp).

|  | 5.0 μm 0.1969 mpp | 10.0 μm 0.3937 mpp | 14.5 μm 0.5709 mpp | 17.5 μm 0.6890 mpp |
|---|---|---|---|---|
| Type 3 | X | X | X | X |
| Type 4 | X | X | X | — |
| Type 5 | X | X | — | — |
| Type 6 | X | — | — | — |

In theory, the Nyquist limit is the highest frequency, or in this case the smallest grain size, that may be accurately sampled at a given system magnification. The Nyquist limit may be defined as half of the sampling rate.

As discussed, the method of solder paste texture recognition relies on the unique neighborhood features and statistics of solder paste that which are pronounced when the image is in sharp focus. In one embodiment of the invention, optical and imaging hardware is utilized to accurately sample the paste texture. In that embodiment, the sampling frequency of the paste particles is below the Nyquist limit of the system to avoid aliasing. Alternatively, magnification is generally limited so that the unique frequency characteristic of the solder paste is not lost, and where limited aliasing is acceptable, since the resultant characteristics of the image data, specifically in paste regions, may still be used to detect evidence of the paste.

In one embodiment of the invention, the performance of the processor 116 is optimized within an appropriate range of magnification by applying a frequency dependent kernel size and shape. Neighborhood pixels that lie an appropriate distance from the primary pixel (usually the central pixel) can manually, or automatically be selected based upon spatial frequency of the paste particles. By adjusting the geometry of the processing kernels in this manner, the effective sampling rate can be adjusted to accommodate various paste types. In one embodiment of the invention, the sensor sampling frequency is proportional to the reciprocal pixel center to center spacing measured in cycles per millimeter, and the highest frequency that may be accurately sampled is one-half the sensor sampling frequency. The magnification may also be described as a function of the pixel distribution patterns used to capture or process the image of the solder paste regions.

FIGS. 8A–8H show various pixel distribution patterns used to recognize the solder paste deposits over a region. The pixel distribution patterns represent sample kernel configurations for paste texture spacing configurations. The pixel distribution pattern used for magnification depends upon the grain size of the solder paste. In FIGS. 8A–8B and 8E-8F, the pixel distribution pattern shows the central pixels and neighboring pixels touching. In FIGS. 8C–8D and 8G–8H, the central pixels and neighboring pixels are shown separated by various distances. The distances are represented by diameters (measured in microns and mils) of a circle centered on the central pixel. The radius corresponds to the effective pixel spacing, or the sampling rate. Therefore, the diameter represents the Nyquist limit, or the minimum theoretical paste grain size that can be sampled effectively using the indicated kernel geometry. The distances are represented by the diameters (measured in mils) of a circular region of interest. In one embodiment of the invention shown in FIGS. 8A–8D, each pixel represents 0.6621 mils, and the circled regions of interest vary in diameter from 1.3242 mils to 3.7454 mils. In FIGS. 8E–8H, each pixel represents 0.4797 mils, and the circled regions of interest vary in diameter from 0.9594 mils to 2.7136 mils.

Kernel configurations are not limited to those shown in FIGS. 8A–8H and, in general, no connectivity between the pixels is required.

Experimental Results of Texture Recognition

As discussed above, one embodiment of the invention uses a combination of statistical and morphological operations on a digitized image to separate areas of solder paste texture areas from other feature-rich non-paste areas on a printed circuit board, stencil, wafer, or any substrate. FIGS. 9A–9D show the results of a system that utilizes an embodiment of the invention.

Figure 9A:
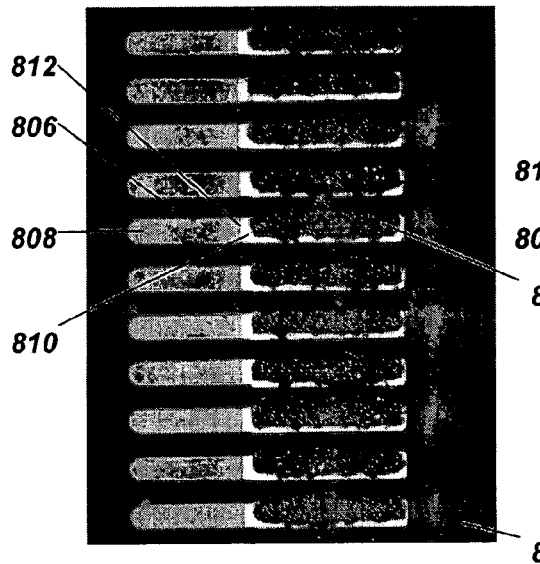
FIGS. 9A–9D is a representation of experimental results from a system that utilizes an embodiment of the invention.

Shown in FIG. 9A is raw image data, with no saturation, of a printed circuit board 802 having solder paste areas 804 and non-paste features distributed thereon. The raw image shows a well-defined edge 806 that outlines a circuit trace 808 leading to a contact region 810, and a well-defined separation line 812 that begins the contact region.

Figure 9B:
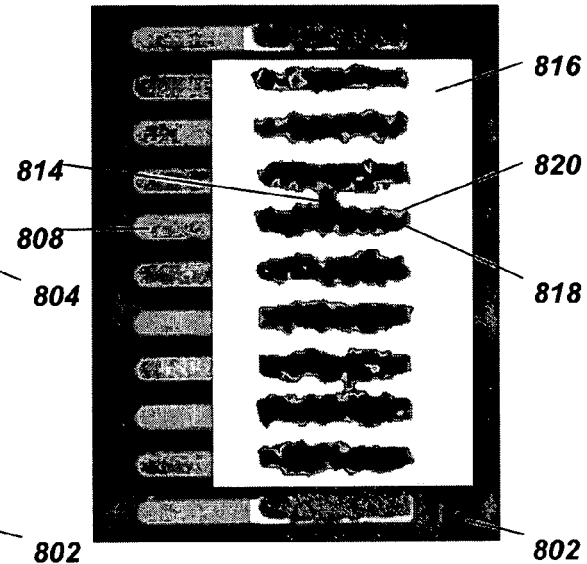

In FIG. 9B, the results of a processed image using the method of the invention is shown. The processed image reveals a solder bridge 814 not seen in FIG. 9A. Note that the non-paste features including edge 806, trace 808, contact region 810, and separation line 812 shown in FIG. 9A are shown as white areas in the region of interest 816, while the solder paste regions 818 are shown as black. Since in the output image the presence of solder paste is represented by a black region, any region that is not totally black or white indicates a scalable transitional region at paste edges or some other area of uncertainty at that location. Accordingly, the gray scalable regions 820 improve the ability to accurately report the location and area of small paste deposits where edges constitute a large percent of the total area and, under certain conditions, is more tolerant of variations in image quality, brightness, and contrast.

Figure 9C:
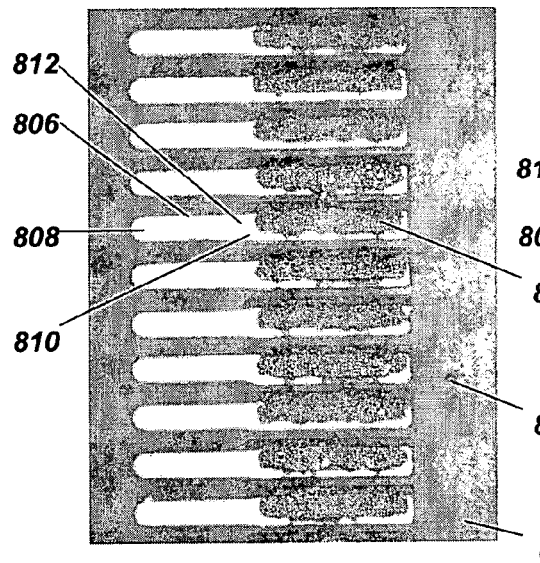

Shown in FIG. 9C is the raw image, with saturation, of the same printed circuit board 802 having solder paste areas 804 and non-paste features distributed thereon. The raw image shows the same well defined edge 806 that outlines a circuit trace 808 leading to a contact region 810. However, the well-defined separation line 812 shown in FIG. 9A, and the gray level representation of trace 808 and the contact pads 810, are indistinguishable in FIG. 9C. FIG. 9C also shows a blemish 822 on the printed circuit board not observed in any of the previous images.

Figure 9D:
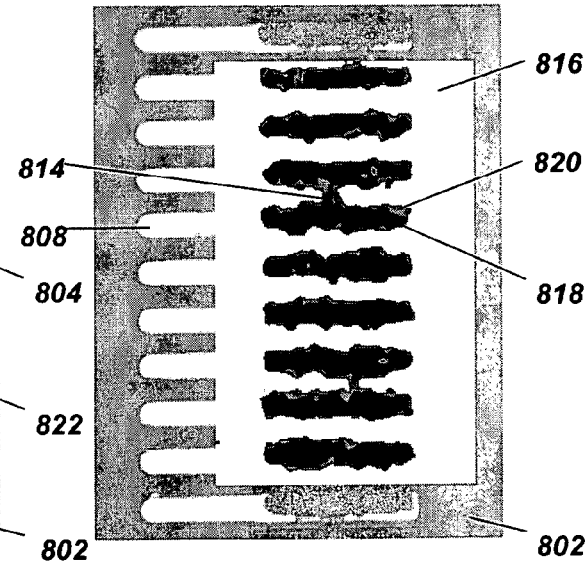

FIG. 9D is the raw image, with saturation, processed utilizing the method of the invention. The processed image shown in FIG. 9D reveals a solder bridge 814. The non paste features 816 are shown in FIG. 9D as white, paste edges 820 and areas of uncertainty in gray, and the solder paste regions 818 are shown as black and represent areas in which 100 percent solder paste is detected. Note that non-solder paste regions, including the blemish 822 shown in FIG. 9C, on the substrate are ignored when the method of the invention is applied. The gray levels are scalable areas that represent regions that lie between the non-essential features on a printed circuit board and the solder paste deposits. The gray scale information allows proportional accounting of edge pixels and any areas of uncertainty. Accordingly, the scalable gray areas convey more information to an observer regarding the quality of the solder paste contact region than a binary image that is either black or white.

Figure 11A:
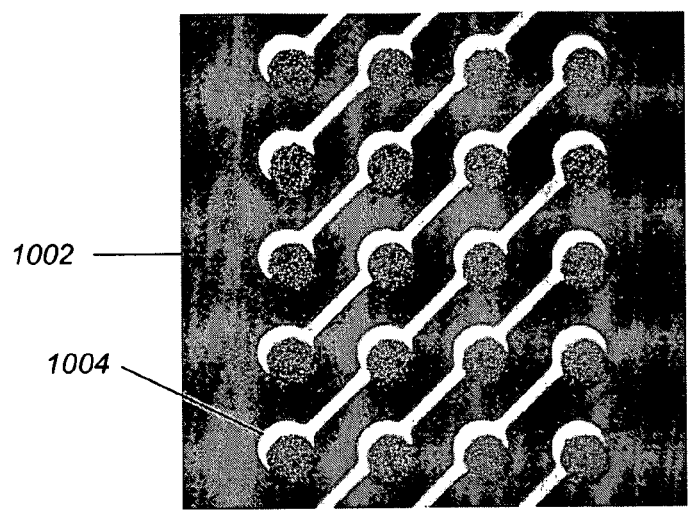
FIGS. 11A–11C is a comparison of raw images from a system that utilizes an embodiment of the invention with saturation.

FIGS. 10A–10C and FIGS. 11A–11C provide a comparison of images from a system that utilizes an embodiment of the invention. FIG. 11A shows the same raw image of FIG.

10A except with saturation. The raw images are processed utilizing the method of the invention. The processed images may be made binary, i.e., black or white, by application of a single thresholding technique, or the processed images may have a scalable gray range by application of a dual thresholding technique. As previously described, dual thresholds make it possible to appropriately account for transitional regions at paste edges and other areas of uncertainty. Accordingly, the method of the invention improves the ability of quality control software programs to accurately report the area of small paste deposits where edges constitute a large percent of the total area, and the method of the invention is more tolerant of variations in image quality, brightness, and contrast.

FIGS. 10A–10C show a series of ball grid array (BGA) images for comparison between a raw image without saturation when single and dual threshold processes are performed on the image. FIG. 10A shows an unprocessed raw BGA image 1002 without saturation, and an array of predetermined contact pads 1004. FIG. 10B shows the results of a single threshold process performed on the raw BGA image shown in FIG. 10A. FIG. 10C shows the results of a dual threshold process utilizing scalable gray levels performed on the raw BGA image shown in FIG. 10A. Edges and regions of uncertainty are in shades of gray. One region of uncertainty appears at 1006.

Figure 11B:
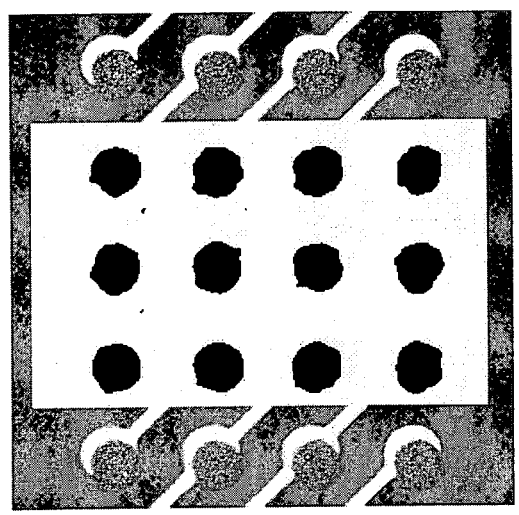
Figure 11C:
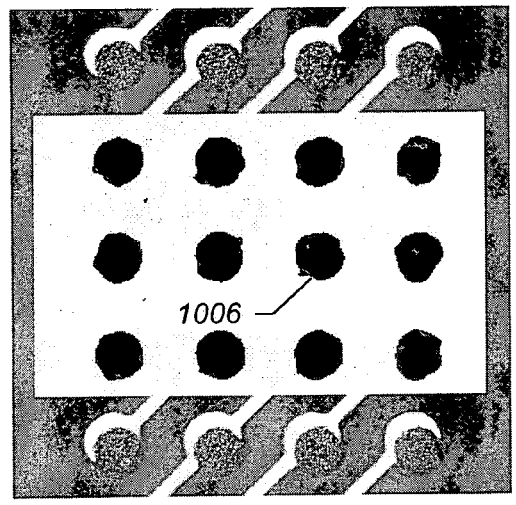

FIGS. 11A–11C show a series of BGA images for comparison with the raw BGA image 1002 with saturation when a single threshold process and a dual threshold process are performed on the image. FIGS. 11A–11C also serves as a comparison of images from a ball grid array (BGA) from a system that utilizes an embodiment of the invention with saturation. FIG. 11A shows an array of predetermined contact pads 1004, and an unprocessed raw BGA image 1002 with saturation. FIG. 1I B shows the results of a single threshold process performed on the raw BGA image 1002 of FIG. 11A. FIG. 11C shows the results of a dual threshold process utilizing scalable gray levels performed on the raw BGA image of FIG. 11A. Edges and regions of uncertainty are in shades of gray. The same region of uncertainty 1006 appears in both FIG. 10C and FIG. 11C.

FIGS. 10B–C and FIGS. 11B–C show that the method of the invention is tolerant of significant image brightness and contrast variations in non-paste features, including non-linear brightness changes, and data loss due to saturation or drop-out of non-paste features.

Figure 12:
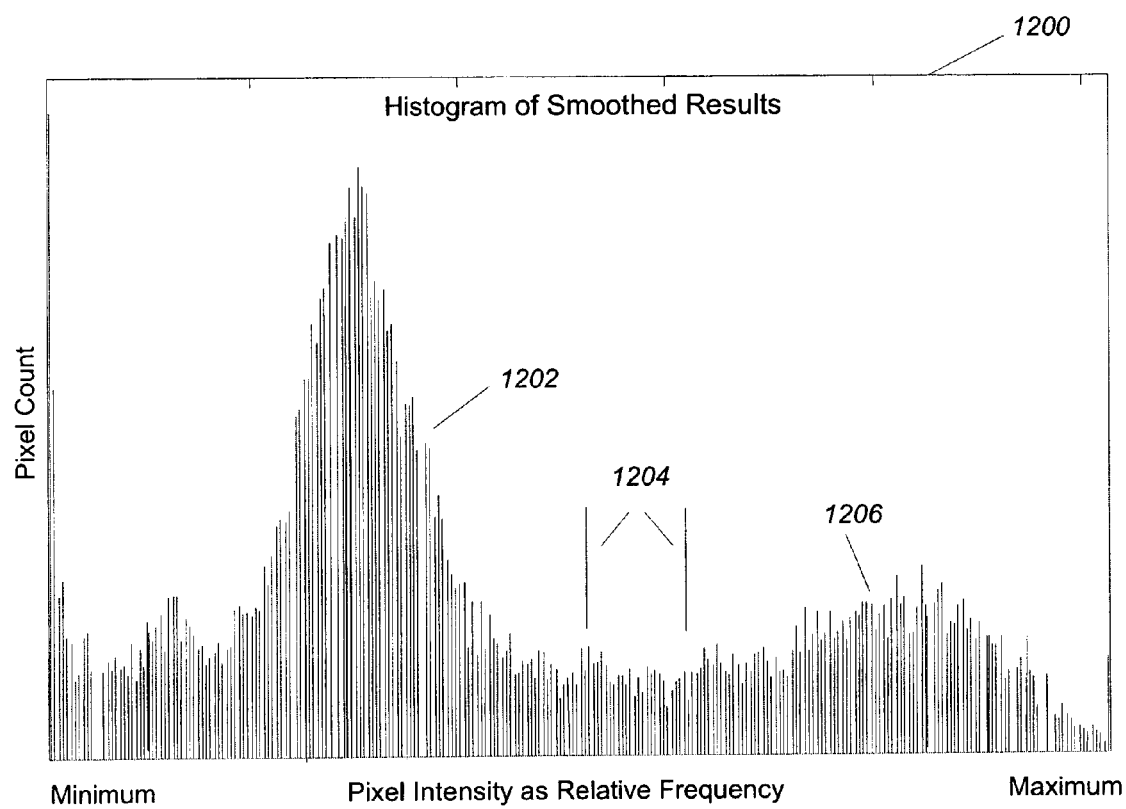
FIG. 12 is a histogram of experimental results from a system that utilizes an embodiment of the invention.

FIG. 12 shows a histogram 1200 of the smoothed results of a system that utilizes an embodiment of the invention. The histogram is divided into three regions: a non-paste region 1202, a transition region 1204, and a solder paste region 1206. The histogram 1200 shows a distribution of pixel brightness which corresponds to the texture in the smoothed image. In one embodiment, the smoothed image depicts paste as white and non-paste as black. Accordingly, paste pixels 1206 favor the right end of the histogram and non-paste pixels 1202 favor the left end. Transitional pixels 1204 corresponding to an edge in the image is shown in the area between the paste and non-paste regions. In another embodiment of the invention, the smoothed image is inverted to depict paste as black and non-paste as white.

Bridge Detection Methods

Figure 13:
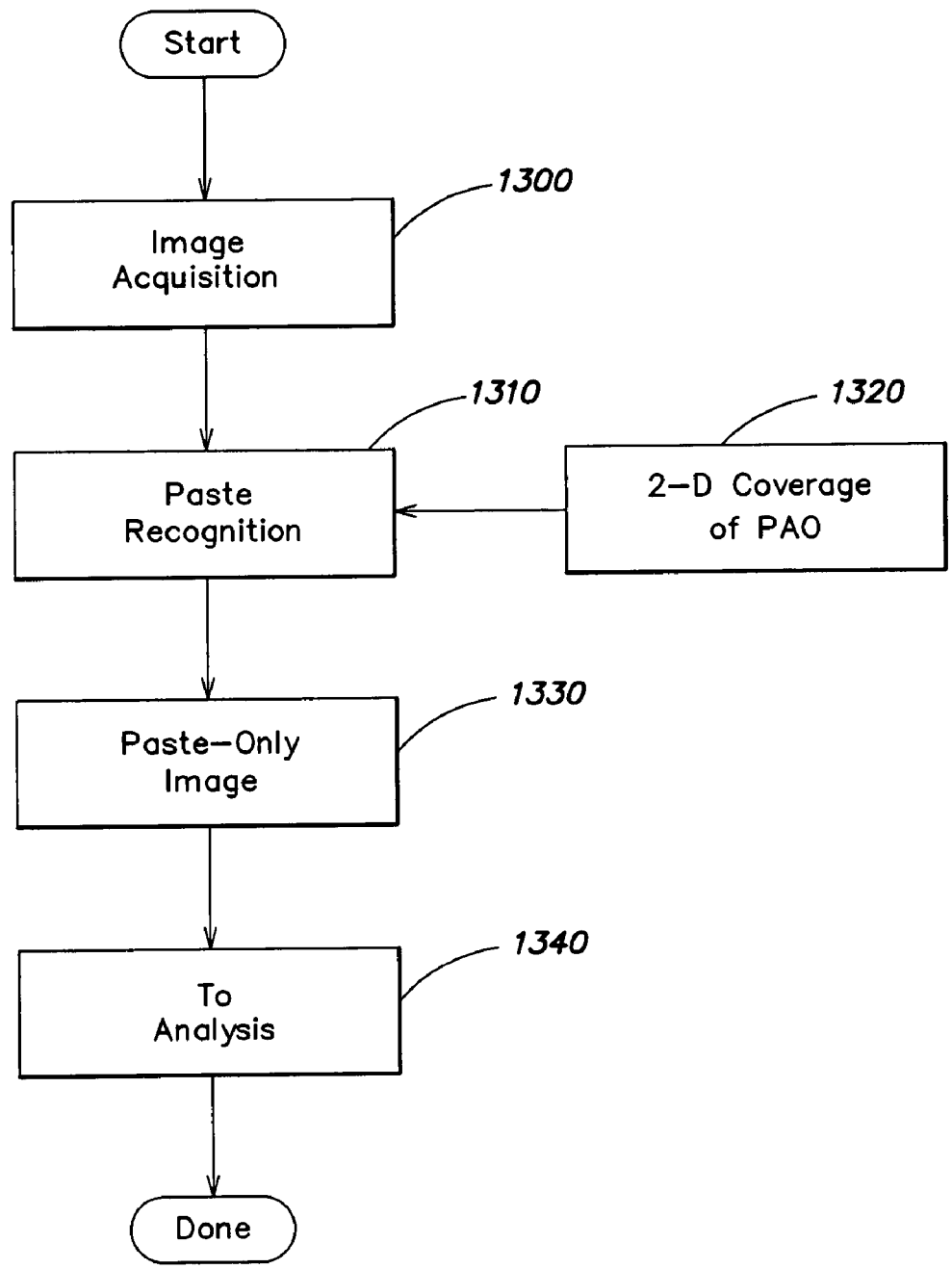
FIG. 13 is a flowchart of a prior art process for inspecting solder paste deposited on a substrate.
Figure 14:
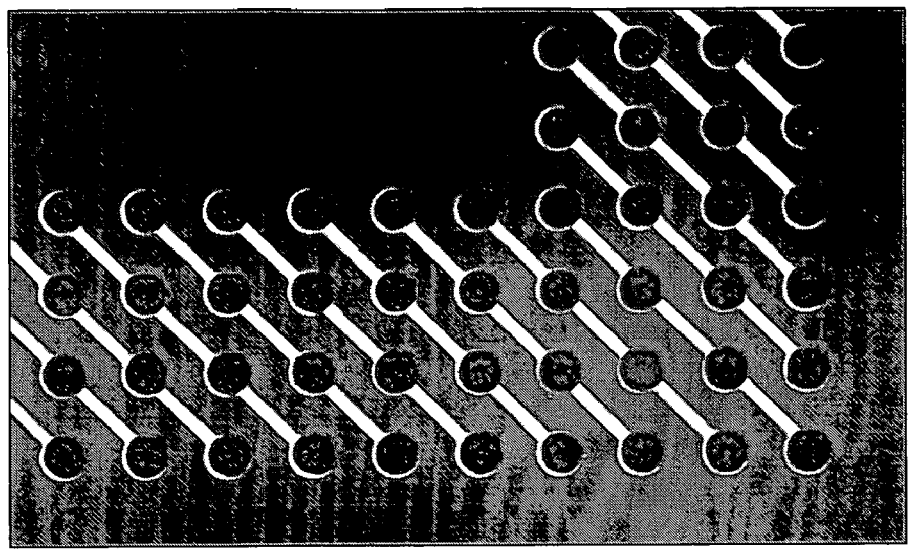
FIG. 14 is a greyscale image of paste acquired in the acquisition step of FIG. 13.
Figure 15:
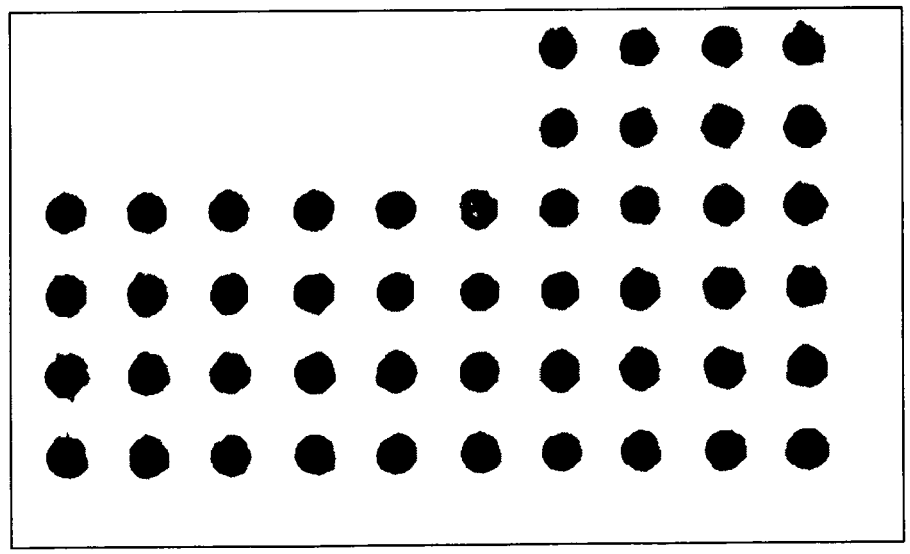
FIG. 15 is a weighted paste only image of the grayscale image of FIG. 14 as converted to a paste only image during the paste-only image step of FIG. 13.

FIG. 13 is a flowchart of a prior art process for inspecting solder paste deposited on a substrate. As an initial operation, the image of a section of the board is acquired, such as by an area or line scan camera (step 1300). FIG. 14 is an illustrative example of an image acquired in step 1300 of FIG. 13. FIG. 14 is a grayscale image of solder paste. The image acquired in step 1300 is processed so that regions of the board that are covered with paste are more easily identified (step 1310). For example, a paste detection (also referred to as paste recognition) process is performed on the image to separate solder paste from non-paste features (e.g., the conductive pads, the substrate) creating a new "paste-only" image (steps 1310 and 1330). FIG. 15 is an illustrative example of a weighted paste-only image based on paste detection applied to the image of FIG. 14. The resulting image is not necessarily analyzed during paste detection at this stage to determine the quantity, location, or significance of paste deposits. Instead, a separate process (step 1340) may be used to analyze the paste-only image.

Figure 16:
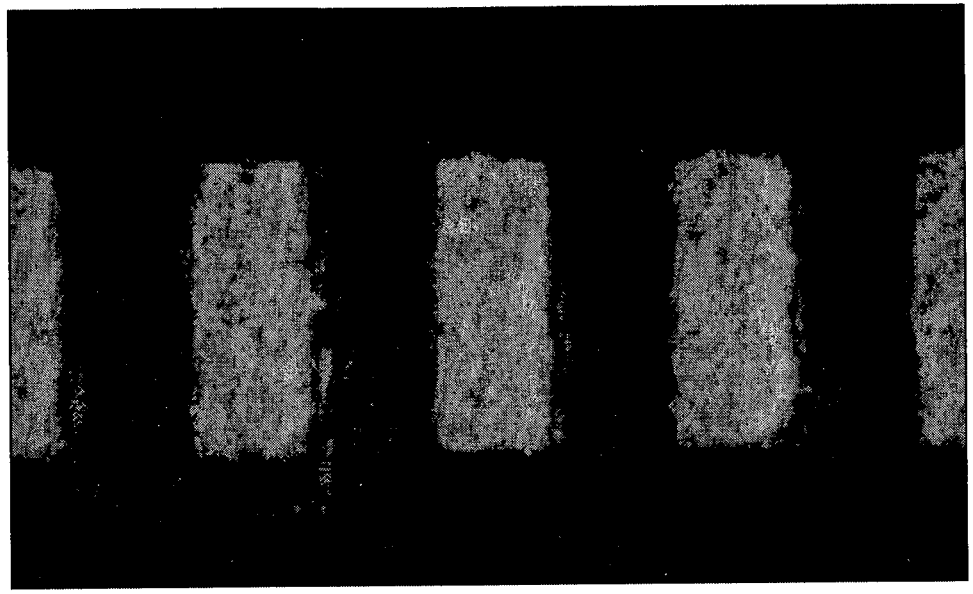
FIG. 16 is an RGB image of UV enhanced fluorescent paste acquired during the acquisition step of FIG. 13.
Figure 17:
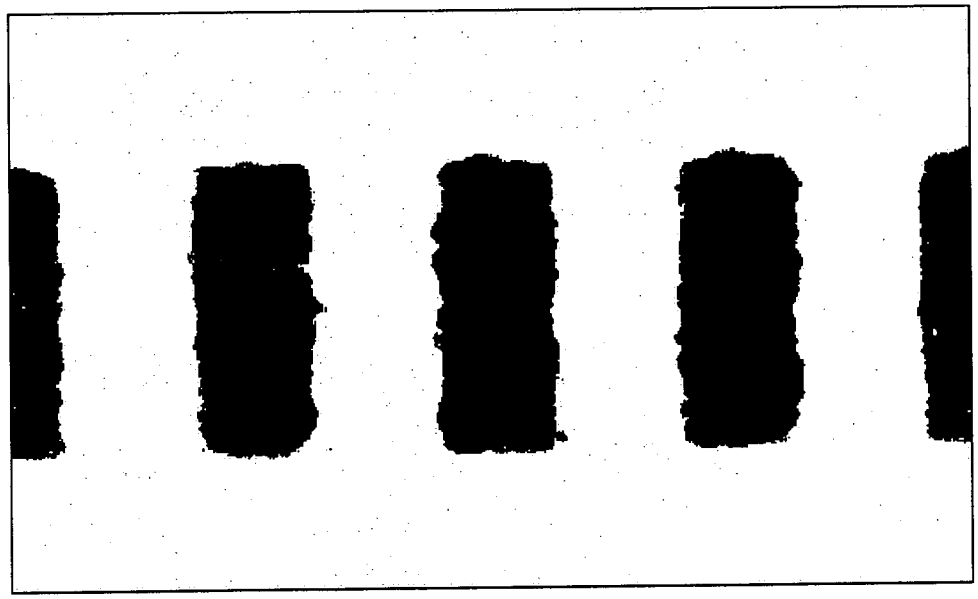
FIG. 17 is a binary paste only image of the RGB image of FIG. 16, as converted to a paste only image during the paste-only image step of FIG. 13.

Many different techniques can be used to separate the solder paste from non-paste information. One known technique is thresholding, which can be used to divide an image into sections based on brightness or some other parameter, such as visibility under a type of light. A single threshold (or brightness level) is chosen to create a binary image depicting paste and non-paste regions. Threshold techniques segment an image into regions of interest and removes all other regions that are outside of the threshold and are thus deemed not essential. For example, a fluorescent dye can be added to solder paste so that only the paste is visible under a particular type of light. FIG. 16 is a Red Green Blue (RGB) image of UV entranced fluorescent paste, and FIG. 17 is a binary paste-only image from a "blue" light channel, using a "single threshold" method. Dual threshold methods work similarly but include a scalable transition region of brightness levels between thresholds to more accurately account for edge pixels. The dual threshold method is sometimes preferred over the single threshold, since small paste features can contain a relatively significant amount of edge data.

Another known technique for paste detection is image subtraction. Subtraction methods create a "difference image" by subtracting one image from another. Some subtraction-based paste detection methods compare differences between a reference image and a newly captured image to detect paste. In some instances, these images must be registered precisely to each other before subtraction to minimize error. A relatively significant amount of computer storage, data retrieval, and memory buffer capabilities may be needed to accommodate the many reference images. Ideally a complete set of reference images need only be acquired once, but in doing so, performance can be adversely affected by typical variations found between otherwise identical substrates. To avoid such problems, new reference images can be acquired for each substrate to be inspected, but this can slow the process considerably and may be inappropriate for use in a high-speed production environment. Variations of the thresholding and/or image subtraction techniques may include use of laser profiling to create a topographical image, and x-ray techniques. These and other methods are intended to better separate paste from non-paste regions for subsequent analyses.

One drawback that can occur with thresholding and image subtraction is that brightness levels of the solder paste and the background can often overlap. This overlapping can make it difficult, if not impossible, to effectively separate the solder paste images from background information. In addition, area and location of paste deposits cannot be determined with certainty under such conditions thus limiting the value of statistical process control (SPC) data and adaptive control responses.

One reason for identifying solder paste areas on a printed circuit board is to detect solder defects, such as bridges. In solder paste printing operations, the term "bridge" can describe a print defect where some amount of stray paste spans (or nearly spans) the gap between adjacent pads, or where some amount of stray paste spans a gap between pads beyond predefined limits. Bridges can be significant because, at critical dimensions, a bridge of solder paste may fail to pull back during subsequent reflow operations, causing a short or other related defect in the final assembly. Bridges are not the only type of print and/or paste defects. Other defects, such as excess paste, poor print definition, and poor alignment also can increase the probability that similar defects, especially "shorts", may appear at the location of the original defect later in the assembly process.

One approach to increasing the yields associated with the solder paste deposition process is to detect print defects immediately after the print operation and reject defective boards before the placement of electronic components. This enables surface mount technology (SMT) manufacturers to save time otherwise wasted in the assembly of defective boards and avoids costly rework. Whether or not a defect is reported at any specific site, SPC data can be collected and used to monitor and correct undesirable trends before they become critical to the process.

Assessment of bridges, bridge-like features, and other print defects can be a subjective task with few hard rules or limits. Subjective descriptions of print defects such as "bridge," "bridge-like," "too much paste" may be viewed as subjective descriptions of print defects. Without further technical assessment, it is difficult to use any or all of these subjective descriptions to predict whether a defect, such as a bridge-related defect, will appear later in a given process, or to indicate the presence of a process trend where the probability of such a defect is increased.

Some known techniques used to detected bridges, such as so-called simple "blob" and "bounding box" techniques, as well as bridge-detection techniques that rely solely on the area of the paste in a region of interest (e.g., a gap between pads), can be subject to binary "noise" and may provide little information about the geometry or actual significance of features within the "box" or region of interest. Further, paste-in-gap limits must often be set relatively high to avoid false detection. None of these methods can consistently and reliably detect partial bridging or bridge-like tendencies for use in effective and preventative print process control.

As described, the solder paste texture recognition method can be used to detect particular defects that occur on a substrate, such as bridges. In solder past print operations, bridges or bridge-like features can occur when a relatively well-defined deposit of paste spans (or nearly spans) the gap between pads, or when a deposit of paste goes beyond predefined limits. As the span of a paste feature increases across the gap, so does the significance of the feature to the process. A so-called "classic" bridge would span the entire gap, but span alone does not guarantee that a related defect will occur later in the process. Something less than full span could be equally troublesome, or equally benign. Additional characteristics must be considered to gauge the true significance of a defect to the process.

Although sections along a bridge may be narrow or "weak", or its bridge-like geometry poor, it has been found that the probability that bridging will occur at some point during subsequent reflow operations is dependent on the amount, location, and geometry of paste involved. As the area covered by the paste feature increases, so does the probability that the paste will cause a bridge-related defect when sufficient span exists across the gap.

The thinnest point along the bridge feature, its so-called "weakest link," may indicate an ability or tendency of the bridge to break and pull back during subsequent reflow operations. If a section along the bridge is sufficiently narrow, the probability that the paste will break and pull back from this point may be greater than the probability of a deposit that remains relatively (or critically) wide at its narrowest point. As the width or "bulk" of the paste feature increases so does the probability that the paste feature may cause a bridge-related defect, provided a sufficient span exists across the gap and the total amount of paste forming the bridge is sufficient to maintain it during subsequent reflow operations.

Another type of print defect is a so-called "general" print defect. General print defects occur when the total quantity of paste, regardless of shape or location in the gap, is beyond predefined limits. When general print defects are detected, an actual paste bridge need not be confirmed, and no further characterizations of the defect are required to make a decision that a substrate is defective. General print defect conditions indicate generally poor print quality, poor alignment, bridging, or all of these, with an increased probability that a bridge-related defect (e.g., a short circuit) may appear at the location of the print defect later in the assembly process. For general paste-in-gap defects, a user-defined limit is applied to the total area of paste found in the gap.

The precise inspection of bridges can be a critical tool not only for the detection of many common SMT print defects, but also for correcting undesirable trends in the process. Since a relatively insignificant paste-in-gap area can provide significant bridge geometry across the gap, and vice versa, both paste-in-gap and span measurements are needed to reliably determine the true significance of bridge-like features to a process.

One embodiment of the invention provides systems and methods for gap defect analysis that provides reliable paste-in-gap area measurement and detects significant geometry and span of bridge-like paste features as they relate to the surface mount technology (SMT) assembly process. In one embodiment, the total amount of paste in a gap and the effective span of bridge-like features across the gap are used together to determine the probability that a specific paste feature will cause a bridge-related defect.

Figure 18:
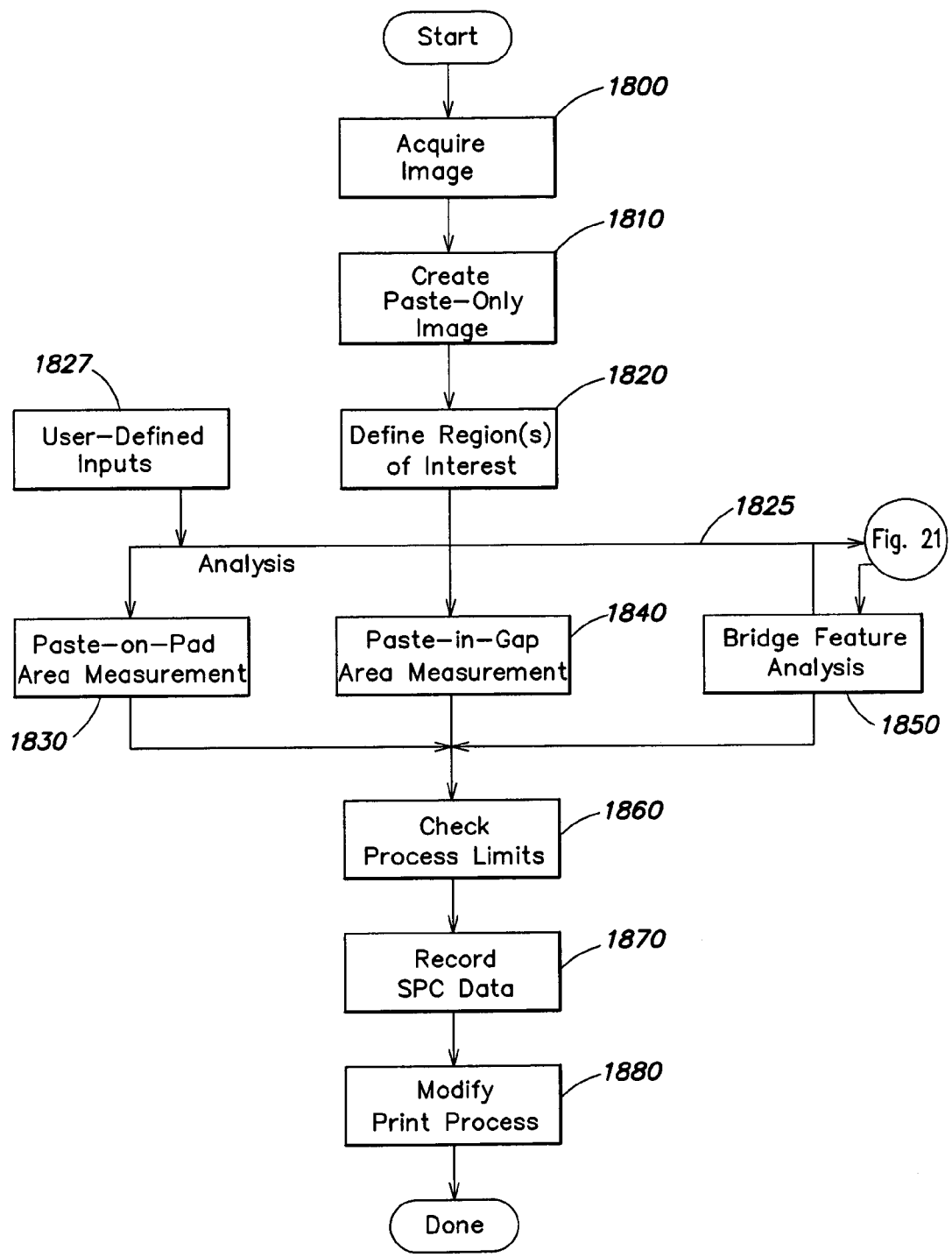
FIG. 18 is a flowchart of a print defect detection sequence, in accordance with one embodiment of the invention.

FIG. 18 is a flowchart of a print defect detection sequence, in accordance with one embodiment of the invention. The invention can use an image acquired in virtually any manner (step 1800), as long as the image is (or can be) suitably segmented into a "paste-only" image (step 1810). The image can be what is commonly referred to as a "digitized" image. The paste-only image, also referred to herein as a "processed image", can, for example, be a binary image or may have weighted gray levels to appropriately account for transitional regions at edges and other areas of uncertainty. Use of various image enhancement techniques, including so-called "leveling" or "field flattening" techniques, can be applied to the acquired image during the first stages of processing to ultimately improve the fidelity of the resulting paste-only image.

In at least one embodiment of the invention, the paste-only image uses weighted pixels. Use of weighted pixel values improves the ability of the bridge analysis of the invention to accurately report area and thus the significance of small paste deposits where edges constitute a large percent of the total area and, under certain conditions, is more tolerant of minor variations in image quality, brightness, and contrast. In addition, use of weighted pixel values can achieve more accurate bridge detection results, particularly in small gap areas containing relatively few pixels or sample points. In one embodiment of the invention, a pre-determined look-up table, such as a 256 element lookup table, can be used to effectively weigh pixels during creation of the paste-only image 1810, at run-time, without requiring highly repetitive, redundant, run-time math operations.

"Paste-only" images can be created via the methods described previously, including but not limited to direct application of single or dual thresholds to an acquired image, image subtraction techniques, and the texture based segmentation technique described herein. Other usable techniques for creating paste-only images, as described previously, include use of UV-dye enhanced paste, laser profiling, use of interferometry to create 2D representations of topographical data (i.e., an image of "volume elements", or "voxels"), and x-ray techniques. Those skilled in the art will appreciate that many methods now known and to be developed in the future for producing segmented paste-only images are usable in at least some embodiments of the invention.

Referring again to FIG. 18, within the paste-only image (step 1810), a region of interest is defined (step 1820). The region of interest, in one embodiment, is a region in which it is desired to know the amount and characteristics of a substance deposited therein. For example, on a PCB, wafer, stencil, or similar substrate this region of interest may be the gap between pads or apertures where the presence of bridge or bridge-like features is undesirable. FIGS. 19A–19C and 20A–20C, described below, illustrate run-time and paste-only images showing a "region of interest".

Figure 19C:
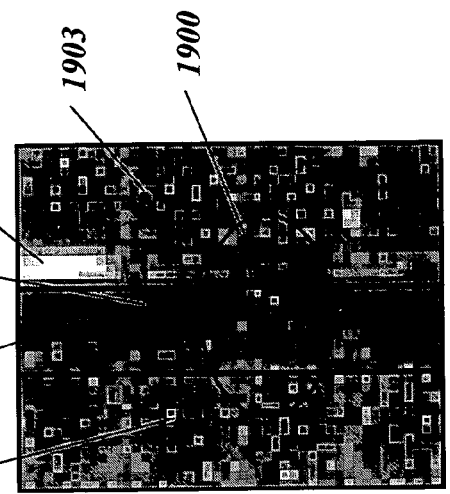
FIGS. 19A–19C are details of a run-time image with illustrative features indicated, in accordance with an embodiment of the invention.
Figure 19B:
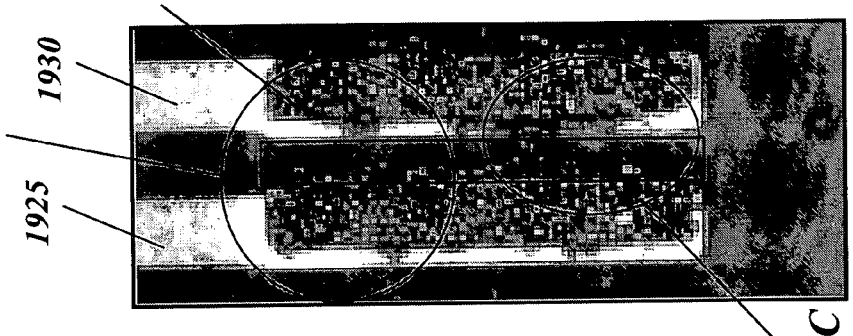
Figure 19A:
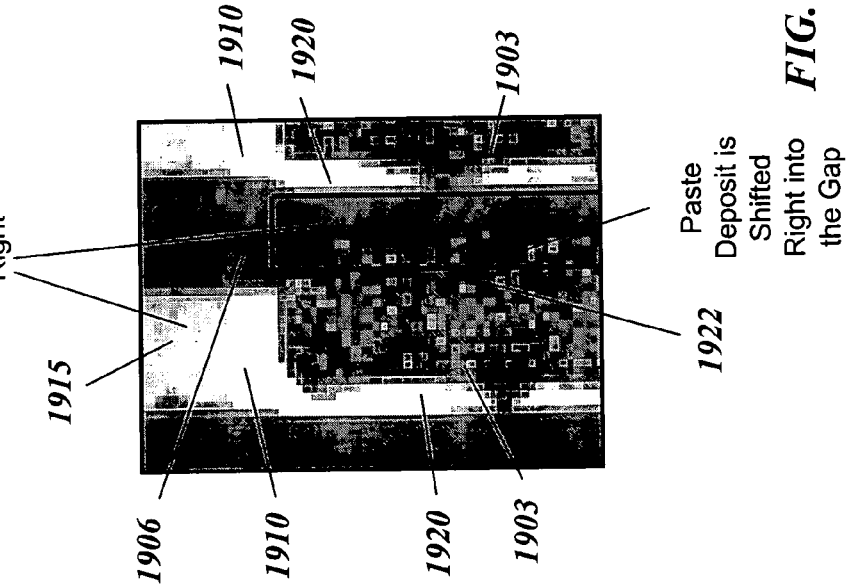

FIGS. 19A–19C are details of a run-time image with illustrative features, including an example of a region of interest, in accordance with an embodiment of the invention. FIGS. 19A–19C illustrate enlarged views of a bridge-like feature 1900 in the solder paste 1903, and several typical non-paste (board) features. FIG. 19A is an enlarged view of a first portion of the run time image shown in FIG. 19B, and FIG. 19C is an enlarged view of a second portion of the run time image in FIG. 19B, including the bridge-like feature 1900 and solder paste 1903. The non-paste features include, for example, a bare board 1906, a bare trace 1910, the mask 1915 on the trace 1910, and the bare pad 1920. FIGS. 19A and 19B also illustrate a gap 1920 between a first solder pad 1925 and a second solder pad 1930. In this example, the solder paste 1903 is shifted to the right of the first solder pad 1925, into the gap 1920.

FIGS. 20A–20C are corresponding paste-only views of the images shown in FIGS. 19A–19C, respectively. FIGS. 20A–20C are illustrative examples of paste-only images created in accordance with the texture based method described herein. As mentioned, texture-based images are but one example of a plurality of suitable paste-only images. In FIG. 20, the possible bridge-like feature 1900 is circled.

Referring again to FIG. 18, the paste only image of FIG. 20B can be used for step 1810 and the gap region of interest 1920 shown in FIGS. 19A and 20A can be used for step 1820, in at least one embodiment of the invention. However, it is possible in at least one embodiment to reverse steps 1820 and 1810—that is, to define the region of interest in the acquired image, then create a paste-only image of the region of interest only. Doing so may save processing time. In at least one embodiment of the invention, the paste-only conversion of step 1810 is performed over a region no bigger than that required to include all sub-regions as defined in step 1820.

In step 1850, a projection and sliding average method (see FIG. 21 and related discussion, below) is used on the suitably segmented paste-only image to ultimately detect and analyze significant bridge or bridge-like features within the specified region of interest. In addition, user defined inputs are set in step 1827, described in FIG. 22 and related discussion. These user defined inputs help to measure the area of the paste on pad (step 1830) and the paste in the gap (step 1840), and to analyze the bridge feature (step 1850).

Figure 22:
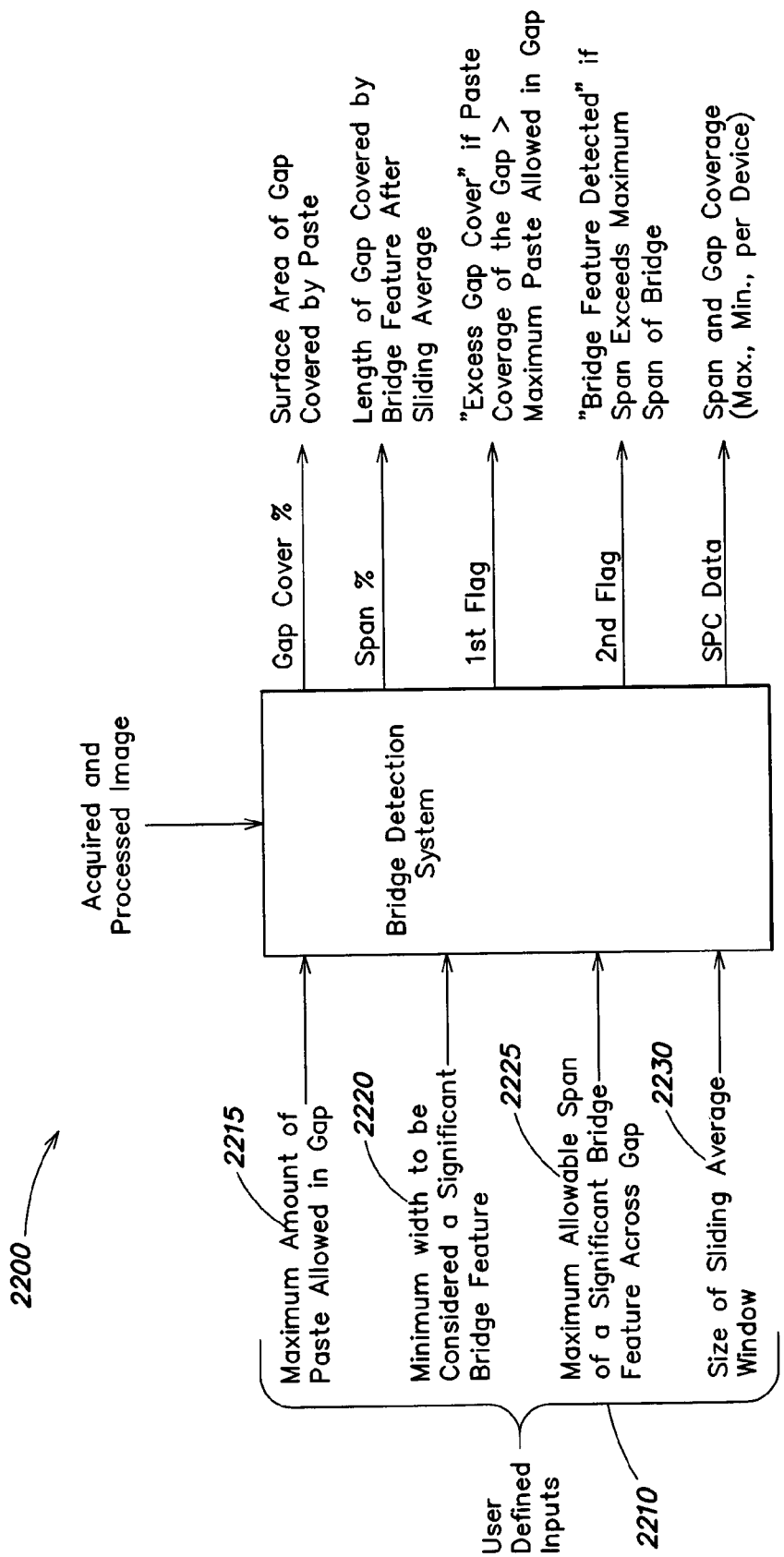
FIG. 22 is a general block diagram illustrating the inputs and outputs of a system implemented in accordance with an embodiment of the invention.

Referring briefly to FIG. 22, which is a general block diagram illustrating the inputs and outputs of a system 2200 implemented in accordance with an embodiment of the invention, several user defined inputs 2210 are shown. These include the maximum amount of paste allowed in the gap 2215, the subjective "sensitivity" setting of the bridge detection system 2220, and the maximum allowable span of a significant bridge feature across a gap 2225.

The maximum amount of paste allowed in the gap 2215 represents what the user specifies as the maximum amount of paste that can be in a gap before the quantity of paste is taken to indicate a significant print defect. For example, this can be expressed as a percent of the nominal gap area, such as 55%, meaning that up to 55% of the nominal gap area can be covered by paste before a paste-in-gap defect is said to occur. These numbers are purely illustrative.

The "sensitivity" setting 2220 is used to calculate the size of a sliding average window (a.k.a. the smoothing kernel) in step 2230, and ultimately determines the degree of smoothing, or filtration, applied to projected data as described later. This allows users to specify the minimum width, or "bulk", of a bridge feature to be considered in span measurements in relative terms, and is preferred. Alternatively, the user could enter the "sensitivity" in more direct units, including pixels, mils, and microns. In the embodiments of the invention described herein, the width of the smoothing kernel 2230 and thus the minimum width of a feature considered to be a bridge feature is measured in pixels, such as 5 pixels wide, 10 pixels wide, etc. These numbers are purely illustrative and will, of course, vary depending on the level of bridge detection sensitivity desired.

The maximum allowable span of a significant bridge feature across a gap 2225 represents what a user specifies to be the maximum amount that a feature, such as a bridge feature, can extend across a region of interest, such as a gap between pads. For example, this can be expressed as a percent of the gap, such as 70% of the width (or length) of a gap, in a direction parallel to the "bridging" axis. This number is purely illustrative.

The size of a sliding average window 2230 is the size of the one-dimensional smoothing kernel, which is used in at least one embodiment of the invention to smooth projected values of a gap. This provides a localized average at each point along the projection while removing a corresponding level of fine detail not considered to be significant to the process. This feature is described further herein. As an example, the size of a sliding average window can be measured in pixels, e.g., 5 pixels. In at least one embodiment, the size of the sliding average window 2230 is based at least in part on the minimum width of a feature to be considered to be a significant bridge feature. The sensitivity settings of step 2220 are in relative terms (e.g., low, medium, high) that ultimately determine the width of the sliding average, in pixels, in step 2230.

Referring again to FIG. 18, the paste-on-pad area measurement of step 1830 is a straightforward measurement of the amount of paste found within a slightly enlarged region of interest surrounding a pad. This is a 2-dimensional surface area measurement, known to those skilled in the art, and similar to the general paste-in-gap area measurement. Paste-on-pad area measurement is the simplest and most universally applied prior art used for paste inspection. It is included here as part of the preferred mode of operation, since it shares the same paste-only image and can be used together with the gap area and bridge analyses described in this invention to provide a more comprehensive set of data for control of the print process. Otherwise, the measurement of the paste-on-pad area (step 1830) in the region of interest is independent of the general paste-in-gap area measurement (step 1840) and bridge feature measurement (step 1850). The paste-in-gap area measurement (step 1840) is compared to the user-defined input of maximum amount of paste allowed in the gap 2215. Thus, steps 1830 and 1840 are used to help detect general print defects (described previously) in the region of interest. If a general print defect is detected, the substrate being inspected may be immediately rejected.

Figure 21:
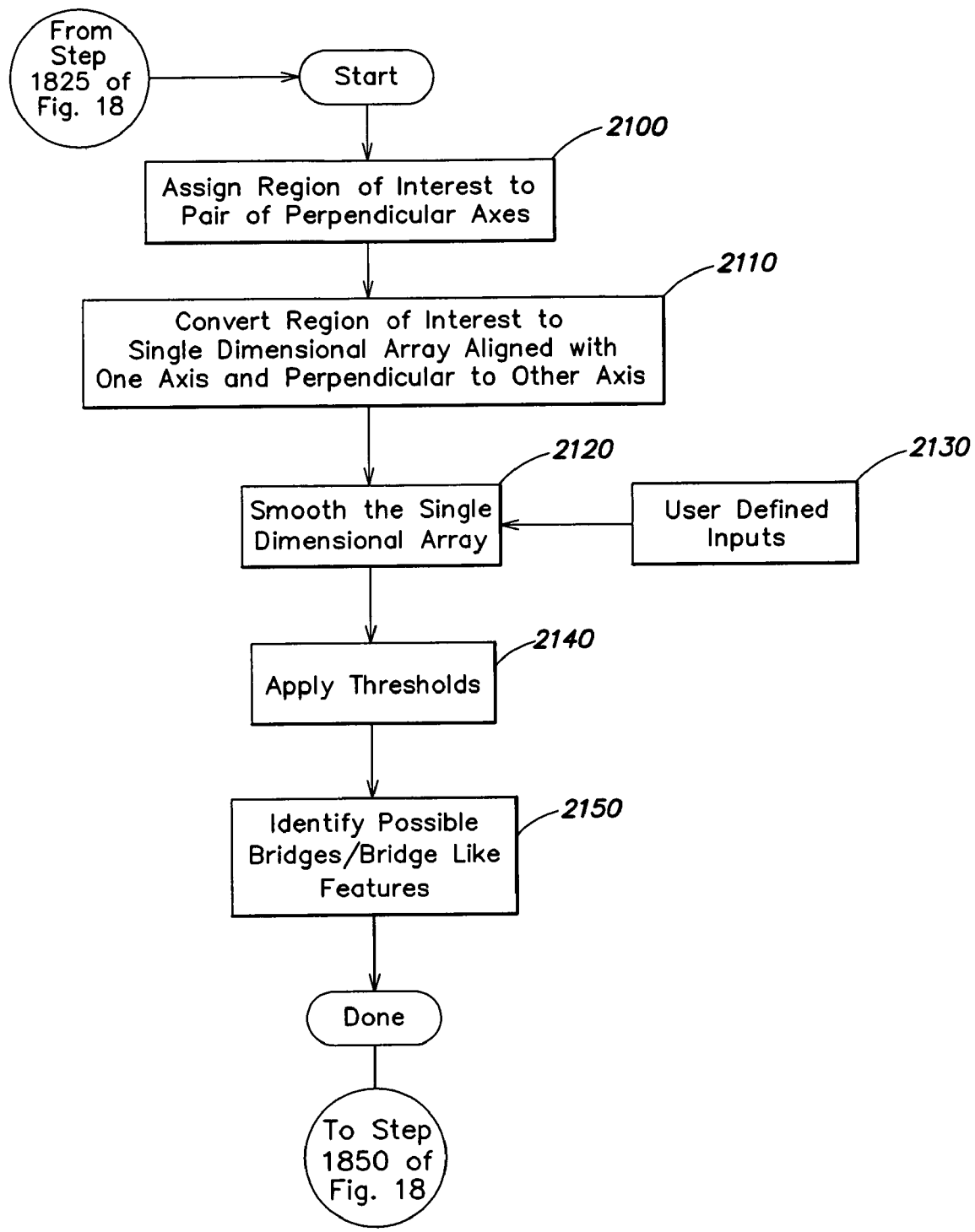
FIG. 21 is a flow chart of a process for bridge feature analysis, in accordance with an embodiment of the invention.
Figure 23B:
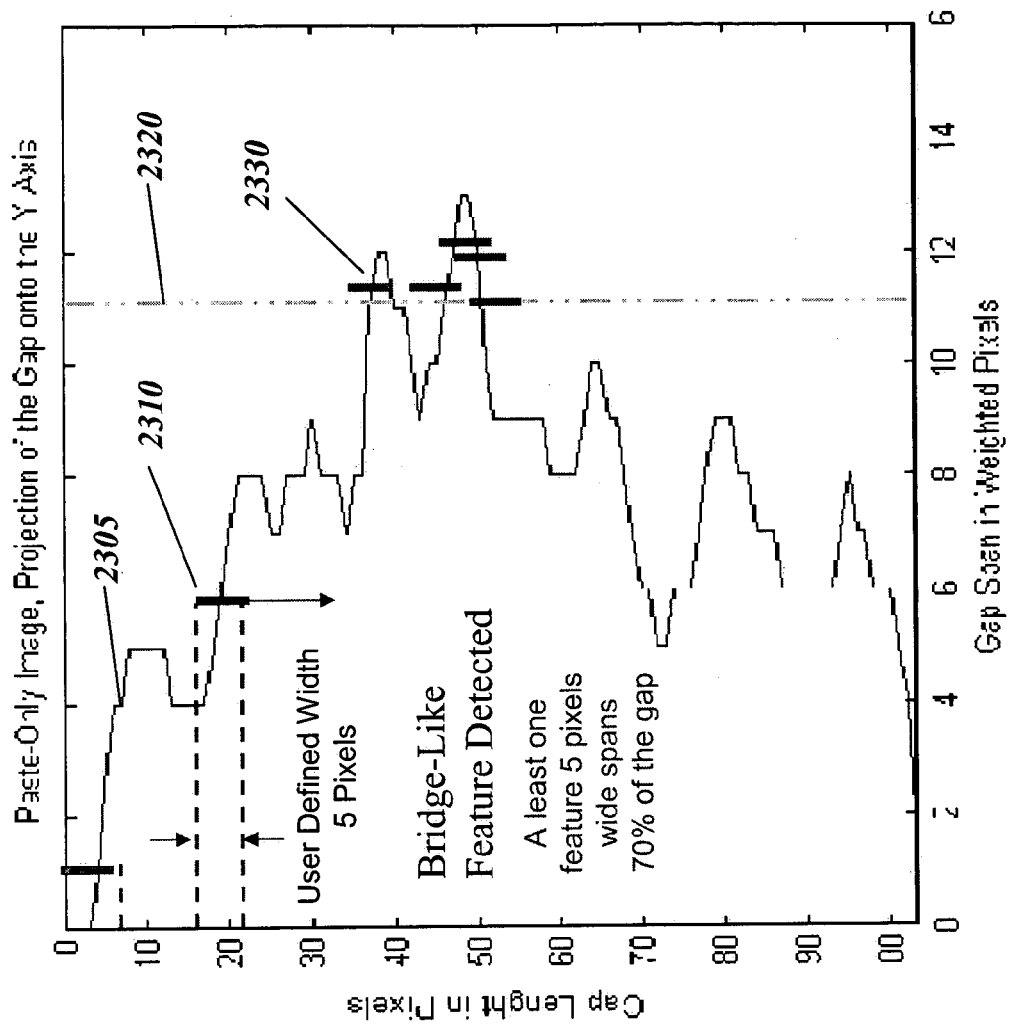
Figure 23B:
Figure 23A:
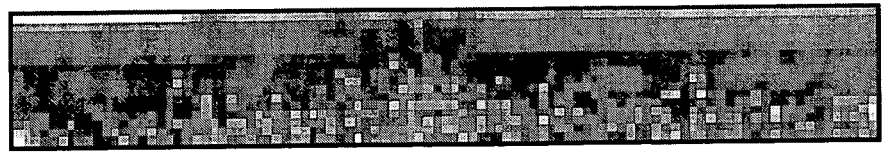

Bridge features in the region of interest are analyzed in step 1850. FIG. 21 is a flow chart of a process for the bridge feature analysis of step 1850, in accordance with an embodiment of the invention. In FIG. 21, to estimate the significance of bridge-like features a pair of perpendicular axes is assigned to the region of interest (step 2100), so that the paste-only images can be first projected onto one axis of the region of interest. For example, FIGS. 23A–23C are first illustrative run-time image, paste-only image, and a plot of the projected paste only image of solder paste in a gap (the gap is specified as the region of interest for illustrative purposes only), processed in accordance with an embodiment of the invention. FIG. 23A is an illustrative example of a region of interest that is a "run-time" image of paste in a gap (which would correspond to, for example, step 1800 of FIG. 18 followed by step 1820 of FIG. 18). FIG. 23B is a paste-only image of the run-time image of FIG. 23A. This is the sliding, or moving, average. A new array is created by smoothing the initial projected values by the specified kernel size. The resulting numbers represent the effective span of the paste at each point along the gap.

As an aside, note that, in FIG. 23B, the paste coverage in the gap is determined to be 45% in step 2215.

Referring again to FIGS. 21 and 23A–C, FIG. 23C is a plot with X and Y-axes corresponding to the dimensions of the gap region pixel. The Y-axis corresponds to the typically longer "non-bridging" axis of the gap, and the X-axis corresponds to the "bridging" or "span" axis of the gap. Of course, these axes may be reversed depending on which is the "bridging" axis. In step 2110, the paste in the region of interest is converted to a single dimensional array 2305 effectively aligned with one axis of the gap and perpendicular to the span or "bridging" axis. This single dimensional array is created, in one embodiment, by what is commonly known by those skilled in the art as a simple "projection" of pixel data along one axis of the region of interest. For example, looking in FIG. 23B along the length of the gap, in this case the Y-axis at about location 38, all of the pixels across the gap span are added together. That total number is divided by 255, the maximum 8-bit gray level, to get an equivalent span in pixels at this location along the Y-axis. This value is plotted along the X-axis in FIG. 23C at a point in the gap span of about 12 pixels, or about 75% of the way across the 16 pixel-wide gap.

The single dimensional array 2305, or projection, is then smoothed to filter out small irregularities caused by relatively weak or otherwise insignificant bridging geometry. Smoothing is a process by which data points are averaged with their neighbors in a series, such as a time series, or image of pixels, to reduce or "blur" the sharp edges and abrupt transitions in the raw data. In one embodiment, the smoothing step 2120 is done by passing a sliding average 2310 (with size determined by user defined/specified parameters; see FIG. 22) over the raw projected data to get a smoother equivalent span at point along the projection. The sliding average is effectively a one-dimensional smoothing kernel. The degree of smoothing is based on the size of the kernel and is analogous to the minimum width of a significant bridge or bridge-like feature. It is not necessary, however, for the size of the smoothing kernel to be the same as the minimum width of a significant bridge or bridge-like feature. The example in FIG. 23 uses a sliding average, or smoothing kernel, of 5 pixels. Taking the average of any 5 consecutive entries of the projection as one side of a rectangle, and the size of the smoothing kernel, or 5, as the other side, a rectangle 2310 can be drawn to represent a functionally equivalent bridge feature at each point along the length of the region of interest. The smoothed results represent the effective span of these "instantaneous" bridge features along the length of the gap, and it is these values, in percent of total gap width, that are checked during step 2140 (FIG. 21), against user-defined limits 2225 (FIG. 22).

For example, in FIG. 23C, the sliding average 2310 has a user-specified width of 5 pixels, which is the same as the minimum width of bridge feature. The sliding average 2310 is passed along the single dimensional array of projected data from a top to bottom direction relative to the image shown in FIG. 23C (of course, the direction could be reversed, and if the projection of the gap is vertical, then the sliding average could be passed from right to left or left to right). The number of elements used in the sliding average (the size of the smoothing kernel), together with the smoothed results and with other user-specified information, enables a functional estimate of area and significant geometry of features along the length of the gap.

Referring again to FIG. 21, in step 2140, the maximum value of a smoothed single dimensional array is first located. Predetermined thresholds (see 2225 of FIG. 22, and graphic representation 2320 of FIG. 23C), which are also user specified, are then applied to the maximum value to determine whether any features "met" or exceed these limits, and if so, a bridge-like defect is detected by definition. For example, in FIG. 23C, the threshold is applied to determine whether any part of the smoothed projection exceeds the user-defined limit 2320, or 70% of the gap. In this example, 5 smoothed values or "hits" 2330 were found to be above the threshold 2320, the locations of which are marked with bars similar to 2310, for illustration. Of course, the threshold and sliding average width (in pixels) shown in FIG. 23C is purely illustrative, and other numbers are usable. Based on the application of the thresholds, possible bridges and/or bridge-like features are identified (step 2140) and returned to step 1850 of FIG. 18.

FIGS. 24 and 25 provide additional examples of embodiments of the invention, showing application of the smoothing and thresholding as described in FIG. 21. FIGS. 24A–24D are second illustrative run-time, paste-only, region of interest, and plot of projected paste-only image data, respectively, of solder paste in a gap, processed in accordance with an embodiment of the invention. In FIG. 24D, the sliding average used is 10 pixels, and the double line 2410 in FIG. 24D shows a plot of the single dimensional array 2405 after smoothing has been applied. In FIG. 24D, it is seen that a single feature meets the requirement of being classified, by definition, as a "bridge like" defect, where the maximum smoothed value is above the user-defined limit.

Figure 24D:
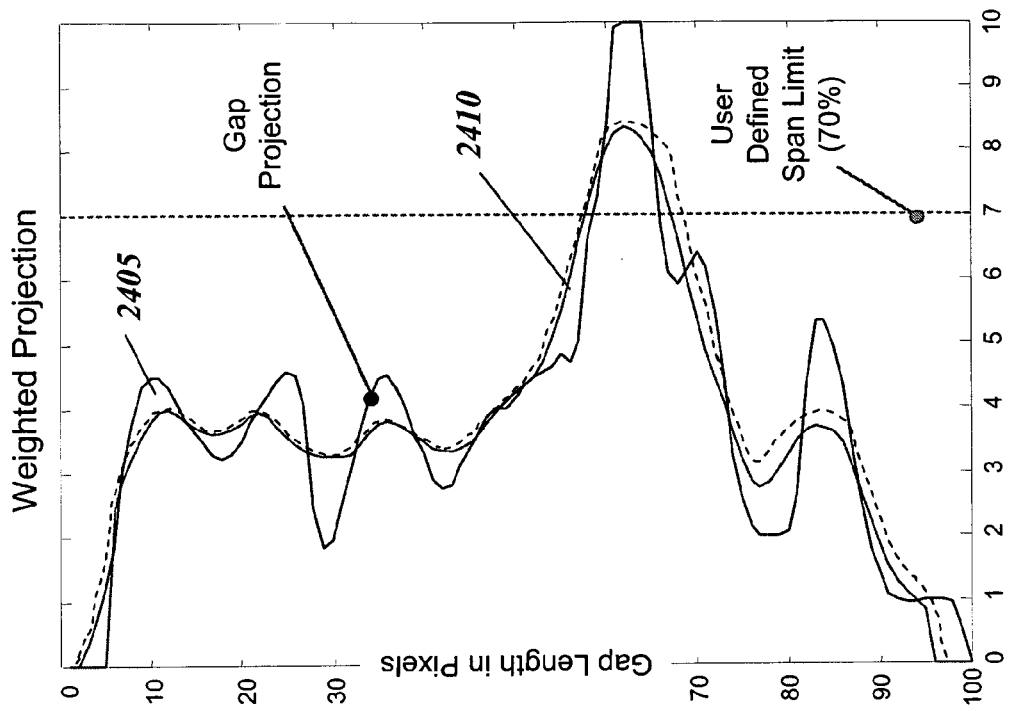
FIGS. 24A–24D are second illustrative run-time, paste-only, region of interest, and projected paste only images of solder paste in a gap, processed in accordance with an embodiment of the invention.
Figure 24C:
Figure 24B:
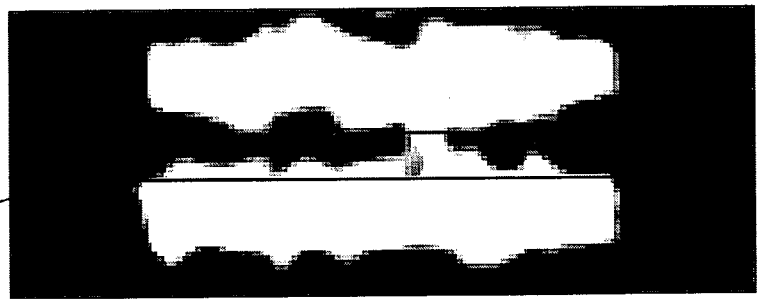
Figure 24A:
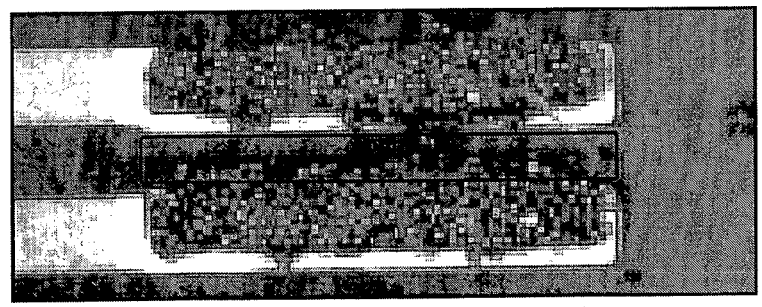
Figure 25C:
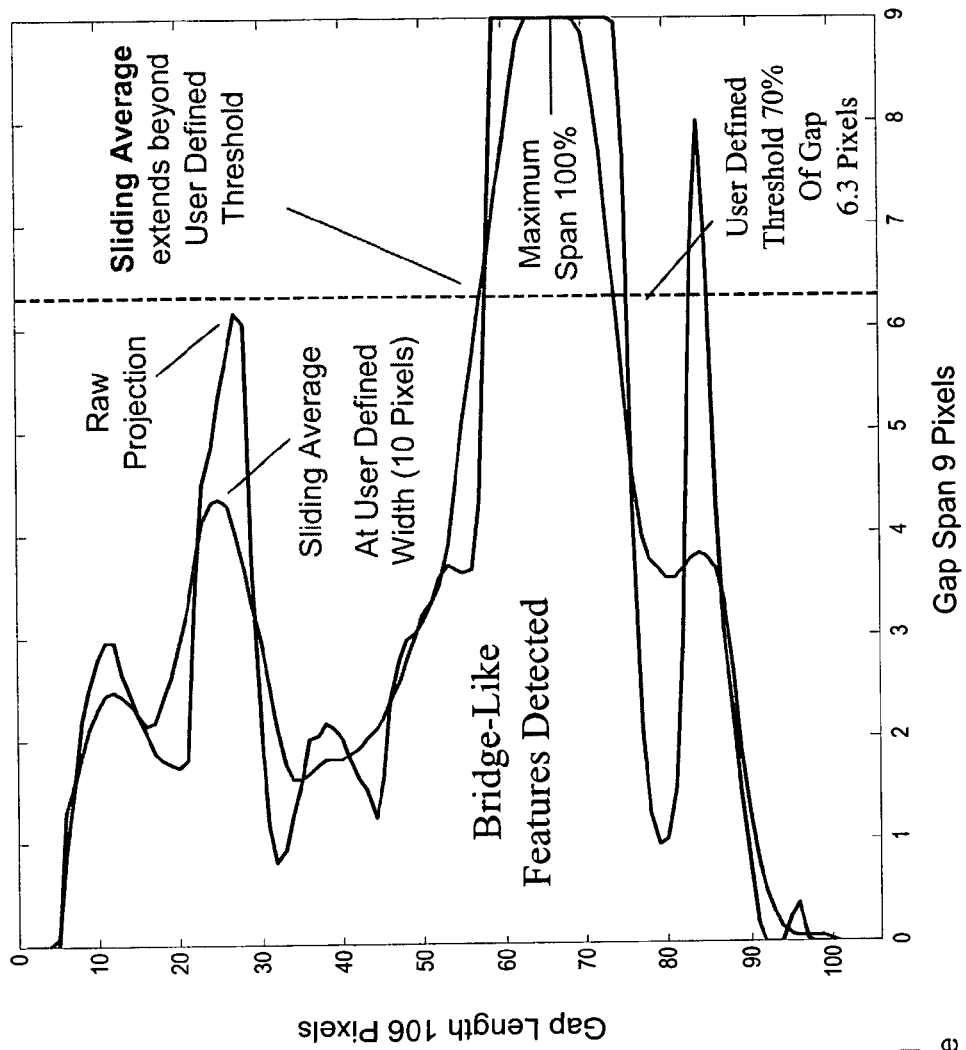
FIGS. 25A–25C are third illustrative run-time, paste-only, and projected paste only images of solder paste in a gap, processed in accordance with an embodiment of the invention.
Figure 25B:
Figure 25A:

FIGS. 25A–25C are third illustrative run-time, paste-only, and projected paste only images of solder paste in a gap, processed in accordance with an embodiment of the invention. In FIG. 25C, the minimum width of a bridge or bridge-like feature is 10 pixels and the user-defined threshold is 70%. These user-defined parameters are the same as in FIG. 24. A relatively substantial solder bridge is visible in FIGS. 25A and 25B. In FIG. 25C, the sliding average extends beyond the user-defined threshold, and does so over a relatively large length of the gap at the 70% threshold line. This graphically illustrates the presence of a strong bridge-like defect with many smoothed values exceeding the threshold, although only one, the maximum value, is required to indicate a bridge-like defect.

In at least one embodiment of the invention, the sliding average can be modified to provide similar sliding root mean square (RMS) output, where data points along the projection are squared before the local mean (sliding average) is calculated. The "root" of these "mean squares" is nearly identical to the simple sliding average values. However, the sliding average may be more advantageous because it requires minimal calculation.

Referring briefly again to FIG. 18, after the analysis of step 1850 is complete, the results can be compared against predetermined (such as user defined) process limits (step 1860), with the resultant data stored (step 1870) for possible modifications to the screen printing/solder paste placement process. Whether or not process limits are exceeded or a defect is reported at any specific site, the data can be appropriately filtered and used to monitor lesser trends for effective control of the print process (step 1880), as will be appreciated by those skilled in the art. For example, the minimum, maximum, and average amount of paste found in gaps between pads can be saved after inspection is complete (e.g., inspection of a given substrate). The same measurements can be saved for span measurements of bridge-like features. This data not only enables trend analyses for effective process control, it provides a means to fine tune detection parameters based on historical performance and realistic production requirements.

The user specified inputs of FIG. 22 are, in at least one embodiment, partially dependent on features of the substrates, such as variations in gap size, pad size, and pad position. For example, in the example embodiments of FIGS. 23, 24, and 25, it also can be seen that the user specified minimum width of a bridge/bridge-like feature can vary depending features such as, the length and width of the gap and on the user specified threshold. This is because the inherent surface tension of substances such as molten solder paste can cause the solder paste to "pull back" and not extend across a gap if the width of the projection is small as compared to the size of the gap, even if the projection extends more than halfway across a gap. Thus, for the example gap span of 9 pixels in FIG. 25C, a larger minimum width of possible bridge/bridge like feature (i.e., 10 pixels) is specified. So, for example, a feature having a width of 9 pixels might be permitted to extend up to 90% of the width of the gap in the example of FIG. 25C, because the tendency of the solder paste is to pull back and not "bridge".

In contrast, for the example gap span of FIG. 23C (i.e., 16 pixels), the minimum width of a bridge feature is 5 pixels. In this example, if the bridge feature extends across 70% or more of the span of the gap, it is unlikely to "pull back" and more likely to "bridge."

Figure 26:
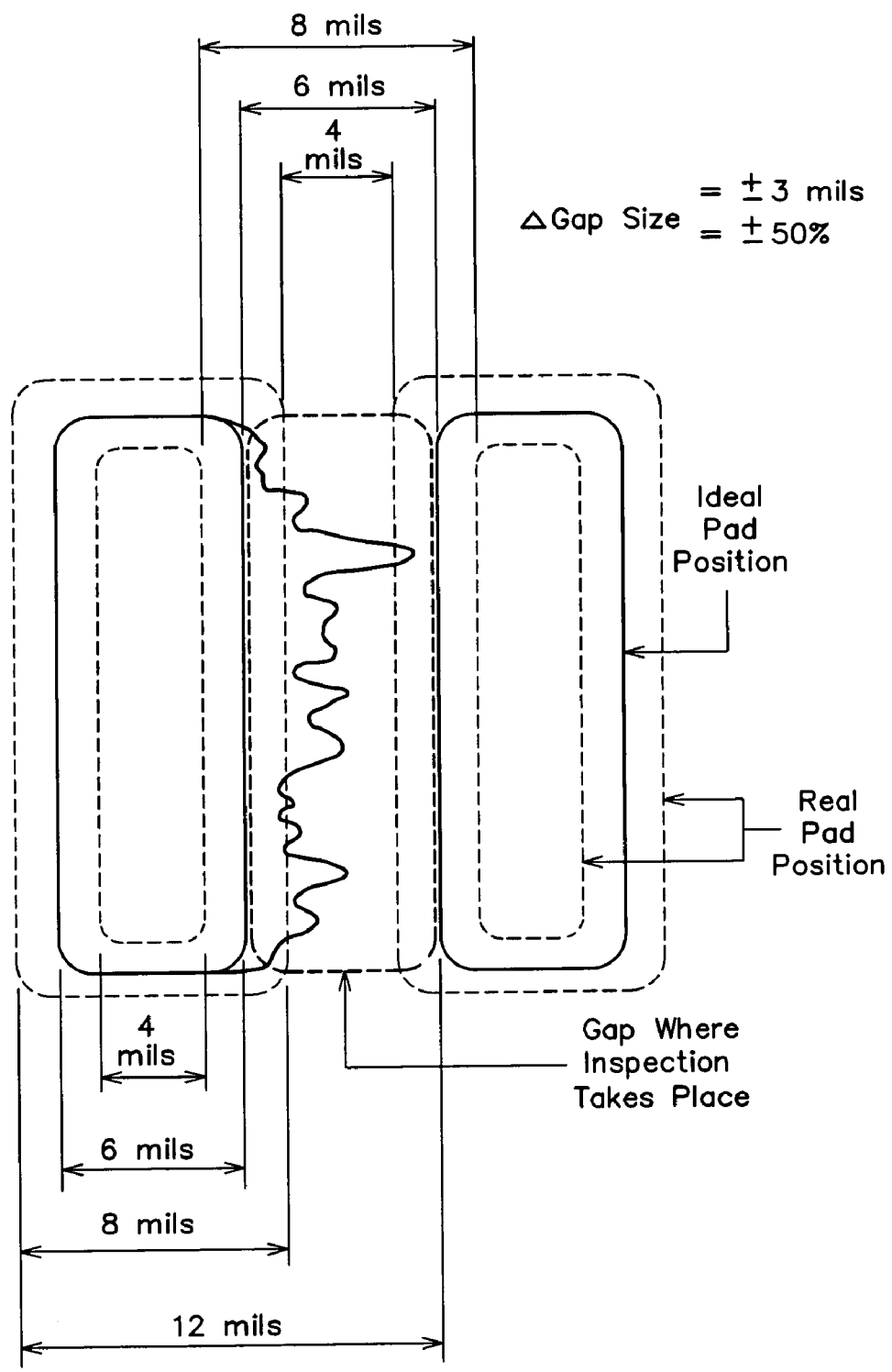
FIG. 26 is an illustration showing the effect of variations in pad size on gap size, in accordance with an embodiment of the invention.
Figure 27:
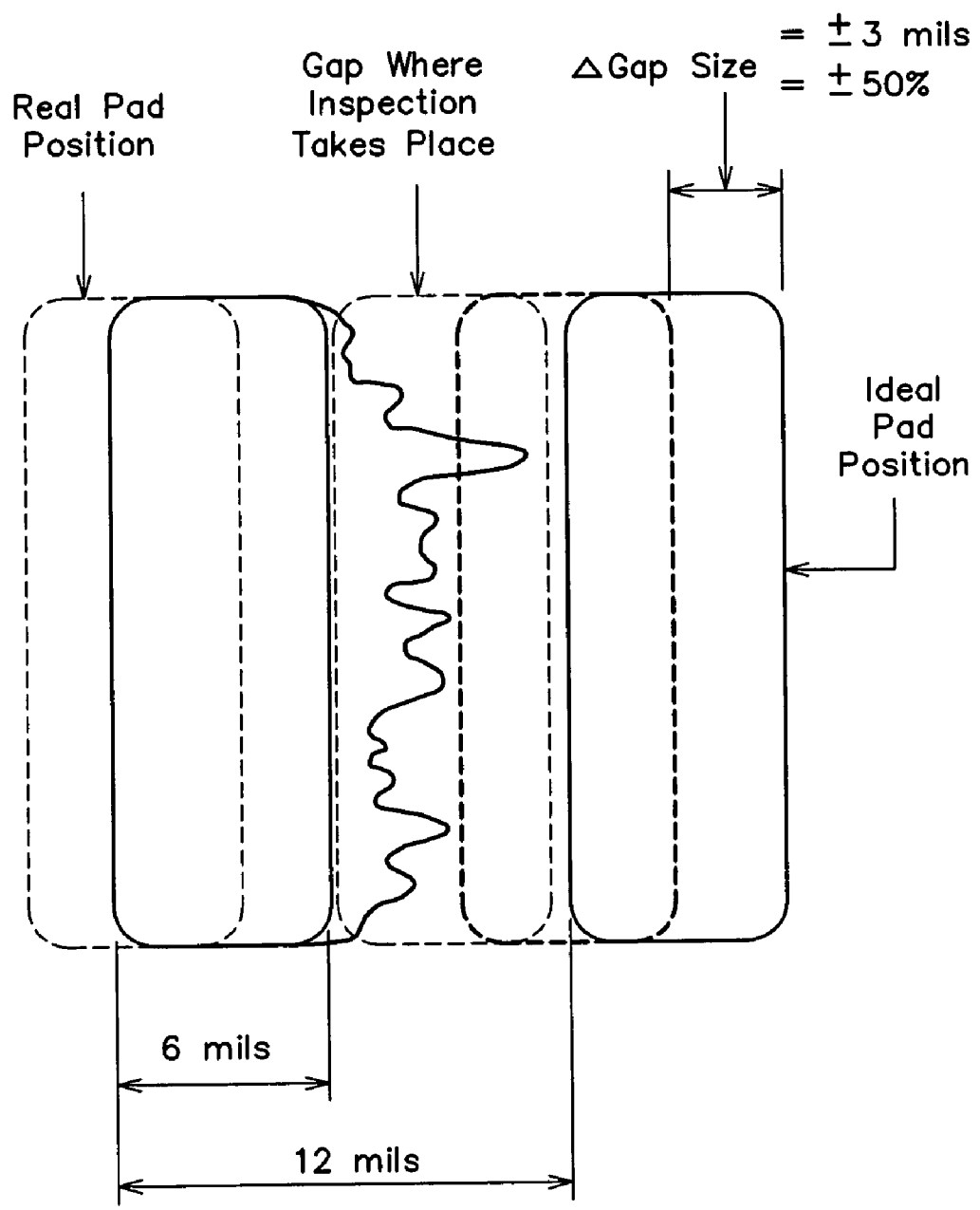
FIG. 27 is an illustration showing the effect of variations in pad position on gap size, in accordance with an embodiment of the invention.

FIG. 26 is an illustration showing the effect of variations in pad size on gap size, in accordance with an embodiment of the invention, and FIG. 27 is an illustration showing the effect of variations in pad position on gap size, in accordance with an embodiment of the invention. As FIGS. 26 and 27 illustrate, the gap size can vary depending on the pad size and pad placement. Because at least some embodiments of the invention permit user specified inputs for parameters such as maximum span of a significant bridge feature across a gap, size of sliding average window, etc. (see FIG. 22), the systems and methods of the invention advantageously may be quickly adapted to substrates of varying sizes, with varying pad sizes and placements.

Figure 28:
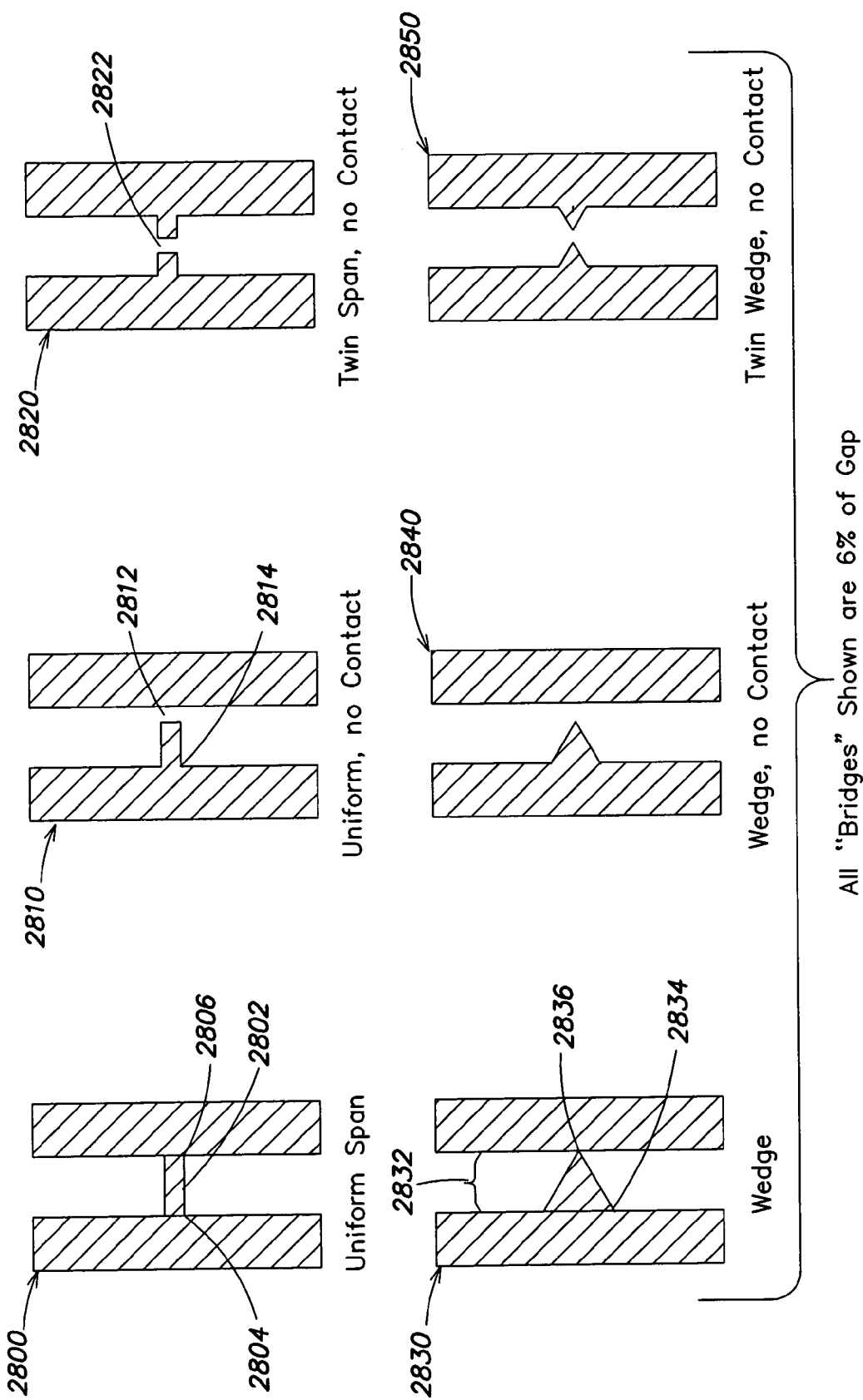
FIG. 28 is a first representative illustration showing types of bridges/bridge-like features that may be detectable using one embodiment of the invention.
Figure 29:
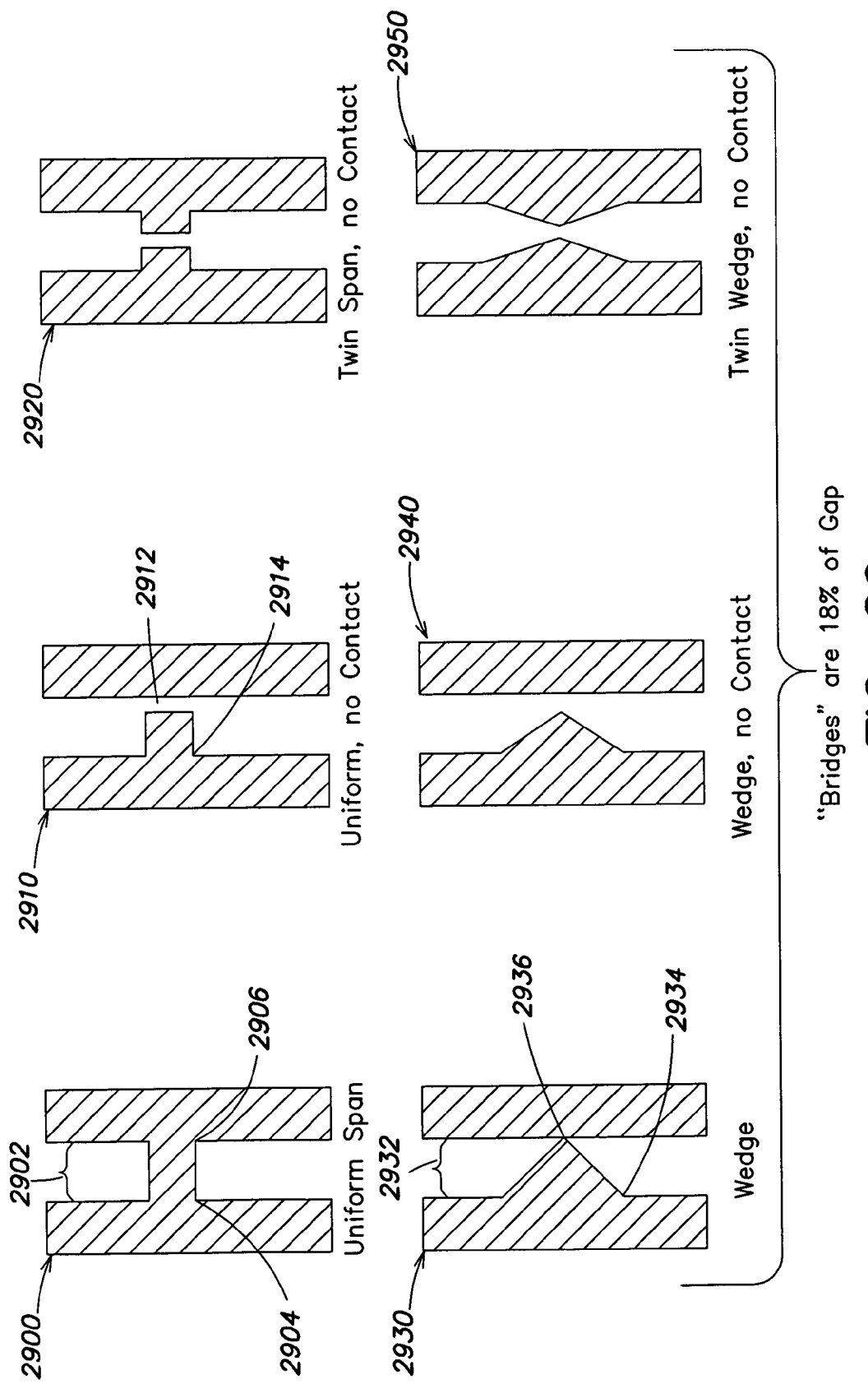
FIG. 29 is a second representative illustration showing types of bridges/bridge-like features that may be detectable using one embodiment of the invention.
Figure 30:
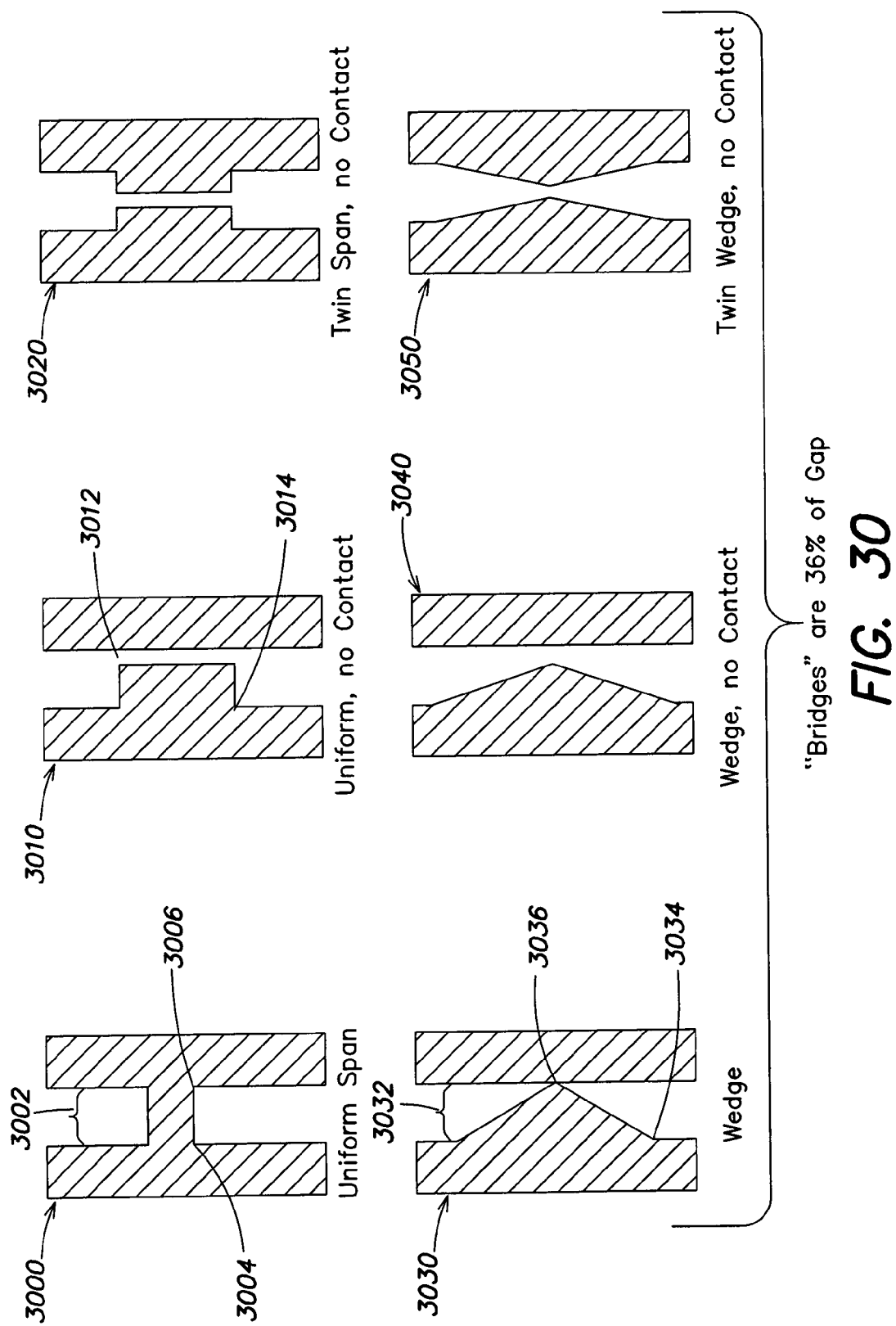
FIG. 30 is a third representative illustration showing types of bridges/bridge-like features that may be detectable using one embodiment of the invention.

FIGS. 28–30 are representative illustrations showing types of bridges and bridge-like features that may be detectable using one embodiment of the invention. All bridge-like features are precisely drawn to cover exactly 6%, 18%, and 36% of the total gap area in FIGS. 28, 29, and 30, respectively, regardless of shape. Only the geometry of bridge-like features is changed to demonstrate how various shapes affect the probability that a bridge defect will occur later in a process called "reflow", where the solder paste is heated to a molten state, thus enabling redistribution of the solder deposit via surface tension. Of course, naturally occurring bridge-like features would be more randomly shaped, but they would share most of the basic characteristics shown in these illustrations. Only FIG. 28 is described in detail in the following paragraphs, although the same descriptions apply to like figures in FIGS. 29 and 30.

In FIG. 28, item 2800 shows a bridge-like paste feature that extends the full span of the gap between two adjacent pad deposits, making contact with both, in what can be called "classic" bridge geometry. The bridge feature 2802 has uniform thickness across the full span of the gap, with no part any more likely to break and "pull back" via surface tension during subsequent reflow operations. During reflow operations, surface tension would create a tendency to "wick" the molten solder, previously a solder paste, back toward junctions 2804 and 2806, both tending to broaden to the point of contact 2804 and 2806, and thinning the center of the bridge feature. Eventually, under certain conditions, the feature may become thin enough to break and pull back with each portion migrating toward respective "junctions" 2804 and 2806.

The maximum value produced by the sliding average of the projected data, as described in this invention, is dependent on the size of the sliding average, i.e., the smoothing kernel. In a preferred method, the size of the sliding average is determined by a user-defined "sensitivity" setting. For a specific kernel size, or given sensitivity, the size and shape of the bridge feature determines how much of an effect the smoothing kernel will have on the projected data and thus the maximum value after smoothing. The maximum value can be considered the effective span of features with at least enough "bulk" or "power" to survive the smoothing operation. Referring briefly again to FIG. 24, an actual bridge feature can be seen in 24B that is similar in relative size and shape to the bridge example 2802, so it will be used here to show, in actual practice, the effect of smoothing similarly shaped bridge-like features. Both features span 100% of the gap. FIG. 24D shows a plot 2410 of the smoothed data with a maximum value of about 85% at the bridge location. The feature is flagged as a defect if the maximum smoothed span, in this case 85%, is above the user-defined limit.

FIG. 28 shows a uniform bridge feature 2810 making contact with only one pad deposit at 2814. In this case a "break" 2812 is already present, therefore the probability of "pull back" is greater in 2810 than in 2800, since surface tension favors only one side, with no counteraction from the opposite side. Note that the point of contact 2814 with the pad deposit is slightly larger than that of junction 2804, as required to maintain the same 6% gap coverage for all bridge examples shown in FIGS. 28A–F. Given the same bridge "sensitivity", the effect of smoothing the projected data of 2810 would be similar to the previous example 2800, since they have nearly the same uniform thickness, but the effective span (i.e. maximum smoothed value) would be less than in the previous example. Again, the feature is flagged as a defect if the maximum smoothed span is above the user-defined limit.

FIG. 28, item 2820, also has a "break" 2822, similar to 2812, but located mid-span.

FIG. 28, item 2830, is similar to item 2800 in that contact is made on both sides of the gap. Shape is the main difference here with a broader base of contact 2834 on one side of the gap, and a much smaller point of contact 2836 on the other. The point 2836 would provide little of the "wicking" tendencies that the much larger base 2834 would provide. Also, upon similarly smoothing the projected data of bridge features 2832 and 2802, the effective span (maximum of smoothed values) of the triangle shaped feature 2832 would be less than that of the uniformly shaped 2802. The difference in effective span correctly implies that 2802 has more significant bridge potential than does 2832, and although both reported spans must be checked against the user-defined span limits, feature 2832 is less likely to be flagged as a defect than 2802. FIG. 29 includes items 2900, 2910, 2920, 2930, 2940, and 2950. FIG. 30 includes items 3000, 3010, 3020, 3030, 3040, and 3050. FIGS. 29 and 30 present bridge–like features in nearly identical format as in FIG. 28 with one notable difference. While all bridge features shown in FIG. 28 cover exactly 6% of the gap, in FIG. 29 they cover 18% of the gap, and in FIG. 30, 36%. Upon smoothing the projected data of like bridge features in FIGS. 28, 29, and 30, using the same kernel, the effective span of the larger deposits would be greater. Again, the difference in effective span correctly implies that relatively larger deposits have more significant bridge potential than do smaller deposits, and although all reported spans must be checked against the user-defined span limits, larger ones are more likely to be flagged as a defect. In addition, general paste-in-gap area must also be checked against the user-defined limits, and while these are typically set to catch gross defects that may also have significant bridge potential, here too the larger deposits are more likely to be flagged as a defect than the smaller ones.

Figure 31:
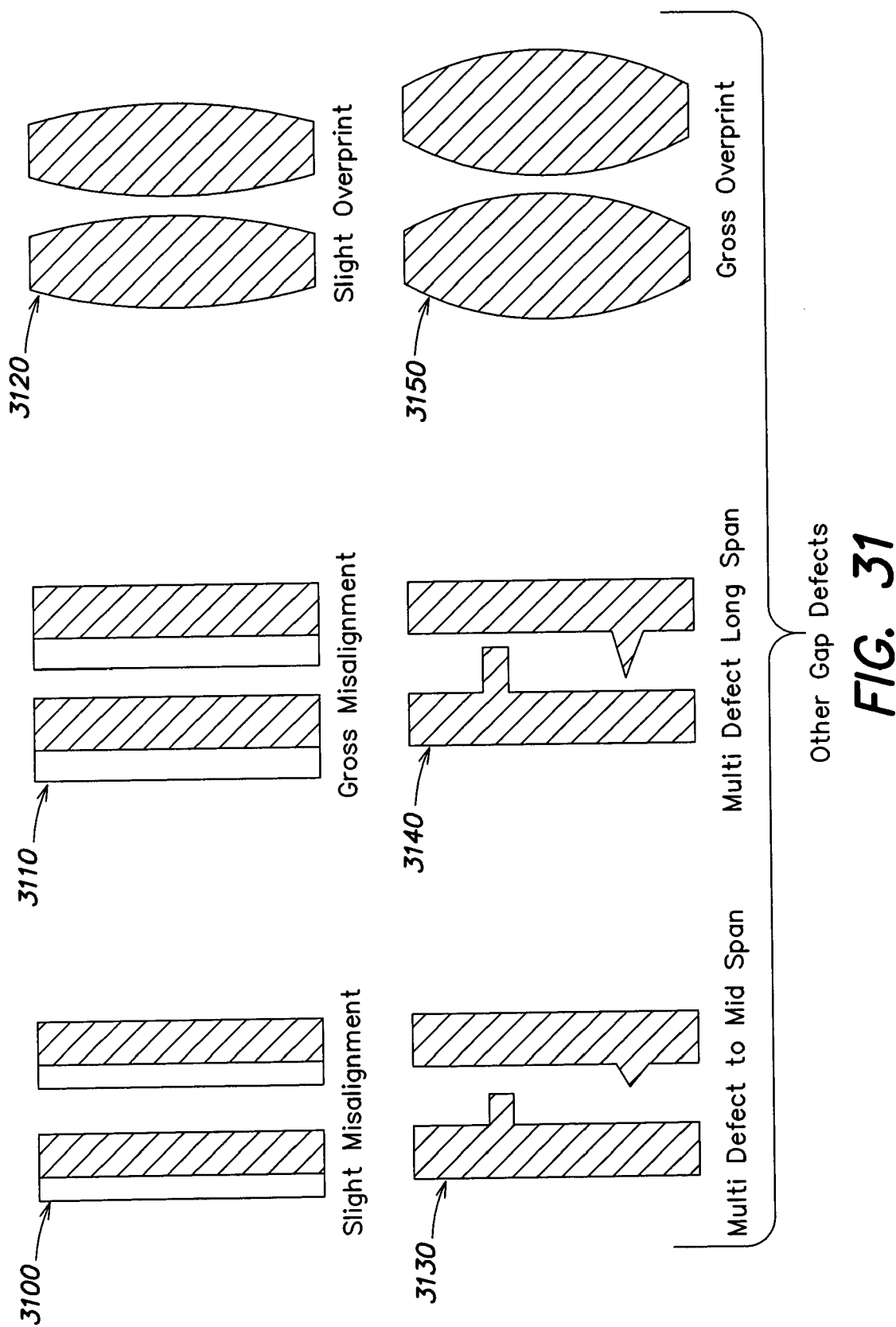
FIG. 31 is a representative illustration of various types of screen printing/solder paste printing defects that may be detectable in accordance with at least some embodiments of the invention.

FIG. 31 is a representative illustration of other types of screen printing/solder paste printing defects that may be detectable in accordance with at least some embodiments of the invention. FIG. 31, item 3100 shows a common print defect due to poor general paste alignment. In this case reported paste-in-gap values would rise with the degree of misalignment, as would the reported span of paste across the gap. FIG. 31, item 3110 shows the effect of gross misalignment. For the purpose of estimating future bridge potential, this invention would correctly estimate the increased potential of a bridge related defect as a function of paste alignment.

FIG. 31, items 3130 and 3140, show multiple unique defects where length of span and shape of the feature determine defect potential. In item 3130 both features extend to mid-gap, although from opposite sides, and both cover the same amount of gap area. This method of this invention operates on both features simultaneously and, as first demonstrated in FIG. 28, the rectangular feature would correctly produce the largest gap span after smoothing operations. The same is true for similar features in item 3140, although the maximum reported span would be greater, and thus the bridging potential, in this example.

FIG. 31, items 3120 and 3150, show slight and gross over-print respectively. In both cases, the effective span of paste across the gap is greatest near the center of the gap. Only the cumulative effect of paste in the bridging direction is important. In this way, the simple projection and sliding average method used in this invention is able to correctly determine that item 3150 has greater bridging potential than does item 3120, based on the difference in reported effective span. Also, the reported paste-in-gap area would be greater for item 3150 than for item 3120, thus item 3150 would be first to correctly indicate a paste-in-gap defect on this account as well.

FIGS. 28–31 and associated descriptions demonstrate the methods used in this invention to correctly estimate the effective "bridging potential" of a paste deposit, based on user-defined "sensitivity" parameters, as well as to detect and flag bridge defects that may adversely affect subsequent processes, based on user-defined limits.

It has been found that the methods for detection of defects such as bridges is more successful when accurate and reliable paste detection methods are used to separate paste from background. Advantageously, the texture-based paste detection method disclosed herein and in application Ser. No. 09/304,699 may be combined with the bridge analysis technique disclosed herein to provide useful and reliable measurement of bridge characteristics that are relevant to the board assembly process.

In describing the embodiments of the invention illustrated in the figures, specific terminology is used for the sake of clarity. However, the invention is not limited to the specific terms so selected, and each specific term at least includes all technical and functional equivalents that operate in a similar manner to accomplish a similar purpose.

As those skilled in the art will recognize variations, modifications, and other implementations of what is described herein can occur to those of ordinary skill in the art without departing from the spirit and the scope of the invention as claimed. Further, virtually any aspect of the embodiments of the invention described herein can be implemented using software, hardware, or in a combination of hardware and software.

It should be understood that, in the Figures of this application, in some instances, a plurality of system elements or method steps may be shown as illustrative of a particular system element, and a single system element or method step may be shown as illustrative of a plurality of a particular systems elements or method steps. It should be understood that showing a plurality of a particular element or step is not intended to imply that a system or method implemented in accordance with the invention must comprise more than one of that element or step, nor is it intended by illustrating a single element or step that the invention is limited to embodiments having only a single one of that respective elements or steps. In addition, the total number of elements or steps shown for a particular system element or method is not intended to be limiting; those skilled in the art will recognize that the number of a particular system element or method steps can, in some instances, be selected to accommodate the particular user needs.

Although the invention has been described and pictured in a preferred form with a certain degree of particularity, it is understood that the present disclosure of the preferred form, has been made only by way of example, and that numerous changes in the details of construction and combination and arrangement of parts may be made without departing from the spirit and scope of the invention as hereinafter claimed.

What is claimed is:
1. A method of inspecting a stencil having apertures through which a substance is deposited onto an electronic substrate comprising:
   depositing the substance through the stencil and onto the substrate;
   capturing a first image of the stencil after the deposit of the substance and detecting variations in texture of the substance in the first image;
   capturing a second image of the electronic substrate having the substance on its surface and detecting variations in texture of the substance in the second image;
   defining a region of interest in the first image and in the second image to determine whether at least one feature exists in the region of interest;
   measuring a first span of the at least one feature in the region of interest in the first image and a second span of the at least one feature in the region of interest in the second image; and
   correlating the first span of the at least one feature and the second span of the at least one feature to determine whether a threshold span of the at least one feature has been reached.

2. The method of claim 1 wherein the at least one feature includes at least one of a short circuit, a bridge-like feature, a bridge, an excess quantity of the substance, and a stray area of the substance.

3. The method of claim 1 further comprising altering a process by which the substance is deposited on the electronic substrate when the threshold span of the at least one feature has been met or exceeded.

4. The method of claim 1 wherein the step of correlating is accomplished in accordance with at least one detection parameter.

5. The method of claim 4 further comprising computing, for each feature in the region of interest, an area and geometry of the at least one feature, the computation accomplished using at least one detection parameter.

6. The method of claim 5 further comprising determining, based on the area and geometry, that the at least one feature in the image requires a corrective action.

7. The method of claim 1 wherein the electronic substrate is a printed circuit board.

8. The method of claim 1 wherein the substance includes solder paste.

9. A method of detecting a defect in a substance deposited through a stencil and onto a substrate, comprising:
   capturing an image of the stencil;
   detecting variations in texture in the image to determine a location of the substance on the stencil;
   defining a region of interest in the image, the defined region of interest having a first axis, wherein a set of pixels in the image lie along the axis;
   computing, for each pixel along the axis, a sum of all the pixels in the region of interest that are in perpendicular alignment with the respective pixel along the axis;
   representing the sums of each pixel along the axis as a single dimensional array perpendicular to the axis;
   evaluating the single dimensional array to determine whether any defects exist in the region of interest; and
   actuating a stencil wipe procedure to clean the stencil when a defect exists in the region of interest.

10. The method of claim 9 wherein the substance comprises solder paste.

11. The method of claim 9 wherein the defect comprises at least one of a solder bridge, a bridge-like feature, or an excess paste feature.

12. The method of claim 9 wherein the stencil includes first and second apertures, separated by a distance, through which the solder paste is deposited and the defect comprises the existence of solder paste spanning at least a portion of the distance between the first and second apertures.

13. The method of claim 9 further comprising applying a rule to determine whether the defect should be classified as a solder bridge.

14. A method of inspecting a stencil having apertures through which a substance is deposited onto an electronic substrate comprising:
   depositing the substance through the stencil and onto the substrate;
   capturing a first image of the stencil after the deposit of the substance and detecting variations in texture of the substance in the first image;
   capturing a second image of the electronic substrate having the substance on its surface and detecting variations in texture of the substance in the second image;
   defining a region of interest in the first image and in the second image to determine whether at least one feature exists in the region of interest;
   measuring a first span of the at least one feature in the region of interest in the first image and a second span of the at least one feature in the region of interest in the second image;
   correlating the first span of the at least one feature and the second span of the at least one feature to determine whether a threshold span of the at least one feature has been reached; and
   actuating a stencil wipe to clean a surface of the stencil when it is determined that the threshold span has been reached.

15. A method of dispensing material at predetermined locations through a stencil and onto an electronic substrate within a stencil printer, the method comprising:
   delivering a substrate to a stencil printer;
   positioning the substrate in a print position;
   positioning a stencil onto the substrate;
   dispensing the material through the stencil and onto the substrate;
   performing texture-based recognition of a predetermined location of the material on a bottom side of the stencil;
   determining whether there is at least one feature in the predetermined location on the bottom side of the stencil;
   comparing the at least one feature on the bottom side of the stencil with a position of the substance on the substrate to determine whether the at least one feature is a defect; and
   actuating a stencil wipe procedure to clean the bottom side of the stencil when the at least one feature is determined to be a defect.

16. The method of claim 15 wherein the at least one feature includes at least one of a defect, a short circuit, a bridge-like feature, a bridge, an excess quantity of the substance and a stray area of the substance.

17. The method of claim 15 wherein the electronic substrate is a printed circuit board.

18. The method of claim 15 wherein the substance includes solder paste.

19. The method of claim 18 further comprising performing texture-based recognition of a solder paste deposit located on the substrate and comparing solder paste deposits on the substrate with solder paste deposits on the stencil.

* * * * *